United States Patent
Poirier et al.

(10) Patent No.: US 11,884,723 B2
(45) Date of Patent: *Jan. 30, 2024

(54) USE OF ANTI-HUMAN SIRPA V1 ANTIBODIES AND METHOD FOR PRODUCING ANTI-SIRPA V1 ANTIBODIES

(71) Applicant: OSE IMMUNOTHERAPEUTICS, Nantes (FR)

(72) Inventors: Nicolas Poirier, Treillieres (FR); Vanessa Gauttier, Reze (FR); Caroline Mary, Sainte-Pazanne (FR); Sabrina Pengam, Sainte-Luce-sur-Loire (FR); Bernard Vanhove, Reze (FR)

(73) Assignee: OSE IMMUNOTHERAPEUTICS, Nantes (FR)

( * ) Notice: Subject to any disclaimer, the term of this patent is extended or adjusted under 35 U.S.C. 154(b) by 330 days.

This patent is subject to a terminal disclaimer.

(21) Appl. No.: 16/979,627

(22) PCT Filed: Mar. 13, 2019

(86) PCT No.: PCT/EP2019/056250
§ 371 (c)(1),
(2) Date: Sep. 10, 2020

(87) PCT Pub. No.: WO2019/175218
PCT Pub. Date: Sep. 19, 2019

(65) Prior Publication Data
US 2021/0040206 A1 Feb. 11, 2021

(30) Foreign Application Priority Data
Mar. 13, 2018 (EP) .................... 18305271

(51) Int. Cl.
*C07K 16/28* (2006.01)
*A61K 45/06* (2006.01)

(52) U.S. Cl.
CPC .......... *C07K 16/2803* (2013.01); *A61K 45/06* (2013.01); *C07K 2317/565* (2013.01); *C07K 2317/76* (2013.01)

(58) Field of Classification Search
CPC .......... C07K 16/2803; C07K 2317/565; C07K 2317/76; C07K 2317/34; C07K 2317/74; C07K 2317/80; C07K 2317/92; C07K 14/70503; C07K 14/70532; C07K 16/2896; A61K 45/06; A61K 2039/505; A61P 35/00
See application file for complete search history.

(56) References Cited

U.S. PATENT DOCUMENTS

| 11,279,766 B2 | 3/2022 | Poirier et al. |
| 2010/0215640 A1 | 8/2010 | Clemmons et al. |
| 2010/0233251 A1 | 9/2010 | Von Andrian et al. |
| 2010/0239578 A1 | 9/2010 | Danska et al. |
| 2012/0039896 A1 | 2/2012 | Clemmons et al. |
| 2012/0070461 A1 | 3/2012 | Singh et al. |
| 2014/0141002 A1 | 5/2014 | Clemmons et al. |
| 2014/0242095 A1 | 8/2014 | Wang et al. |
| 2017/0247464 A1 | 8/2017 | Poirier et al. |
| 2018/0312600 A1 | 11/2018 | Poirier et al. |
| 2019/0127477 A1 | 5/2019 | Poirier et al. |
| 2021/0179728 A1 | 6/2021 | Poirier et al. |

FOREIGN PATENT DOCUMENTS

| EP | 1637598 A1 | 3/2006 |
| WO | 2007005874 A2 | 1/2007 |
| WO | 2009131453 A1 | 10/2009 |
| WO | 2010077634 A1 | 7/2010 |
| WO | 2010130053 A1 | 11/2010 |
| WO | 2012149416 A2 | 11/2012 |
| WO | 2013056352 A1 | 4/2013 |
| WO | 2013079174 A1 | 6/2013 |
| WO | 2013109752 A1 | 7/2013 |
| WO | 2015048312 A1 | 4/2015 |
| WO | 2015138600 A2 | 9/2015 |
| WO | 2016063233 A1 | 4/2016 |
| WO | 2017178653 A2 | 10/2017 |
| WO | 2019073080 A1 | 4/2019 |

OTHER PUBLICATIONS

Kong et al. Clin Transl Oncol 18:1051-1055, (2016) (Year: 2016).*
McCracken et al. Clin Cancer Res, 21(16):3597-3601 (2015) (Year: 2015).*
Megahed Lancet, 259:1921-1922 (2002) (Year: 2002).*
International Search Report and Written Opinion for PCT/EP2019/056250 dated Jun. 18, 2019.
Takenaka et al., "Polymorphism in SIRP? Modulates Engraftment of Human Hematopoietic Stem Cells", Nature Immunology, 2007, pp. 1313-1323, vol. 8, <https://doi.org/10.1038/ni1527>.
Yanagita et al., "Anti-SIRPa Antibodies as a Potential New Tool for Cancer Immunotherapy", JCI Insight, Jan. 2017, pp. 1-15, vol. 2, No. 1, e89140.

(Continued)

*Primary Examiner* — Julie Wu
(74) *Attorney, Agent, or Firm* — Thompson Coburn LLP; William A. Holtz

(57) ABSTRACT

The invention is in the field of immunotherapy. The present invention provides antibodies useful in therapeutic and diagnostic applications targeting human SIRPa, said antibodies enhancing the cross-presentation of antigens to T cells. The invention also provides antibodies against specific isoforms of SIRP a and able to disrupt the interaction between those isoforms of SIRP a and human CD47 for use in treating or preventing a disease, or diagnostic applications, and methods for producing and/or selecting antihuman SIRPa antibodies that bind with different affinities to various isoforms of human SIRP members.

20 Claims, 9 Drawing Sheets

Specification includes a Sequence Listing.

(56) References Cited

OTHER PUBLICATIONS

UniProt Sequence Accession P42081 for PDCD1_Human; retrieved from the internet site https://uniprot.org/uniprot/ on Mar. 26, 2020.
UniProt Sequence Accession Q15116 for PDCD1_Human; retrieved from the internet site https://uniprot.org/uniprot/ on Mar. 26, 2020.
UniProt Sequence Accession Q9NZQ7 for PDCD1_Human; retrieved from the internet site https://uniprot.org/uniprot/ on Mar. 26, 2020.
Vinay et al., "Therapeutic Potential of Anti-CD137 (4-1BB) Monoclonal Antibodies", Expert Opin. Ther. Targets., 2016, pp. 361-373, vol. 20, No. 3.
Vonderheide, "CD47 Blockade as Another Immune Checkpoint Therapy for Cancer", Nature Medicine, Oct. 2015, pp. 1122-1123, vol. 21, No. 10.
Wakabayashi et al., "Prevention of Metastasis by a Polyamine Synthesis Inhibitor in an Animal Bone Metastasis Model", Oncology, 2000, pp. 75-80, vol. 59.
Wan et al., "Aberrant Regulation of Synovial T Cell Activation by Soluble Costimulatory molecules in Rheumatoid Arthritis", J. Immunol., 2006, pp. 8844-8850, vol. 177.
Wang et al., "Immune Regulation by 4-1BB and 4-1BBL: Complexities and Challenges", Immunol. Rev., 2009, pp. 192-215, vol. 229, No. 1.
Weiskopf et al, "Direct SIRPa Blockade Augments Macrophage Responses to Therapeutic Anticancer Antibodies", Blood Journal, Dec. 2014, vol. 124, No. 21, Abstract.
Willingham et al., "The CD47-Signal Regulatory Protein Alpha (SIRPa) Interaction is a Therapeutic Target for Human Solid Tumors", Proceedings of the National Academy of Sciences, Apr. 2012, pp. 6662-6667, vol. 109, No. 17.
Willoughby et al., "OX40: Structure and Function—What Questions Remain?", Mol. Immunol., 2017, pp. 13-22, vol. 83.
Written Opinion issued in corresponding International Patent Application No. PCT/IB2015/058124 dated Jan. 19, 2016.
Zak et al., "Structure of the Complex of Human Programmed Death 1, PD-1, and Its Ligand PD-L1", Structure, 2015, pp. 2341-2348, vol. 23, No. 12.
Zhao et al., "CD47-Singal Regulatory Protein—(SIRP) Interactions Form a Barrier for Antibody-Mediated Tumor Cell Destruction", Proceedings of the National Academy of Sciences, Nov. 8, 2011, pp. 18342-18347, vol. 108, No. 45.
Abe et al., "Blockade of CD47-Signaling Regulatory Protein Alpha Signaling Enhances the Macrophage Phagocytic Activity Against Cancer Cells", Transplantation, Abstract B1139, Jul. 2014. pp. 313, vol. 98, Suppl. 1, World Transplantation Congress.
Alblas et al., "Signal Regulatory Protein Ligation Induces Macrophage Nitric Oxide Production Through JAK/STAT and Phosphatidylinositol 3-Kinase/Racl/NAPDH Oxidase/H2O2-Dependent Pathways", Molecular and Cellular Biology, Aug. 15, 2005, pp. 7181-7192, vol. 25, No. 16.
Ansell, "Targeting Immune Checkpoints in Lymphoma", Current Opinion in Hematology, 2015, pp. 337-342, vol. 22, No. 4.
Barclay et al., "The Interaction Between Signal Regulatory Protein Alpha (SIRP?) and CD47: Structure, Function, and Therapeutic Target", Annu. Rev. Immunol., Nov. 6, 2013, pp. 25-50.
Borch et al., "Reorienting the Immune System in the Treatment of Cancer by Using Anti-PD-1 and Anti-PD-L1 Antibodies", Drug Discovery Today, Sep. 2015, pp. 1127-1134, vol. 20, No. 9.
Brahmer et al., "Safety and Activity of Anti-PD-L1 Antibody in Patients with Advanced Cancer", N. Eng. J. Med., 2012, pp. 2455-2465, vol. 366, No. 26.
Chao et al., "Response: Mechanisms of Targeting CD47-SIRP [Alpha] in Hematologic Malignancies", Blood American Society of Hematology, May 3, 2012, pp. 4334-4335, vol. 119, No. 18.
Crepeau et al., "Challenges and Opportunities in Targeting the CD28/CTLA-4 Pathway in Transplantation and Autoimmunity", Expert Opin. Biol. Ther., 2017, pp. 1001-1012, vol. 17, No. 8.
Dugast et al., "Myeloid-Derived Suppressor Cells Accumulate in Kidney Allograft Tolerance and Specifically Suppress Effector T Cell Expansion", The Journal of Immunology, Jun. 15, 2008, pp. 7898-7906, vol. 180, Issue. 12.

English Translation of Decision of Refusal for Japanese App No. 2018-521040, dated Sep. 21, 2021.
English Translation of Decision to Grant for Japanese App No. 2017-520986, dated Apr. 12, 2021.
English Translation of First Office Action for Japanese App No. 2017-520986, dated Aug. 5, 2019.
English Translation of First Office Action for Japanese App No. 2018-521040, dated Oct. 13, 2020.
English Translation of Second Office Action for Japanese App No. 2017-520986, dated May 21, 2020.
Gabrilovich et al., "Myeloid-Derived Suppressor Cells as Regulators of the Immune System", Nat Rev Immunol, Mar. 2009, pp. 162-174, vol. 9, Issue 3.
Gauttier et al., "Dual Targeting of Adaptive and Innate Immune Checkpoints Induce Potent Memory Anti-Tumor Response", European Journal of Cancer, Jul. 2016, pp. S216-S217, vol. 61, Supplement 1.
Gilbreth et al., "Crystal Structure of the Human 4-1BB/4-1BBL Complex", J. Biol. Chem., 2018, pp. 9880-9891, vol. 293, No. 25.
Girard et al., "CD80 and CD86 IgC Domains are Important for Quaternary Structure, Receptor Binding and Co-Signaling Function", Immunology Letters, 2014, Article in Press, pp. 1-11.
Hatherley et al., "The Structure of the Macrophage Signal Regulatory Protein (SIRP) Inhibitory Receptor Reveals a Binding Face Reminiscent of That Used by T Cell Receptors", Journal of Biological Chemistry, Mar. 16, 2007, pp. 14567-14575, vol. 282, No. 19.
International Search Report and Written Opinion for PCT/EP2017/059071 dated Jun. 5, 2018.
International Search Report issued in corresponding international Patent Application No. PCT/IB2015/058124 dated Jan. 19, 2016.
Ishida et al., "Induced Expression of PD-1, A Novel Member of the immunoglobulin Gene Superfamily, Upon Programmed Cell Death", EMBO J., 1992, pp. 3887-3895, vol. 11, No. 11.
Justice et al., "Using the Mouse to Model Human Disease: Increasing Validity and Reproducibility", Disease, Models & Mechanisms, 2016, pp. 101-103, vol. 9.
Lee et al, "Novel Structural Determinants on SIRPa that Mediate Binding to CD47", The Journal of Immunology, Dec. 1, 2007, pp. 7741-7750, vol. 179, No. 11.
Lin et al., "The PD-1/PD-1L Complex Resembles the Antigen-Binding Fv Domains of Antibodies and T Cell Receptors", PNAS, 2008, pp. 3011-3016, vol. 15, No. 8.
Liu et al., "Functional Elements on SIRP? IgV Domain Mediate Cell Surface Binding to CD47", Journal of Molecular Biology, Jan. 2007, pp. 680-693, vol. 365, No. 3.
Liu et al., "Signal Regulatory Protein (SIRPalpha), a Cellular Ligand for CD47, Regulates Neutrophil Transmigration," Journal of Biological Chemistry, Mar. 15, 2002, pp. 10028-10036, vol. 277, No. 12.
Makarova-Rusher et al., "The Yin and Yang of Evasion and Immune Activation in HCC", Journal of Hepatology, Jun. 2015, pp. 1420-1429, vol. 62, No. 6.
Mosser et al, "Exploring the Full Spectrum of Macrophage Activation", Nature Reviews Immunology, 2008, pp. 958-969, vol. 8 No. 12.
Nielsen et al., "Alternative Splice Variants of the Human PD-1-Gene", Cell Immunol., 2005, pp. 109-116, vol. 235.
Ochando et al., "Myeloid-Derived Suppressor Cells in Transplantation and Cancer", Immunologic Research, Apr. 26, 2012, pp. 275-285, vol. 54, No. 1-3.
Oldenborg et al., "Role of CD47 as a Marker of Self on Red Blood Cells", Science, Jun. 2000, pp. 2051-2054, vol. 288, No. 5473.
Pan et al., "Signal Regulatory Protein [Alpha] is Associated with Tumor-Polarized Macrophages Phenotype Switch and Plays a Pibotal Role in Tumor Progression", Hepatology, Aug. 1, 203, pp. 680-691, vol. 58, No. 2.
Pardoll, "The Blockade of Immune Checkpoints in Cancer Immunotherapy", Nature Reviews Cancer, 2012, pp. 252-264, vol. 12, No. 4.
Peach et al., "Both Extracellular Immunoglobin-Like Domains of CD80 Contains Residues Critical for Binding T-Cell Surface Receptors CTLA-4 and CD28", J. Biol. Chem., 1995, pp. 21181-21187.

(56) References Cited

OTHER PUBLICATIONS

Powles et al., "MPDL3280A (Anti-PD-L1_ Treatment Leads to Clinical Activity in Metastatic Bladder Cancer", Nature, 2014, pp. 558-562, Methods, Extended Data Figures 1-3, and Extended Data Table 1-3, vol. 515, No. 7528.

Reuter, "Diet-Induced Models for Obesity and Type 2 Diabetes", Drug Discovery Today: Disease Models, 2007, pp. 3-8, vol. 4/1.

Seiffert et al., "Signal-Regulatory Protein Alpha (SIRPalpha) but not SIRPbeta is Involved in T-cell Activation, Binds to CD47 with High Affinity, and is Expressed on Immature CD34(+)CD38(−) Hematopoietic Cells", Blood, May 2001, pp. 2741-2749, vol. 97, No. 9.

Sharma et al., "Immune Checkpoint Targeting in Cancer Therapy: Towards Combination Strategies with Curative Potential", Cell, 2015, pp. 205-214, vol. 161, No. 2.

Sim et al., " Discovery of High Affinity, Pan-Allelic, and Pan-Mammalian Reactive Antibodies Against the Myeloid Checkpoint Receptor SIRPa ", MABS, 2019, pp. 1036-1052, vol. 11, No. 6.

Solito et al, "Myeloid-Derived Suppressor Cell Heterogeneity in Human Cancers", Ann. N.Y. Acad. Sci. Jun. 2014, pp. 47-65, vol. 1319, Issue. 1.

Srivastava et al., "Targeting MDSCs Enhance Therapeutic Vaccination Responses Against Lung Cancer", Oncoimmunology, Dec. 2012, pp. 1650-1651, vol. 1, No. 9.

Stefanidakis et al., "Endothelial CD47 interaction with SIRPγ is required for human T-cell transendothelial migration under shear flow conditions in vitro", The American Society of Hematology, Blood, Aug. 15, 2008, pp. 1280-1289, vol. 112, No. 4.

Topalian et al., "Safety, Activity, and Immune Correlates of Anti-PD-1 Antibody in Cancer", The new England Journal of Medicine, 2012, pp. 2443-2454, vol. 366, No. 26.

Türkbeyler et al., "Prolidase Could Act as a Diagnosis and Treatment Mediator in Lung Fibrosis", Inflammation, Oct. 2012, pp. 1747-1752, vol. 35, No. 5.

Jeda et al., "Association of the T-Cell Regulatory Gene CTLA4 with Susceptibility to Autoimmune Disease", Nature, 2003, pp. 506-511, vol. 423.

UniProt Sequence Accession O75144 for PDCD1_Human; retrieved from the internet site https://uniprot.org/uniprot/ on Mar. 26, 2020.

UniProt Sequence Accession P23510 for PDCD1_Human; retrieved from the internet site https://uniprot.org/uniprot/ on Mar. 26, 2020.

UniProt Sequence Accession P33681 for PDCD1_Human; retrieved from the internet site https://uniprot.org/uniprot/ on Mar. 26, 2020.

UniProt Sequence Accession P41273 for PDCD1_Human; retrieved from the internet site https://uniprot.org/uniprot/ on Mar. 26, 2020.

* cited by examiner

```
                                    1                   2 3 4 5    6    7
P78324_SIRPA_HUMAN_variant1    MEPAGPAPGRLGPLLCLLLAASCAWSGVAGEEELQVIQPDKSVLVAAGETATLRCTATSL    60
SIRPA_HUMAN_variant2           MEPAGPAPGRLGPLLCLLLAASCAWSGVAGEEELQVIQPDKSVSVAAGESAILHCTVTSL    60
O00241_SIRPB_HUMAN             MPVPASWPHLPSPFLLMTL-LLGRLTGVAGEDELQVIQPEKSVSVAAGESATLRCAMTSL    59
Q9P1W8_SIRPG_HUMAN             MPVPASWPHPPGPFLLLTL-LLG-LTEVAGEEELQMIQPEKLLLVTVGKTATLHCTVTSL    58

8           9 10 11 12 13      14 ?
P78324_SIRPA_HUMAN_variant1    IPVGPIQWFRGAGPGRELIYNQKEGHFPRVTTVSDLTKRNNMDFSIRIGNITPADAGTYY   120
SIRPA_HUMAN_variant2           IPVGPIQWFRGAGPARELIYNQKEGHFPRVTTVSESTKRENMDFSISISNETPADAGTYY   120
O00241_SIRPB_HUMAN             IPVGPIMWFRGAGAGREL IYNQKEGHFPRVTTVSELTKRNNLDFSISISNITPADAGTYY   119
Q9P1W8_SIRPG_HUMAN             LPVGPVLWFRGVGPGREL IYNQKEGHFPRVTTVSDLTKRNNMDFSIRISSITPADVGTYY   118

15 16=17
P78324_SIRPA_HUMAN_variant1    CVKFRKGSPDDVEFKSGAGTELSVRAKPSAPVVSGPAARATPQHTVSFTCESHGFSPRDI   180
SIRPA_HUMAN_variant2           CVKFRKGSPD-TEFKSGAGTELSVRAKPSAPVVSGPAARATPQHTVSFTCESHGFSPRDI   179
O00241_SIRPB_HUMAN             CVKFRKGSPDDVEFKSGAGTELSVRAKPSAPVVSGPAVRATPEHTVSFTCESHGFSPRDI   179
Q9P1W8_SIRPG_HUMAN             CVKFRKGSPENVEFKSGPGTEMALGAKPSAPVVLGPAARTTPEHTVSFTCESHGFSPRDI   178
```

| | ED50 (ng/ml) |
|---|---|
| anti-SIRPa + SIRPv1 | 0,78 |
| anti-SIRPa + SIRPv2 | / |
| anti-SIRPa + SIRPv3 | 0,99 |
| anti-SIRPa + SIRPv4 | 0,71 |
| anti-SIRPa + SIRPv5 | 0,63 |
| anti-SIRPa + SIRPv6 | 0,72 |
| anti-SIRPa + SIRPv7 | 0,54 |
| anti-SIRPa + SIRPv8 | / |
| anti-SIRPa + Fc | / |

B)

| | ED50 (ng/ml) |
|---|---|
| Kwar23 + SIRPv1 | 0,77 |
| Kwar23 + SIRPv2 | 0,77 |
| Kwar23 + SIRPv3 | 0,77 |
| Kwar23 + SIRPv4 | 0,74 |
| Kwar23 + SIRPv5 | 0,78 |
| Kwar23 + SIRPv6 | 0,75 |
| Kwar23 + SIRPv7 | 0,60 |
| Kwar23 + SIRPv8 | 0,93 |
| Kwar23 + Fc | / |

Figure 4

| Index | Sample ID | Conc. (nM) | Information | KD (M) | ka (1/Ms) | ka Error | kd (1/s) | kd Error | Rmax | Rmax Error | R equilibrium |
|---|---|---|---|---|---|---|---|---|---|---|---|
| 1 | LSB2-20 | 133.3 | | 2.001e-8 | 7.683e5 | 2.166e4 | 1.538e-2 | 5.21e-4 | 1.404 | 0.02729 | 1.221 |
| 2 | kwar23 | 133.3 | | 1.068e-4 | 3.339e3 | 1.139e6 | 3.567e-1 | 1.048e-1 | 81.84 | 27890 | 0.102 |
| 3 | sirp29 | 133.3 | | 3.386e-5 | 4.279e3 | 1.086e5 | 1.449e-1 | 9.625e-3 | 36.06 | 914 | 0.1414 |

Figure 10 ized in Barclay, A. N. & Brown, M. H., Nat Rev Immunol 6, 457-64 (2006); see also WO 97/48723).

SEQUENCE LISTING

```
<160> NUMBER OF SEQ ID NOS: 35

<210> SEQ ID NO 1
<211> LENGTH: 7
<212> TYPE: PRT
<213> ORGANISM: artificial sequence
<220> FEATURE:
<223> OTHER INFORMATION: Epitope SIRPa v1

<400> SEQUENCE: 1

Lys Gly Ser Pro Asp Asp Val
1               5

<210> SEQ ID NO 2
<211> LENGTH: 6
<212> TYPE: PRT
<213> ORGANISM: artificial sequence
<220> FEATURE:
<223> OTHER INFORMATION: Epitope SIRPa v2

<400> SEQUENCE: 2

Lys Gly Ser Pro Asp Thr
1               5

<210> SEQ ID NO 3
<211> LENGTH: 504
<212> TYPE: PRT
<213> ORGANISM: artificial sequence
<220> FEATURE:
<223> OTHER INFORMATION: SIRPa v1 (with SP)

<400> SEQUENCE: 3

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110
```

-continued

Pro Ala Asp Ala Gly Thr Tyr Tyr Cys Val Lys Phe Arg Lys Gly Ser
115                 120                 125

Pro Asp Asp Val Glu Phe Lys Ser Gly Ala Gly Thr Glu Leu Ser Val
130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
                180                 185                 190

Asp Phe Gln Thr Asn Val Asp Pro Val Gly Glu Ser Val Ser Tyr Ser
                195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
                275                 280                 285

Glu Asn Gly Asn Val Ser Arg Thr Glu Thr Ala Ser Thr Val Thr Glu
                290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
                355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
                420                 425                 430

Asn Leu Pro Lys Gly Lys Lys Pro Ala Pro Gln Ala Ala Glu Pro Asn
                435                 440                 445

Asn His Thr Glu Tyr Ala Ser Ile Gln Thr Ser Pro Gln Pro Ala Ser
450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 4
<211> LENGTH: 11
<212> TYPE: PRT

```
<213> ORGANISM: artificial sequence
<220> FEATURE:
<223> OTHER INFORMATION: Epitope SIRPa v1 long version

<400> SEQUENCE: 4

Lys Phe Arg Lys Gly Ser Pro Asp Asp Val Glu
1               5                   10

<210> SEQ ID NO 5
<211> LENGTH: 7
<212> TYPE: PRT
<213> ORGANISM: artificial sequence
<220> FEATURE:
<223> OTHER INFORMATION: Linear epitope SIRPa v1 /1

<400> SEQUENCE: 5

Ser Leu Ile Pro Val Gly Pro
1               5

<210> SEQ ID NO 6
<211> LENGTH: 12
<212> TYPE: PRT
<213> ORGANISM: artificial sequence
<220> FEATURE:
<223> OTHER INFORMATION: Linear epitope SIRPa v1 /2

<400> SEQUENCE: 6

Gly Arg Glu Leu Ile Tyr Asn Gln Lys Glu Gly His
1               5                   10

<210> SEQ ID NO 7
<211> LENGTH: 13
<212> TYPE: PRT
<213> ORGANISM: artificial sequence
<220> FEATURE:
<223> OTHER INFORMATION: Conformational epitope SIRPa v1 /1

<400> SEQUENCE: 7

Glu Leu Ile Tyr Asn Gln Lys Glu Gly His Phe Pro Arg
1               5                   10

<210> SEQ ID NO 8
<211> LENGTH: 11
<212> TYPE: PRT
<213> ORGANISM: artificial sequence
<220> FEATURE:
<223> OTHER INFORMATION: Conformational epitope SIRPa v1 /2

<400> SEQUENCE: 8

Arg Asn Met Asp Phe Ser Ile Arg Ile Gly Asn
1               5                   10

<210> SEQ ID NO 9
<211> LENGTH: 5
<212> TYPE: PRT
<213> ORGANISM: artificial sequence
<220> FEATURE:
<223> OTHER INFORMATION: HCDR1

<400> SEQUENCE: 9

Ser Tyr Trp Val His
1               5

<210> SEQ ID NO 10
<211> LENGTH: 16
<212> TYPE: PRT
<213> ORGANISM: artificial sequence
```

```
<220> FEATURE:
<223> OTHER INFORMATION: HCDR2 1

<400> SEQUENCE: 10

Asn Ile Asp Pro Ser Asp Ser Asp Thr His Tyr Asn Gln Lys Phe Lys
1               5                   10                  15

<210> SEQ ID NO 11
<211> LENGTH: 16
<212> TYPE: PRT
<213> ORGANISM: artificial sequence
<220> FEATURE:
<223> OTHER INFORMATION: HCDR2 2

<400> SEQUENCE: 11

Asn Ile Asp Pro Ser Asp Ser Asp Thr His Tyr Ser Pro Ser Phe Gln
1               5                   10                  15

<210> SEQ ID NO 12
<211> LENGTH: 11
<212> TYPE: PRT
<213> ORGANISM: artificial sequence
<220> FEATURE:
<223> OTHER INFORMATION: HCDR3 1

<400> SEQUENCE: 12

Gly Gly Thr Gly Thr Met Ala Trp Phe Ala Tyr
1               5                   10

<210> SEQ ID NO 13
<211> LENGTH: 11
<212> TYPE: PRT
<213> ORGANISM: artificial sequence
<220> FEATURE:
<223> OTHER INFORMATION: HCDR3 2

<400> SEQUENCE: 13

Gly Gly Thr Gly Thr Leu Ala Trp Phe Ala Tyr
1               5                   10

<210> SEQ ID NO 14
<211> LENGTH: 11
<212> TYPE: PRT
<213> ORGANISM: artificial sequence
<220> FEATURE:
<223> OTHER INFORMATION: HCDR3 3

<400> SEQUENCE: 14

Gly Gly Thr Gly Thr Met Ala Tyr Phe Ala Tyr
1               5                   10

<210> SEQ ID NO 15
<211> LENGTH: 11
<212> TYPE: PRT
<213> ORGANISM: artificial sequence
<220> FEATURE:
<223> OTHER INFORMATION: HCDR3 4

<400> SEQUENCE: 15

Gly Gly Thr Gly Thr Leu Ala Tyr Phe Ala Tyr
1               5                   10

<210> SEQ ID NO 16
<211> LENGTH: 112
<212> TYPE: PRT
<213> ORGANISM: artificial sequence
<220> FEATURE:
```

<223> OTHER INFORMATION: Light chain variable domain /1

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Tyr Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Gly
                85                  90                  95

Thr His Val Pro Tyr Thr Phe Gly Gly Gly Thr Lys Val Glu Ile Lys
            100                 105                 110

<210> SEQ ID NO 17
<211> LENGTH: 112
<212> TYPE: PRT
<213> ORGANISM: artificial sequence
<220> FEATURE:
<223> OTHER INFORMATION: Light chain variable domain /2

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Tyr Gly Asn Thr Tyr Leu Tyr Trp Phe Gln Gln Arg Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Thr His Val Pro Tyr Thr Phe Gly Gly Gly Thr Lys Val Glu Ile Lys
            100                 105                 110

<210> SEQ ID NO 18
<211> LENGTH: 120
<212> TYPE: PRT
<213> ORGANISM: artificial sequence
<220> FEATURE:
<223> OTHER INFORMATION: Heavy chain variable domain /1

<400> SEQUENCE: 18

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr

```
                65                  70                  75                  80
Leu Gln Leu Ser Ser Leu Lys Ala Ser Asp Thr Ala Met Tyr Tyr Cys
                    85                  90                  95

Val Arg Gly Gly Thr Gly Thr Leu Ala Trp Phe Ala Tyr Trp Gly Gln
                100                 105                 110

Gly Thr Leu Val Thr Val Ser Ser
                115                 120
```

<210> SEQ ID NO 19
<211> LENGTH: 120
<212> TYPE: PRT
<213> ORGANISM: artificial sequence
<220> FEATURE:
<223> OTHER INFORMATION: Heavy chain variable domain /2

<400> SEQUENCE: 19

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                    85                  90                  95

Val Arg Gly Gly Thr Gly Thr Met Ala Tyr Phe Ala Tyr Trp Gly Gln
                100                 105                 110

Gly Thr Leu Val Thr Val Ser Ser
                115                 120
```

<210> SEQ ID NO 20
<211> LENGTH: 120
<212> TYPE: PRT
<213> ORGANISM: artificial sequence
<220> FEATURE:
<223> OTHER INFORMATION: Heavy chain variable domain /3

<400> SEQUENCE: 20

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
                20                  25                  30

Trp Val His Trp Val Arg Gln Met Pro Gly Lys Gly Leu Glu Trp Met
            35                  40                  45

Gly Asn Ile Asp Pro Ser Asp Ser Asp Thr His Tyr Ser Pro Ser Phe
    50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                    85                  90                  95

Val Arg Gly Gly Thr Gly Thr Leu Ala Tyr Phe Ala Tyr Trp Gly Gln
                100                 105                 110

Gly Thr Leu Val Thr Val Ser Ser
                115                 120
```

```
<210> SEQ ID NO 21
<211> LENGTH: 120
<212> TYPE: PRT
<213> ORGANISM: artificial sequence
<220> FEATURE:
<223> OTHER INFORMATION: Heavy chain variable domain /4

<400> SEQUENCE: 21

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Val His Trp Val Arg Gln Met Pro Gly Lys Gly Leu Glu Trp Ile
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: artificial sequence
<220> FEATURE:
<223> OTHER INFORMATION: Heavy chain variable domain /5

<400> SEQUENCE: 22

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
        35                  40                  45

Gly Asn Ile Asp Pro Ser Asp Ser Asp Thr His Tyr Asn Gln Lys Phe
    50                  55                  60

Lys Asp His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ser
        115                 120

<210> SEQ ID NO 23
<211> LENGTH: 120
<212> TYPE: PRT
<213> ORGANISM: artificial sequence
<220> FEATURE:
<223> OTHER INFORMATION: Heavy chain variable domain /6

<400> SEQUENCE: 23

Glu Val Gln Leu Val Gln Ser Gly Ala Glu Val Lys Lys Pro Gly Glu
```

```
1               5                   10                  15
Ser Leu Arg Ile Ser Cys Lys Ala Ser Gly Tyr Ser Phe Thr Ser Tyr
            20                  25                  30

Trp Val His Trp Val Arg Gln Met Pro Gly Lys Gly Leu Glu Trp Met
            35                  40                  45

Gly Asn Ile Asp Pro Ser Ser Asp Thr His Tyr Ser Pro Ser Phe
            50                  55                  60

Gln Gly His Val Thr Leu Ser Val Asp Lys Ser Ile Ser Thr Ala Tyr
65                  70                  75                  80

Leu Gln Leu Ser Ser Leu Lys Ala Ser Asp Thr Ala Met Tyr Tyr Cys
                85                  90                  95

Val Arg Gly Gly Thr Gly Thr Met Ala Trp Phe Ala Tyr Trp Gly Gln
                100                 105                 110

Gly Thr Leu Val Thr Val Ser Ser
            115                 120

<210> SEQ ID NO 24
<211> LENGTH: 474
<212> TYPE: PRT
<213> ORGANISM: artificial sequence
<220> FEATURE:
<223> OTHER INFORMATION: SIRPa V1 (without SP)

<400> SEQUENCE: 24

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
            50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser Ala Pro Val Val Ser Gly Pro Ala Ala
            115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
                180                 185                 190

His Ser Gln Val Ile Cys Glu Val Ala His Val Thr Leu Gln Gly Asp
            195                 200                 205

Pro Leu Arg Gly Thr Ala Asn Leu Ser Glu Thr Ile Arg Val Pro Pro
            210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
```

```
                    245                 250                 255
Trp Leu Glu Asn Gly Asn Val Ser Arg Thr Glu Thr Ala Ser Thr Val
                260                 265                 270

Thr Glu Asn Lys Asp Gly Thr Tyr Asn Trp Met Ser Trp Leu Leu Val
            275                 280                 285

Asn Val Ser Ala His Arg Asp Asp Val Lys Leu Thr Cys Gln Val Glu
        290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ile Val Val Gly Val Val Cys Thr Leu
            340                 345                 350

Leu Val Ala Leu Leu Met Ala Ala Leu Tyr Leu Val Arg Ile Arg Gln
        355                 360                 365

Lys Lys Ala Gln Gly Ser Thr Ser Ser Thr Arg Leu His Glu Pro Glu
    370                 375                 380

Lys Asn Ala Arg Glu Ile Thr Gln Asp Thr Asn Asp Ile Thr Tyr Ala
385                 390                 395                 400

Asp Leu Asn Leu Pro Lys Gly Lys Lys Pro Ala Pro Gln Ala Ala Glu
                405                 410                 415

Pro Asn Asn His Thr Glu Tyr Ala Ser Ile Gln Thr Ser Pro Gln Pro
            420                 425                 430

Ala Ser Glu Asp Thr Leu Thr Tyr Ala Asp Leu Asp Met Val His Leu
        435                 440                 445

Asn Arg Thr Pro Lys Gln Pro Ala Pro Lys Pro Glu Pro Ser Phe Ser
    450                 455                 460

Glu Tyr Ala Ser Val Gln Val Pro Arg Lys
465                 470

<210> SEQ ID NO 25
<211> LENGTH: 16
<212> TYPE: PRT
<213> ORGANISM: artificial sequence
<220> FEATURE:
<223> OTHER INFORMATION: Epitope SIRPa v1 right

<400> SEQUENCE: 25

Asp Asp Val Glu Phe Lys Ser Gly Ala Gly Thr Glu Leu Ser Val Arg
1               5                   10                  15

<210> SEQ ID NO 26
<211> LENGTH: 4201
<212> TYPE: DNA
<213> ORGANISM: artificial sequence
<220> FEATURE:
<223> OTHER INFORMATION: cDNA complete SIRPa v1

<400> SEQUENCE: 26
tccggcccgc acccaccccc aagagggggcc ttcagctttg ggctcagag gcacgacctc    60 ctggggaggg ttaaaaggca gacgcccccc cgccccccgc gccccgcgc cccgactcct   120 tcgccgcctc cagcctctcg ccagtgggaa gcggggagca gccgcgcggc cggagtccgg   180
aggcgagggg aggtcggccg caacttcccc ggtccacctt aagaggacga tgtagccagc   240
tcgcagcgct gacctcagaa aaacaagttt gcgcaaagtg gagcggggac ccggcctctg   300
ggcagccccg gcggcgcttc cagtgccttc cagccctcgc gggcggcgca gccgcggccc   360
```

-continued

| | |
|---|---|
| atggagcccg ccggcccggc ccccggccgc ctcgggccgc tgctctgcct gctgctcgcc | 420 |
| gcgtcctgcg cctggtcagg agtggcgggt gaggaggagc tgcaggtgat tcagcctgac | 480 |
| aagtccgtgt tggttgcagc tggagagaca gccactctgc gctgcactgc gacctctctg | 540 |
| atccctgtgg ggcccatcca gtggttcaga ggagctggac caggccggga attaatctac | 600 |
| aatcaaaaag aaggccactt cccccgggta caactgtttt cagacctcac aaagagaaac | 660 |
| aacatggact tttccatccg catcggtaac atcaccccag cagatgccgg cacctactac | 720 |
| tgtgtgaagt tccggaaagg gagccccgat gacgtggagt ttaagtctgg agcaggcact | 780 |
| gagctgtctg tgcgcgccaa accctctgcc ccgtggtat cgggccctgc ggcgagggcc | 840 |
| acacctcagc acacagtgag cttcacctgc gagtcccacg gcttctcacc cagagacatc | 900 |
| accctgaaat ggttcaaaaa tgggaatgag ctctcagact ccagaccaa cgtggacccc | 960 |
| gtaggagaga gcgtgtccta cagcatccac agcacagcca aggtggtgct gacccgcgag | 1020 |
| gacgttcact ctcaagtcat ctgcgaggtg gcccacgtca ccttgcaggg ggaccctctt | 1080 |
| cgtgggactg ccaacttgtc tgagaccatc cgagttccac ccaccttgga ggttactcaa | 1140 |
| cagcccgtga gggcagagaa ccaggtgaat gtcacctgcc aggtgaggaa gttctacccc | 1200 |
| cagagactac agctgacctg gttggagaat ggaaacgtgt cccggacaga aacggcctca | 1260 |
| accgttacag agaacaagga tggtacctac aactggatga gctggctcct ggtgaatgta | 1320 |
| tctgcccaca gggatgatgt gaagctcacc tgccaggtgg agcatgacgg gcagccagcg | 1380 |
| gtcagcaaaa gccatgacct gaaggtctca gcccacccga aggagcaggg ctcaaatacc | 1440 |
| gccgctgaga cactggatc taatgaacgg aacatctata ttgtggtggg tgtggtgtgc | 1500 |
| accttgctgg tggccctact gatggcggcc ctctacctcg tccgaatcag acagaagaaa | 1560 |
| gcccagggct ccacttcttc tacaaggttg catgagcccg agaagaatgc cagagaaata | 1620 |
| acacaggaca caaatgatat cacatatgca gacctgaacc tgcccaaggg gaagaagcct | 1680 |
| gctcccagg ctgcggagcc caacaaccac acggagtatg ccagcattca gaccagcccg | 1740 |
| cagcccgcgt cggaggacac cctcacctat gctgacctgg acatggtcca cctcaaccgg | 1800 |
| accccccaagc agccggcccc caagcctgag ccgtccttct cagagtacgc cagcgtccag | 1860 |
| gtcccgagga agtgaatggg accgtggttt gctctagcac ccatctctac gcgctttctt | 1920 |
| gtcccacagg gagccgccgt gatgagcaca gccaacccag ttcccggagg ctggggcgg | 1980 |
| tgcaggctct gggacccagg ggccagggtg gctcttctct cccaccccct ccttggctct | 2040 |
| ccagcacttc ctgggcagcc acggcccccct cccccacat tgccacatac ctggaggctg | 2100 |
| acgttgccaa accagccagg gaaccaacct gggaagtggc cagaactgcc tggggtccaa | 2160 |
| gaactcttgt gcctccgtcc atcaccatgt gggttttgaa gacccgac tgcctccccg | 2220 |
| atgctccgaa gcctgatctt ccagggtggg gaggagaaaa tcccacctcc cctgacctcc | 2280 |
| accacctcca ccaccaccac caccaccacc accaccacta ccaccaccac ccaactgggg | 2340 |
| ctagagtggg gaagatttcc cctttagatc aaactgcccc ttccatggaa aagctggaaa | 2400 |
| aaaactctgg aacccatatc caggcttggt gaggttgctg ccaacagtcc tggcctcccc | 2460 |
| catccctagg ctaaagagcc atgagtcctg gaggaggaga ggacccctcc caaaggactg | 2520 |
| gagacaaaac cctctgcttc cttgggtccc tccaagactc cctggggccc aactgtgttg | 2580 |
| ctccacccgg acccatctct cccttctaga cctgagcttg cccctccagc tagcactaag | 2640 |
| caacatctcg ctgtggacgc ctgtaaatta ctgagaaatg tgaaacgtgc aatcttgaaa | 2700 |
| ctgaggtgtt agaaaacttg atctgtggtg ttttgtttg ttttttttct taaaacaaca | 2760 |

-continued

```
gcaacgtgat cttggctgtc tgtcatgtgt tgaagtccat ggttgggtct tgtgaagtct    2820
gaggtttaac agtttgttgt cctggaggga ttttcttaca gcaagacttt gagttcctcc    2880
aagtcccaga accccaagaa tgggcaagaa ggatcaggtc agccactccc tggagacaca    2940
gccttctggc tgggactgac ttggccatgt tctcagctga ccacgcggc tggtagtgca     3000 gccttctgtg accccgctgt ggtaagtcca gcctgcccag gctgctgagg gctgcctct     3060 tgacagtgca gtcttatcga gacccaatgc ctcagtctgc tcatccgtaa agtggggata    3120
gtgaagatga caccctccc caccacctct cataagcact ttaggaacac acagagggta     3180
gggatagtgg ccctggccgt ctatcctacc cctttagtga ccgcccccat cccggctttc    3240
tgagctgatc cttgaagaag aaatcttcca tttctgctct caaaccctac tgggatcaaa    3300
ctggaataaa ttgaagacag ccaggggggat ggtgcagctg tgaagctcgg gctgattccc   3360
cctctgtccc agaaggttgg ccagagggtg tgacccagtt acccttaac ccccacccttt    3420 ccagtcgggt gtgagggcct gaccgggccc agggcaagca gatgtcgcaa gccctattta    3480
ttcagtcttc actataactc ttagagttga gacgctaatg ttcatgactc ctggccttgg    3540
gatgcccaag ggatttctgg ctcaggctgt aaaagtagct gagccatcct gcccattcct    3600
ggaggtccta caggtgaaac tgcaggagct cagcatagac ccagctctct gggggatggt    3660
cacctggtga tttcaatgat ggcatccagg aattagctga ccaacagac catgtggaca     3720 gctttggcca gagctcccgt gtggcatctg ggagccacag tgacccagcc acctggctca    3780
ggctagttcc aaattccaaa agattggctt gtaaaccttc gtctccctct cttttaccca    3840
gagacagcac atacgtgtgc acacgcatgc acacacacat tcagtatttt aaaagaatgt    3900
tttcttggtg ccatttcat tttattttat tttttaattc ttggaggggg aaataaggga     3960
ataaggccaa ggaagatgta tagctttagc tttagcctgg caacctggag aatccacata    4020
ccttgtgtat tgaaccccag gaaaaggaag aggtcgaacc aacccctgcgg aaggagcatg   4080 gtttcaggag tttattttaa gactgctggg aaggaaacag gccccatttt gtatatagtt    4140
gcaacttaaa cttttggct tgcaaaatat ttttgtaata aagatttctg ggtaataatg     4200
a                                                                   4201
```

<210> SEQ ID NO 27
<211> LENGTH: 357
<212> TYPE: DNA
<213> ORGANISM: artificial sequence
<220> FEATURE:
<223> OTHER INFORMATION: cDNA exon 3 SIRPa v1

<400> SEQUENCE: 27

```
gagtggcggg tgaggaggag ctgcaggtga ttcagcctga caagtccgtg ttggttgcag     60
ctggagagac agccactctg cgctgcactg cgacctctct gatccctgtg gggcccatcc    120
agtggttcag aggagctgga ccaggccggg aattaatcta caatcaaaaa gaaggccact    180 tccccccgggt aacaactgtt tcagacctca caaagagaaa caacatggac ttttccatcc    240
gcatcggtaa catcaccccca gcagatgccg gcacctacta ctgtgtgaag ttccggaaag    300
ggagccccga tgacgtggag tttaagtctg gagcaggcac tgagctgtct gtgcgcg       357
```

<210> SEQ ID NO 28
<211> LENGTH: 503
<212> TYPE: PRT
<213> ORGANISM: artificial sequence
<220> FEATURE:

<223> OTHER INFORMATION: SIRPa v2 (with SP)

<400> SEQUENCE: 28

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Val Thr Glu Asn
    290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400
```

-continued

```
Gln Gly Ser Thr Ser Ser Thr Arg Leu His Glu Pro Glu Lys Asn Ala
            405                 410                 415

Arg Glu Ile Thr Gln Asp Thr Asn Asp Ile Thr Tyr Ala Asp Leu Asn
        420                 425                 430

Leu Pro Lys Gly Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500
```

<210> SEQ ID NO 29
<211> LENGTH: 10
<212> TYPE: PRT
<213> ORGANISM: artificial sequence
<220> FEATURE:
<223> OTHER INFORMATION: Epitope SIRPa v2 long version

<400> SEQUENCE: 29

```
Lys Phe Arg Lys Gly Ser Pro Asp Thr Glu
1               5                   10
```

<210> SEQ ID NO 30
<211> LENGTH: 14
<212> TYPE: PRT
<213> ORGANISM: artificial sequence
<220> FEATURE:
<223> OTHER INFORMATION: Epitope SIRPa v2 right

<400> SEQUENCE: 30

```
Thr Glu Phe Lys Ser Gly Ala Gly Thr Glu Leu Ser Val Arg
1               5                   10
```

<210> SEQ ID NO 31
<211> LENGTH: 355
<212> TYPE: DNA
<213> ORGANISM: artificial sequence
<220> FEATURE:
<223> OTHER INFORMATION: cDNA exon 3 SIRPa v2

<400> SEQUENCE: 31

```
gagtggcggg tgaggaggag ctgcaggtga ttcagcctga caagtccgta tcagttgcag    60
ctggagagtc ggccattctg cactgcactg tgacctccct gatccctgtg gggcccatcc   120
agtggttcag aggagctgga ccagcccggg aattaatcta caatcaaaaa gaaggccact   180
tcccccgggt aacaactgtt tcagagtcca caaagagaga aacatggact tttccatca   240 gcatcagtaa catcacccca gcagatgccg gcacctacta ctgtgtgaag ttccggaaag   300
ggagccctga cacggagttt aagtctggag caggcactga gctgtctgtg cgtgc        355
```

<210> SEQ ID NO 32
<211> LENGTH: 180
<212> TYPE: PRT
<213> ORGANISM: artificial sequence
<220> FEATURE:
<223> OTHER INFORMATION: SIRPa human variant 1

<400> SEQUENCE: 32

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile
            180

<210> SEQ ID NO 33
<211> LENGTH: 179
<212> TYPE: PRT
<213> ORGANISM: artificial sequence
<220> FEATURE:
<223> OTHER INFORMATION: SIRPa human variant 2

<400> SEQUENCE: 33

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Val Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile

<210> SEQ ID NO 34
<211> LENGTH: 179
<212> TYPE: PRT
<213> ORGANISM: artificial sequence
<220> FEATURE:
<223> OTHER INFORMATION: SIRPb human

<400> SEQUENCE: 34

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile

<210> SEQ ID NO 35
<211> LENGTH: 178
<212> TYPE: PRT
<213> ORGANISM: artificial sequence
<220> FEATURE:
<223> OTHER INFORMATION: SIRPg human /1

<400> SEQUENCE: 35

Met Pro Val Pro Ala Ser Trp Pro His Pro Pro Gly Pro Phe Leu Leu
1               5                   10                  15

Leu Thr Leu Leu Leu Gly Leu Thr Glu Val Ala Gly Glu Glu Glu Leu
            20                  25                  30

Gln Met Ile Gln Pro Glu Lys Leu Leu Leu Val Thr Val Gly Lys Thr
        35                  40                  45

Ala Thr Leu His Cys Thr Val Thr Ser Leu Leu Pro Val Gly Pro Val
    50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
            100                 105                 110

Asp Val Gly Thr Tyr Tyr Cys Val Lys Phe Arg Lys Gly Ser Pro Glu

```
            115                 120                 125
Asn Val Glu Phe Lys Ser Gly Pro Gly Thr Glu Met Ala Leu Gly Ala
        130                 135             140

Lys Pro Ser Ala Pro Val Val Leu Gly Pro Ala Ala Arg Thr Thr Pro
145                     150                 155                 160

Glu His Thr Val Ser Phe Thr Cys Glu Ser His Gly Phe Ser Pro Arg
                165                 170                 175

Asp Ile
```

USE OF ANTI-HUMAN SIRPA V1 ANTIBODIES AND METHOD FOR PRODUCING ANTI-SIRPA V1 ANTIBODIES

CROSS-REFERENCE TO RELATED APPLICATIONS

This patent application is a U.S. National Phase application under 35 U.S.C. § 371 of PCT/EP2019/056250, filed on March 13, 2019, claiming the benefit of European Patent Application No. 18305271.1, filed on March 13, 2018, both of which are incorporated herein by reference in their entireties.

The invention is in the field of immunotherapy. The present invention provides antibodies useful in therapeutic and diagnostic applications targeting human SIRPa, said antibodies enhancing the cross-presentation of antigens to T cells. The invention also provides antibodies against specific isoforms of SIRPa and able to disrupt the interaction between those isoforms of SIRPa and human CD47 for use in treating or preventing a disease, or in diagnostic applications. The invention also relates to methods for producing and/or selecting anti-human SIRPa antibodies that bind with different affinities to various isoforms of human SIRP members.

BRIEF DESCRIPTION OF THE PRIOR ART

Targeting immune checkpoints of the adaptive immunity has shown great therapeutic efficacy to fight numerous cancers. Immune checkpoints on myeloid cells like macrophages, dendritic cells (DC), myeloid-derived suppressor cells (MDSCs), and polymorphonuclear leukocytes or neutrophils (PMN), remain poorly studied while these cells represent the most abundant immune cell type in many solid tumors and are often associated with a poor outcome.

Signal regulatory protein alpha (SIRPa, also designated SIRP-alpha, SIRPα, CD172a or SHPS-1), is expressed on monocytes, most subpopulations of tissue macrophages, granulocytes, subset of DC in lymphoid tissues, some bone marrow progenitor cells, and to varying levels on neurons, with a notably expression in synapse-rich areas of the brain, such as the granular layer of the cerebellum and the hippocampus.

SIRPa is the prototypic member of the SIRP paired receptor family of closed related SIRP proteins comprising SIRPa, SIRPg (also designated SIRP-gamma, SIRPγ, CD172g or SIRP beta-2) and SIRPb (also designated SIRP-beta, SIRPβ, CD172b). Signal regulatory proteins (SIRPs) constitute a family of cell surface glycoproteins which are expressed on myeloid (including macrophages, granulocytes, myeloid dendritic cells, and mast cells) and neuronal cells (summarized in Barclay, A. N. & Brown, M. H., Nat Rev Immunol 6, 457-64 (2006); see also WO 97/48723). CD47, a broadly expressed transmembrane glycoprotein, functions as a cellular ligand for SIRPa and binds to the $NH_2$-terminal extracellular terminus of SIRPa. SIRPa's role has been best documented in respect of its inhibitory role in the phagocytosis of host cells by macrophages. In particular, the binding of SIRPa on macrophages by CD47 expressed on target cells, generates an inhibitory signal that negatively regulates phagocytosis. However, more recent findings have also demonstrated additional positive signaling effects mediated through SIRPa binding (Shultz, L. D. et al. (1995) J Immunol 154, 180-91).

The gene coding for SIRPa is a polymorphic gene and several variants are described in human populations. The most common human SIRPa variants are SIRPa v1 and SIRPa v2 (accession number NP_542970 (P78324) and CAA71403 respectively), and the SIRPa family is usually divided into these two subsets; namely the SIRPa v1 isoform family and the SIRPa v2 isoform family.

Expressed by myeloid cells, SIRPa interacts with the ubiquitous receptor CD47, and this interaction is an important immune checkpoint of the innate response, involved in the regulation of myeloid functions. The interaction between SIRPa and CD47 provides a down-regulatory signal that inhibits host cell phagocytosis. Since CD47 is widely overexpressed in some cancer cells, CD47 functions as a "don't eat me" signal within some tumor comprising these cells, thereby avoiding phagocytosis. The potential contribution of CD47-SIRPa interaction in cancer cell clearance has been intensely investigated in recent years. It was shown that abundance of CD47 receptors in tumors is inversely correlated with patient overall survival and constitute an adverse prognostic factor for several cancer types.

The SIRPa/CD47 pathway has therefore been subject to different pharmaceutical developments to enhance macrophages phagocytosis. A variety of approaches have been proposed to disrupt the CD47/SIRPa interaction in an effort to effect a biological outcome. These encompass the use of fragmented/truncated SIRPa and/or CD47 proteins and antibodies thereto. Over-expression of CD47 by cancer cells renders them resistant to macrophages, even when these cells are coated with therapeutic antibodies. The blockade of SIRPa/CD47 pathway via agents targeting CD47 has shown to enhance the antibody-dependent phagocytosis by macrophages. These therapies have also been described to synergize with depleting therapeutic anticancer antibodies such as Trastuzumab (anti-Her2), Cetuximab (anti-EGFR), Rituximab (anti-Cd20) and Alemtuzumab (anti-CD52).

Nonetheless, it has recently been shown that anti-CD47 agents present hematological toxicity related to CD47 physiological role. As examples, these anti-CD47 agents may cause anemia or thrombocytopenia. Moreover, CD47 is also involved in other pathways with other members of the SIRP family. Indeed, CD47 also engages with SIRPg present at the surface of human T cells, but not on human myeloid cells. SIRPg/CD47 interaction mediates cell-cell adhesion, enhances superantigen-dependent T-cell-mediated proliferation and costimulates T-cell activation (Piccio et al., 2005).

Therefore, anti-human SIRP antibodies able to bind only one kind of SIRP and able to disrupt the binding of CD47 to SIRPa have been developed in recent years to avoid undesirable effects such as an inhibition of the proliferation of T cells. Unfortunately, due to the nature of the SIRPa family of proteins, the antibodies of the prior art may not be efficient for treating a disease wherein SIRPa is involved when the SIRPa proteins expressed by the cells of the patient is SIRPa v1 or SIRPa v2. Some antibodies may be useful for treating SIRPa v1-patients, but may present a reduced therapeutic function for treating SIRPa v2 patients, or the opposite. Since the treatment of some cancer is deeply related to the phenotype of a patient, there is a need for antibodies directed to the isoforms expressed by the cells of each patient. Therefore, there is still a need in the prior art for new and improved agents, in particular antibodies, targeting SIRPa with a higher specificity. There is also a need for a method for producing such specific antibodies, method for selecting these antibodies, and method for determining if a patient is likely to respond to a treatment with an anti-human SIRPa antibody before receiving such treatment.

There is also a need in the art to enhance cross-presentation of antigen by Antigen Presenting Cells (APCs). APCs, in particular dendritic cells, play unique and diverse roles in tumor occurrence, development of a disease, progression of a disease and response to a therapy. As an example, dendritic cells actively uptake tumor-associated antigens, process them and present antigenic peptides to T cells, thereby inducing and maintaining tumor-specific T cells responses. Dendritic cells (DCs) are also called professional APCs. The dendritic cells interaction with different immune effector cells may also support the innate antitumor immunity, as well as humoral response also known to inhibit tumor development in certain cases. On the other hand, DCs are recruited to the tumor site by specific tumor-derived and stroma-derived factors, which may impair their maturation, their differentiation and/or their function, thus resulting in a deficient formation of anti-tumor immune response, or the development of a dendritic cells-mediated tolerance and immune suppression. Identification of DC-stimulating and DC-suppressing/polarizing factors in the tumor environment and the mechanism of DC modulation are important for designing effective DC-based vaccines and for recovery of immunodeficient resident DCs responsible for maintenance of clinically relevant antitumor immunity in patients with cancer (Zong et al., 2016). Dendritic cells SIRPa negative are described as being the most potent APCs for cross-presentation of antigens in mouse and human. DCs SIRPa positive are known for being less efficient in cross-presentation (Meral et al., 2013; Nierkens et al., 2015; Segura et al., 2015)

Cancer cells express tumor antigens, including neoantigens generated by non-synonymous mutations, but are poor for antigen presentation. The recovery of immunodeficient resident Dendritic Cells responsible for maintenance of clinically relevant antitumor immunity in patients with cancer is an important therapeutic item to consider. Enhancing cross presentation of Tumor antigens or mutated antigens present in specific cancers with an antibody would be of major interest for treating or preventing some diseases, including cancers. The CD47/SIRPa signaling pathway may be of interest for modulating the cross-presentation of antigen to T cells (Criscitiello, 2012; Ilyas and Yang, 2015; Vigneron, 2015).

Defect in antigen presentation represents a major immune escape mechanism in cancer and downregulation/loss of the antigen presentation is a major immune escape mechanism in cancer (Sanchez-Paulete et al., 2017). Therefore, there is a need for a product that would enhance the cross-presentation of antigen when used. PCT/EP/2017/059071 patent application describes new anti-SIRPa antibodies able to specifically decrease the interaction between SIRPa and CD47 without affecting the interaction between SIRPg and CD47. WO201356352 patent publication describes the selection of an anti-SIRPa antibody (SIRP29) from a phage display library called Library F which was used in order to select binders to SIRPa v1 and v2 and negative for SIRPb and SIRPg. The antibody disclosed therein is able to recognize both variants in the population. Also, the inventors of the present invention did show that the SIRP29 antibody is in fact able to bind SIRPg and disrupt the SIRPg-CD47 interaction.

WO2015138600 patent publication provides compositions and methods related to anti-SIRPa antibodies. The antibodies of this disclosure bind to human SIRPa and can block the interaction of CD47 expressed on a target cell of interest with SIRPa expressed on a phagocytic cell. The subject antibodies find use in various therapeutic methods. In some cases, the anti-SIRPa antibodies can bind to SIRPa but do not stimulate SIRPa signaling in the cell expressing the SIRPa. Furthermore, the antibodies described therein are able to bind SIRPg and block the interaction between CD47 and SIRPg.

Therefore, the antibodies described in the prior art lack discriminative ability between the various members of the SIRP family, and there is a need for more specific antibodies, in particular for their use to prevent or treat several diseases.

DESCRIPTION OF THE INVENTION

In an aspect, there is provided therein an anti-human SIRPa antibody, or antigen-binding fragment thereof or antigen-binding antibody mimetic or modified antibody, for use in the treatment of a condition wherein the patient receiving the treatment is SIRPa v1-positive (i.e. is either homozygous for the SIRPa allele (v1/v1) or heterozygous for the SIRPa allele (v1/v2).

In a particular embodiment, it is provided anti-human SIRPa antibody or antigen-binding fragment thereof or antigen-binding antibody mimetic or modified antibody, which comprises:

a heavy chain variable domain comprising HCDR1, HCDR2 and HCDR3,
wherein:
HCDR1 comprises or consists of the amino acid sequence set forth in SEQ ID No: 9,
HCDR2 comprises or consists of the amino acid sequence set forth in SEQ ID No: 10 or SEQ ID No: 11, in particular HCDR2 comprises or consists of the amino acid sequence set forth in SEQ ID No: 11;
HCDR3 comprises or consists of the amino acid sequence set forth in SEQ ID No: 12, or SEQ ID No: 13, or SEQ ID No: 14 or SEQ ID No: 15; in particular HCDR3 comprises or consists of the amino acid sequence set forth in SEQ ID No: 13, or SEQ ID No: 14 or SEQ ID No: 15, in particular HCDR3 comprises or consists of the amino acid sequence set forth in SEQ ID No: 15;
and
a light chain variable domain comprising or consisting of the amino acid sequence selected from the group consisting of SEQ ID No: 16 and SEQ ID No: 17; in particular a light chain variable domain comprising or consisting of the amino acid sequence of SEQ ID No: 17;
wherein the anti-human SIRPa antibody or antigen-binding fragment thereof or antigen-binding antibody mimetic inhibits the binding of human CD47 to human SIRPa v1 and does not prevent or inhibit the binding of human CD47 to human SIRPa v2;
for use in the prevention and/or treatment of a disease in a subject that is SIRPa v1 positive.

In a further embodiment, it is also provided an antibody, an antigen-binding fragment thereof, an antigen-binding antibody mimetic or a modified antibody, which:
binds specifically to human SIRPa v1 and/or human SIRPa v2, in particular to human SIRPa v1 and human SIRPa v2, and which inhibits the binding of human CD47 to human SIRPa v1 and/or human SIRPa v2 respectively, in particular which inhibits the binding of human CD47 to human SIRPa v1 and human SIRPa v2;
does not prevent or inhibit the binding of human CD47 to human SIRPg; and in particular does not bind specifically to human SIRPg;
for use in the treatment or the prevention of a disease, in particular a cancer, or for use in therapeutic vaccination against a disease, in particular against a cancer, wherein the antibody, antigen-binding fragment thereof, antigen-binding antibody mimetic or modified antibody, enhances cross-presentation of an antigen expressed in said disease, in particular a cancer and is involved in eliciting a T cell response suitable for the treatment of said disease.

In a particular embodiment, the antibody, antigen-binding fragment thereof, antigen-binding antibody mimetic or modified antibody for use according to the present invention binds specifically to human SIRPa v1, and inhibits the binding of human CD47 to SIRPa v1. Such an antibody, antigen-binding fragment thereof, antigen-binding antibody mimetic or modified antibody for use according to the present invention is particularly suitable for the treatment or the prevention a disease, in particular a cancer, or for use in therapeutic vaccination against a disease, in particular against a cancer, in a SIRPa v1-positive patient.

The invention also provides an antibody, an antigen-binding fragment thereof, an antigen-binding antibody mimetic or a modified antibody, which comprises:
- a heavy chain variable domain comprising HCDR1, HCDR2 and HCDR3, wherein:
  HCDR1 comprises or consists of the amino acid sequence set forth in SEQ ID No: 9,
  HCDR2 comprises or consists of the amino acid sequence set forth in SEQ ID No: 10 or SEQ ID No: 11, in particular HCDR2 comprises or consists of the amino acid sequence set forth in SEQ ID No: 11;
  HCDR3 comprises or consists of the amino acid sequence set forth in SEQ ID No: 12, or SEQ ID No: 13, or SEQ ID No: 14 or SEQ ID No: 15; in particular HCDR3 comprises or consists of the amino acid sequence set forth in SEQ ID No: 13, or SEQ ID No: 14 or SEQ ID No: 15, in particular HCDR3 comprises or consists of the amino acid sequence set forth in SEQ ID No: 15; and
- a light chain variable domain comprising or consisting of the amino acid sequence selected from the group consisting of SEQ ID No: 16 and SEQ ID No: 17; in particular a light chain variable domain comprising or consisting of the amino acid sequence of SEQ ID No: 17;
- which enhances the cross-presentation of an antigen, in particular a cancer antigen, by Antigen Presenting Cells, in particular by dendritic cells, to human T cells, in particular to human CD8+ T cells;
- for use in the treatment or the prevention of a disease, in particular a cancer, or for use in therapeutic vaccination against a disease, in particular against a cancer, wherein the antibody, antigen-binding fragment thereof, antigen-binding antibody mimetic or modified antibody, enhances cross-presentation of an antigen expressed in said disease, in particular a cancer, and is involved in eliciting a T cell response suitable for the treatment of said disease.

In a particular embodiment of the invention, the antibody or antigen binding fragment thereof or antigen-binding antibody mimetic or modified antibody for use in the prevention and/or treatment of a disease, in particular for specific diseases as described herein, comprises a heavy chain variable domain comprising or consisting of the amino acid sequence selected from the group consisting of SEQ ID No: 18; SEQ ID No: 19; SEQ ID No: 20, SEQ ID No: 21; SEQ ID No: 22 and SEQ ID No: 23; in particular the heavy chain variable domain comprises or consists of the amino acid sequence of SEQ ID No: 20.

An "anti-human SIRPa v1 antibody" is an antibody that exhibits appreciable binding affinity for SIRPa v1 and which may not exhibit appreciable binding affinity for human SIRPa v2 and/or human SIRPg, binding affinity being in each case detectable by methods known in the art like but not limited to Biacore analysis, Blitz analysis, ELISA assay or Scatchard plot. An "anti-SIRPa v1 antibody" may also be defined as an antibody that exhibits appreciable binding affinity for SIRPa v1 and that blocks the interaction between human CD47 and human SIRPa v1, and which does not block the interaction between human CD47 and human SIRPa v2, and in a preferred embodiment which does not block the interaction between human CD47 and human SIRPg. By "block the interaction" it should be understood that the antibody has an antagonist effect on the CD47/SIRPa v1 interaction. Use in the negative form, this term means that the antibody does not have an antagonist effect on the CD47/SIRPa v2 interaction, and in a preferred embodiment which additionally does not have an antagonist effect on the CD47/SIRPg interaction.

As used herein, the term "antibody" refers to any kind of antibodies, such as monoclonal antibodies, polyclonal antibodies, recombinant antibodies, chimeric antibodies and humanized antibodies.

The antibodies of the present invention include monoclonal and polyclonal antibodies. As used herein, a "monoclonal antibody" is intended to refer to a preparation of antibody molecules, antibodies which share a common heavy chain and common light chain amino acid sequence, in contrast with "polyclonal" antibody preparations which contain a mixture of antibodies of different amino acid sequence. Monoclonal antibodies can be generated by several known technologies like phage, bacteria, yeast or ribosomal display, as well as by classical methods exemplified by hybridoma-derived antibodies. Thus, the term "monoclonal" is used to refer to all antibodies derived from one nucleic acid clone.

The antibodies of the present invention include recombinant antibodies. As used herein, the term "recombinant antibody" refers to antibodies which are produced, expressed, generated or isolated by recombinant means, such as antibodies which are expressed using a recombinant expression vector transfected into a host cell; antibodies isolated from a recombinant combinatorial antibody library; antibodies isolated from an animal (e.g. a mouse) which is transgenic due to human immunoglobulin genes; or antibodies which are produced, expressed, generated or isolated in any other way in which particular immunoglobulin gene sequences (such as human immunoglobulin gene sequences) are assembled with other DNA sequences. Recombinant antibodies include, for example, chimeric and humanized antibodies.

The antibodies of the present invention include chimeric antibodies. As used herein, a "chimeric antibody" refers to an antibody in which the sequence of the variable domain derived from the germline of a mammalian species, such as a mouse, have been grafted onto the sequence of the constant domain derived from the germline of another mammalian species, such as a human.

The antibodies of the present invention include humanized antibodies. As used herein, a "humanized antibody" refers to an antibody in which CDR sequences derived from the germline of another mammalian species, such as a mouse, have been grafted onto human framework sequences.

As used herein, an "antigen-binding fragment of an antibody" means a part of an antibody, i.e. a molecule corresponding to a portion of the structure of the antibody of the invention, that exhibits antigen-binding capability for SIRPa v1, possibly in its native form; such fragment especially exhibits the same or substantially the same antigen-binding specificity for said antigen compared to the antigen-binding specificity of the corresponding four-chain antibody.

Advantageously, the antigen-binding fragments have a similar binding affinity as the corresponding 4-chain antibodies. However, antigen-binding fragment that have a reduced antigen-binding affinity with respect to corresponding 4-chain antibodies are also encompassed within the invention. The antigen-binding capability can be determined by measuring the affinity between the antibody and the target fragment. These antigen-binding fragments may also be designated as "functional fragments" of antibodies.

Antigen-binding fragments of antibodies are fragments which comprise their hypervariable domains designated CDRs (Complementary Determining Regions) or part(s) thereof encompassing the recognition site for the antigen, i.e. the extracellular domain of SIRPa v1, thereby defining antigen recognition specificity.

Each Light and Heavy chain variable domains (respectively VL and VH) of a four-chain immunoglobulin has three CDRs, designated VL-CDR1 (or LCDR1), VL-CDR2 (or LCDR2), VL-CDR3 (or LCDR3) and VH-CDR1 (or HCDR1), VH-CDR2 (or HCDR2), VH-CDR3 (or HCDR3), respectively.

The skilled person is able to determine the location of the various regions/domains of antibodies by reference to the standard definitions in this respect set forth, including a reference numbering system, a reference to the numbering system of KABAT or by application of the IMGT "collier de perle" algorithm. In this respect, for the definition of the sequences of the invention, it is noted that the delimitation of the regions/domains may vary from one reference system to another. Accordingly, the regions/domains as defined in the present invention encompass sequences showing variations in length or localization of the concerned sequences within the full-length sequence of the variable domains of the antibodies, of approximately +/−10%.

Based on the structure of four-chain immunoglobulins, antigen-binding fragments can thus be defined by comparison with sequences of antibodies in the available databases and prior art, and especially by comparison of the location of the functional domains in these sequences, noting that the positions of the framework and constant domains are well defined for various classes of antibodies, especially for IgGs, in particular for mammalian IgGs. Such comparison also involves data relating to 3-dimensional structures of antibodies.

For illustration purpose of specific embodiments of the invention, antigen binding fragments of an antibody that contain the variable domains comprising the CDRs of said antibody encompass Fv, dsFv, scFv, Fab, Fab', F(ab')2. Fv fragments consist of the VL and VH domains of an antibody associated together by hydrophobic interactions; in dsFv fragments, the VH:VL heterodimer is stabilised by a disulphide bond; in scFv fragments, the VL and VH domains are connected to one another via a flexible peptide linker thus forming a single-chain protein. Fab fragments are monomeric fragments obtainable by papain digestion of an antibody; they comprise the entire L chain, and a VH-CH1 fragment of the H chain, bound together through a disulfide bond. The F(ab')2 fragment can be produced by pepsin digestion of an antibody below the hinge disulfide; it comprises two Fab' fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen binding sites, like the native immunoglobulin molecule; on the other hand, Fv (a VHVL dimmer constituting the variable part of Fab), dsFv, scFv, Fab, and Fab' fragments are monovalent, i.e. they comprise a single antigen-binding site. These basic antigen-binding fragments of the invention can be combined together to obtain multivalent antigen-binding fragments, such as diabodies, tribodies or tetrabodies. These multivalent antigen-binding fragments are also part of the present invention.

As used herein, the term modified antibody includes "bispecific" antibodies and refers to antibodies that recognize two different antigens by virtue of possessing at least one region (e.g. derived from a variable region of a first antibody) that is specific for a first antigen, and at least a second region (e.g. derived from a variable region of a second antibody) that is specific for a second antigen. A bispecific antibody specifically binds to two target antigens and is thus one type of multispecific antibody. Multispecific antibodies, which recognize two or more different antigens, can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen such as BiME (Bispecific Macrophage Enhancing antibodies), BiTE (bispecific T cell engager), DART (Dual affinity retargeting); DNL (dock-and-lock), DVD-Ig (dual variable domain immunoglobulins), HAS (human serum albumin), kih (knobs into holes).

Antigen-binding antibody mimetics are organic compounds that specifically bind antigens, but that are not structurally related to antibodies. They are usually artificial peptides or small proteins with a molar mass of about 3 to 20 kDa. Nucleic acids and small molecules are sometimes considered antibody mimetics as well, but not artificial antibodies, antibody fragments and fusion proteins composed from these. Common advantages over antibodies are better solubility, tissue penetration, stability towards heat and enzymes, and comparatively low production costs. Antibody mimetics are being developed as therapeutic and diagnostic agents. Antigen-binding antibody mimetics may also be selected among the group comprising affibodies, affilins, affimers, affitins, DARPins, and Monobodies.

An antigen-binding antibody mimetic is more preferentially selected from the groups comprising affitins and anticalins. Affitins are artificial proteins with the ability to selectively bind antigens. They are structurally derived from the DNA binding protein Sac7d, found in *Sulfolobus acidocaldarius*, a microorganism belonging to the archaeal domain. By randomizing the amino acids on the binding surface of Sac7d, e.g. by generating variants corresponding to random substitutions of 11 residues of the binding interface of Sac7d, an affitin library may be generated and subjecting the resulting protein library to rounds of ribosome display, the affinity can be directed towards various targets, such as peptides, proteins, viruses and bacteria. Affitins are antibody mimetics and are being developed as tools in biotechnology. They have also been used as specific inhibitors for various enzymes (Krehenbrink et al., J. mol. Biol., 383:5, 2008). The skilled person may readily develop affitins with the required binding properties using methods know in the art, in particular as disclosed in patent application WO2008068637 and the above-cited publication, in particular the generation of phage display and/or ribosome display libraries and their screening using an antigen as disclosed herein. Anticalins are artificial proteins that are able to bind to antigens, either to proteins or to small molecules. They are antibody mimetics derived from human lipocalins which are a family of naturally binding proteins. Anticalins are about eight times smaller with a size of about 180 amino acids and a mass of about 20 kDa (Skerra, Febs J., 275:11, 2008). Anticalin phage display libraries have been generated which allow for the screening and selection, in particular of anticalins with specific binding properties. The skilled person may readily develop anticalins with the required binding properties using methods know in the art, in particular as disclosed in EP patent EP1270725 B1, U.S. Pat. No. 8,536, 307 B2, Schlehuber and Skerra, Biophys. Chem., 96:2-3, 2002 and the above-cited publication, in particular the generation of phage display and/or ribosome display libraries and their screening using an antigen as disclosed herein. Anticalins and affitins may both be produced in a number of expression system comprising bacterial expression systems. Thus, the invention includes the use of affitins, anticalins and other similar antibody mimetics with the features of the antibodies described herein, in particular with regard to their binding capability to SIRPa v1, to the inhibition of the binding of human CD47 to human SIRPa v1, and to their non-binding property on human SIRPa v2, and/or to their lack of capability to prevent or inhibit the binding of human CD47 to human SIRPa v2, all of which are contemplated as mimetics according to the invention.

Accordingly, bispecific antibodies of the invention are directed against SIRPa v1 and a second antigen that is not present on human SIRPa v2 nor on human SIRPg. In any embodiment according to the present invention, the modified anti-human SIRPa v1 antibody may be bispecific and may be defined as a modified antibody or modified antigen-binding fragment thereof or modified antigen-binding antibody mimetic or bi-specific chimeric molecule.

As used herein, a "modified antibody" may also correspond to a molecule comprising an antibody or an antigen-binding fragment thereof, wherein said monoclonal antibody or functional fragment thereof is associated with a functionally different molecule. A modified antibody of the invention may be either a fusion chimeric protein or a conjugate resulting from any suitable form of attachment including covalent attachment, grafting, chemical bonding with a chemical or biological group or with a molecule, such as a PEG polymer or another protective group or molecule suitable for protection against proteases cleavage in vivo, for improvement of stability and/or half-life of the antibody or functional fragment. With similar techniques, especially by chemical coupling or grafting, a modified antibody can be prepared with a biologically active molecule, said active molecule being for example chosen among toxins, in particular *Pseudomonas* exotoxin A, the A-chain of plant toxin ricin or saporin toxin, especially a therapeutic active ingredient, a vector (including especially a protein vector) suitable for targeting the antibody or functional fragment to specific cells or tissues of the human body, or it may be associated with a label or with a linker, especially when fragments of the antibody are used. PEGylation of the antibody or functional fragments thereof is a particular interesting embodiment as it improves the delivery conditions of the active substance to the host, especially for a therapeutic application. PEGylation can be site specific to prevent interference with the recognition sites of the antibodies or functional fragments, and can be performed with high molecular weight PEG. PEGylation can be achieved through free cysteine residues present in the sequence of the antibody or functional fragment or through added free Cysteine residues in the amino sequence of the antibody or functional fragment. According to the present invention, when the term "antibody" is used, it means either an antibody, an antigen-binding fragment thereof, an antigen-binding antibody mimetic or a modified antibody.

In an embodiment, the anti-SIRPa v1 antibody or antigen-binding fragment thereof or antigen-binding antibody mimetic is modified.

In a particular embodiment of the invention, the antibody or antigen binding fragment thereof or antigen-binding antibody mimetic or modified antibody for use in the prevention and/or treatment of a disease in a subject that is SIRPa v1 positive comprises a heavy chain variable domain comprising or consisting of the amino acid sequence selected from the group consisting of SEQ ID No: 18; SEQ ID No: 19; SEQ ID No: 20, SEQ ID No: 21; SEQ ID No: 22 and SEQ ID No: 23; in particular the heavy chain variable domain comprises or consists of the amino acid sequence of SEQ ID No: 20.

In a particular embodiment of the invention, the antibody or antigen binding fragment thereof or antigen-binding antibody mimetic or modified antibody for use in the prevention and/or treatment of a disease as described herein in a human subject that is SIRPa v1-positive comprises or consists of:

A heavy chain variable domain comprising or consisting of the amino acid sequence of SEQ ID No: 20;

A light chain variable domain comprising or consisting of the amino acid sequence of SEQ ID No: 17.

The invention thus also concerns an antibody or an antigen-binding fragment thereof which binds specifically to human SIRPa v1, and which inhibits the binding of human CD47 to human SIRPa v1, and which does not prevent or inhibit the binding of human CD47 to human SIRPa v2, for use in a treatment or the prevention of a disease in a SIRPa v1-positive subject. The antibody or antigen-binding fragment thereof or antigen-binding antibody mimetic or modified antibody binds specifically to SIRPa v1 and antagonizes the interaction between SIRPa v1 and CD47.

The expression "binds specifically" or any equivalent term refers to the capability of the antibody or the antigen-binding fragment thereof to interact with human SIRPa v1 and to bind to human SIRPa v1, while they do not bind or they bind with a significant weaker binding affinity to other molecules, in particular to SIRPa v2, in particular to human SIRPg, in particular to human SIRPa v2 and SIRPg. Binding and specificity can be assessed by SPR (Surface Plasmon Resonance, e.g. Biacore), ELISA or Western Blot analysis. In a particular embodiment, the antibody or the antigen-binding fragment thereof or a chimeric molecule comprising said antibody or antigen-binding antibody mimetic targets and binds to SIRPa v1 as an isolated protein with an affinity (KD) of at least 10E-9 M, in particular at least than 10E-10 M. The antibody for use according to the invention may exhibit a KD value comprised between 10E-8 M and 10E-11 M, preferably comprised between 10E-9 M and 10E-10 M, for SIRPa v1, particularly by Blitz analysis.

The antibody for use in the prevention and/or treatment of a disease does not prevent or inhibit the binding of human CD47 to human SIRPa v2. In other words, this antibody or antigen-binding fragment thereof or antigen-binding antibody mimetic or modified antibody does not have a significant effect on the binding of human CD47 to human SIRPa v2 on the contrary to the binding of human CD47 to human SIRPa v1. In particular, the antibody or antigen-binding fragment does not prevent or inhibit the binding of human CD47 to human SIRPa v2 over 70%, preferably 60%, preferably 50% and most preferably 25% as compared to a negative control molecule, in a binding assay. The binding between CD47 and SIRP v2 (or SIRPg) may be assessed according to the methods disclosed in the examples of the present invention, in particular the Blitz method disclosed in example 6, but also by Biacore analysis, ELISA assay, or flow cytometry with cells expressing SIRPa v2 and/or SIRPg. A binding is considered prevented or inhibited when the KD value corresponding to the affinity of CD47 to SIRPa v2 (or SIRPg) is over 1E-7 M.

The prevention or the inhibition of binding may be determined by various methods known by the person skilled in the art; these methods include, but are not limited to, Biacore analysis, Blitz analysis and Scatchard plot.

The decrease or the inhibition of the binding of human CD47 to human SIRPa v1 means that the antibody or antigen-binding fragment thereof or antigen-binding antibody mimetic or modified antibody decreases the interaction between SIRPa v1 and CD47, i.e. the antibody or antigen-binding fragment thereof partially or fully inhibits the binding of human CD47 to human SIRPa v1, or in other words, specifically binds to human SIRPa v1, and antagonizes the interaction between human SIRPa v1 and human CD47. In particular, the anti-human SIRPa v1 antibody or antigen-binding fragment thereof has the capability to decrease or inhibit the binding of human CD47 to human SIRPa v1 by at least 50%, preferably 60%, more preferably 70%, more preferably 80% and most preferably 90%, and in a particular embodiment 100%, as compared to a negative control molecule, in a binding assay. In particular, the anti-SIRPa v1 antibody or antigen-binding fragment thereof has the capability to reduce or inhibit the binding of human CD47 to human SIRPa v1 from 50% to 100%, more preferably from 60% to 90%, as compared to a negative control molecule, in a binding assay.

According to the invention, it can be considered that an antibody (or antigen-binding fragment thereof or antigen-binding antibody mimetic or modified antibody) does not prevent or inhibit the binding of human CD47 to human SIRPa v2 if said antibody (or antigen-binding fragment thereof or antigen-binding antibody mimetic) does not induce an increase superior to 5 log, preferably not superior to 4 log, more preferably not superior to 3 log, more preferably not superior to 2 log, and most preferably not superior to 1 log, of the KD value of human CD47 in a SIRPa v2 binding competitive assay, in particular by Blitz assay. Alternatively, it can be considered that an antibody or antigen-binding fragment thereof or antigen-binding antibody mimetic does not prevent or inhibit the binding of human CD47 to human SIRPa v2 if said antibody or antigen-binding fragment or antigen-binding antibody mimetic does not reduce the binding of human CD47 to human SIRPa v2 over 25% as compared to a negative control molecule, in a binding assay.

In a particular embodiment of the invention, the antibody or antigen-binding fragment thereof for use according to the invention may exhibit a transitional binding to SIRPa v2, but does not prevent or inhibit the binding of human CD47 to human SIRPa v2. The anti-human antibody, antigen-binding fragment thereof or antigen-binding antibody mimetic for use according to the invention significantly inhibits, decreases, antagonizes or competes with the binding of human CD47 to human SIRPa v1, while the same antibody, antigen-binding fragment thereof or antigen-binding antibody mimetic does not decrease, antagonize, inhibit or compete with the binding of human CD47 to human SIRPa v2. The antagonist effect may be determined using methods as illustrated in the examples of the present application.

A SIRPa v1-positive subject is a person that comprises at least one SIRPa v1 allele, i.e. a person that is either heterozygous for SIRPa v1 (comprising SIRPa v1 and SIRPa v2 alleles), or homozygous for SIRPa v1 (comprising two SIRPa v1 alleles). According to the present invention, human SIRPa v1 may be defined as a SIRPa comprising the amino acid residue L on position 44 of SEQ ID No: 3, or on position 14 of SEQ ID No: 24; or comprising amino acid residue T on position 50 of SEQ ID No: 3, or on position 20 of SEQ ID No: 24; or comprising amino acid residue T on position 52 of SEQ ID No: 3, or on position 22 of SEQ ID No: 24; or comprising amino acid residue R on position 54 of SEQ ID No: 3, or on position 24 of SEQ ID No: 24; or comprising amino acid residue A on position 57 of SEQ ID No: 3, or on position 27 of SEQ ID No: 24; or comprising amino acid residue G on position 75 of SEQ ID No: 3, or on position 45 of SEQ ID No: 24; or comprising amino acid residue D on position 95 of SEQ ID No: 3, or on position 65 of SEQ ID No: 24; or comprising amino acid residue L on position 96 of SEQ ID No: 3, or on position 36 of SEQ ID No: 24; or comprising amino acid residue N on position 100 of SEQ ID No: 3, or on position 70 of SEQ ID No: 24; or comprising amino acid residue R on position 107 of SEQ ID No: 3, or on position 77 of SEQ ID No: 24; or comprising amino acid residue G on position 109 of SEQ ID No: 3, or on position 79 of SEQ ID No: 24; or comprising amino acid residue D on position 130 of SEQ ID No: 3, or on position 100 of SEQ ID No: 24; or comprising amino acid residue V on position 132 of SEQ ID No: 3, or on position 102 of SEQ ID No: 24. In a particular embodiment of the invention, human SIRPa v1 comprises amino acid residue V on position 132 of SEQ ID No: 3 and amino acid residue D on position 130 of SEQ ID No: 3, or comprises amino acid residues D and V on positions 100 and 102 of SEQ ID No: 24 respectively. Alternatively, a SIRPa v1 may be defined as a SIRPa isoform comprising in its amino acid sequence the sequence of SEQ ID No: 1, while a SIRPa v2 isoform may be defined as a SIRPa isoform comprising in its amino acid sequence the sequence of SEQ ID No: 2. Alternatively, a SIRPa v1-positive subject may be defined as a subject whose genome comprises within the SIRPa allele a gene encoding for a SIRPa RNA translated into a SIRPa protein with amino acid residues D and V on positions 130 and 132 of SEQ ID No: 3 respectively, or on positions 100 and 102 of SEQ ID No: 24 respectively.

The invention is based on the unexpected observation made by the inventors that some anti-human SIRPa antibodies do not bind equally to the different isoforms of SIRPa, and some antibodies can be useful for treating, preventing, thereby in particular encompassing inhibiting, slowing the progression of, or reducing the symptoms associated with a disease or a disorder in a SIRPa v1-positive subject, in particular a disease wherein CD47 and/or SIRPa is involved, in particular a disease wherein CD47 is over-expressed in a SIRPa v1-positive subject.

In a particular embodiment of the invention, the antibody or antigen-binding fragment thereof is used for the treatment and/or the prevention of a disease selected from the group consisting of an infectious disease, a chronic inflammatory disease, an auto-immune disease, a neurologic disease, a brain injury, a nerve injury, a polycythemia, a hemochromatosis, a trauma, a sceptic shock, a chronic infectious disease, in particular *Pseudomonas* and Cytomegalovirus infectious disease, fibrosis, atherosclerosis, obesity, type II diabetes, melanoma and a transplant dysfunction. In a particular embodiment, the antibody is used for the prevention and/or the treatment of a cancer, in particular inflammatory cancer and cancers with infiltrated myeloid cells, particularly with infiltrated dendritic cells and/or myeloid-derived suppressor cells (MDSCs) and/or tumor associated macrophage cells (TAMs). In a particular embodiment of the invention the antibody is used for the treatment and/or the prevention of melanoma, trauma or sceptic shock. In a particular embodiment, the antibody or antigen-binding fragment thereof is use for therapeutic vaccination against a disease, in particular against a cancer, in particular inflammatory cancers and cancers with infiltrated myeloid cells, in particular a cancer with infiltrated dendritic cells and/or MDSCs and/or TAM cells. In a particular embodiment, the antibody or antigen-binding fragment thereof is used for the treatment and/or the prevention of a disease wherein CD47 is over-expressed. In another embodiment, the antibody or antigen-binding fragment thereof are used for the treatment and/or the prevention of melanoma. The use of the antibody or antigen-binding fragment thereof according to the invention enhances the cross-presentation of antigens by Antigen Presenting Cells (APCs), in particular the cross-presentation of antigens to T cells by APCs, in particular the cross-presentation of antigens to CD8+ T cells by dendritic cells. Due to the increase in the cross-presentation of antigens, the use of the antibody or antigen-binding fragment thereof is useful in therapeutic vaccination against the recited diseases, in particular against cancers, in a subject that is SIRPa v1-positive, in particular when the disease is related to the over-expression of CD47, more particularly when the disease is related to the over-expression of CD47 by cancer cells or tumor cells. Over-expression of CD47 may be assessed by comparing CD47 expression in a cancerous cell and in a healthy cell issued from the same tissue. CD47 expression may be assessed by methods known in the art like quantification of mRNA, for example by RT-qPCR, or protein quantification by flow cytometry, western blot, ELISA, and the like.

In a particular embodiment, the antibody or antigen-binding fragment thereof is used for the prevention and/or the treatment of a cancer, wherein at least one of the antigen selected from the group consisting of Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, Cytomegalovirus, or from the group of single-point mutated antigens derived from the group consisting of the antigens of CTNNB1 gene, CASP8 gene, HER2 gene, p53 gene, KRAS gene, NRAS gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), is expressed, in particular over-expressed. Alternatively or complementarily, the antibody or antigen-binding fragment thereof is used for the therapeutic vaccination against a cancer wherein at least one of the antigen selected from the group consisting of the above-mentioned antigens is expressed, in particular over-expressed.

In a particular embodiment of the invention, the anti-human SIRPa v1 antibody or antigen-binding fragment thereof or antigen-binding antibody mimetic or modified antibody for use has the following properties:
  It does not bind specifically to human SIRPa v2;
  It does not inhibit or prevent the binding of human CD47 to human SIRPg, in particular it does not bind to human SIRPg.

According to the invention, it can be considered that an antibody or antigen binding fragment thereof or antigen-binding antibody mimetic or modified antibody does not bind specifically to human SIRPa v2 if said antibody or antigen-binding fragment or antigen-binding antibody mimetic or modified antibody thereof has a binding affinity lower than 1E-8 M, more preferably lower than 1E-7 M, for SIRPa v2, in particular by Blitz analysis. The bio-availability of an antibody or antigen-binding fragment thereof or antigen-binding antibody mimetic which does not bind specifically to human SIRPa v2 may be enhanced when the SIRPa v1-positive subject is heterozygous for SIRPa v1.

According to the invention, it can be considered that an antibody or antigen binding fragment thereof or antigen-binding antibody mimetic or modified antibody does not inhibit or prevent the binding of human CD47 to human SIRPg if said antibody or antigen-binding fragment thereof or antigen-binding antibody mimetic does not induce an increase, or induce an increase inferior to 5 log, more preferably inferior to 4 log, more preferably inferior to 3 log, more preferably inferior to 2 log, and most preferably inferior to 1 log, of the KD value of human CD47 to human SIRPg in a SIRPg binding competitive assay, for example by Blitz analysis. In a particular embodiment, the antibody or antigen-binding fragment thereof or antigen-binding mimetic does not bind specifically to human SIRPg if said antibody or antigen-binding fragment thereof or antigen-binding antibody mimetic has a KD value superior to 10E-8 M, preferably superior to 10E-7 M, more preferably superior to 10E-6 M, for SIRPg, in particular by Blitz analysis.

The antibody or antigen binding fragment thereof or antigen-binding antibody mimetic or modified antibody for use in the treatment and/or the prevention of a disease in a SIRPa v1-positive subject may furthermore have at least one of the following properties, in particular at least two of the following properties, in particular at least three of the following properties, in particular all the following properties:
  it binds with human SIRPa v1 with an affinity (KD) of at least 10E-8 M, in particular at least 10E-9 M, more preferably at least 10E-10 M; and/or
  it does not inhibit the proliferation and/or the activation of human T cells, in particular in vivo; and/or
  it enhances the activation of macrophages; and/or
  it enhances the cross-presentation of at least one antigen by antigen-presenting cells to human T cells, in particular to human CD8+ T cells.

The binding capability of the antibody or antigen binding fragment thereof or antigen-binding antibody mimetic or modified antibody to human SIRPa v1 may be assessed as already explained, for example by SPR (Surface Plasmon Resonance, e.g. Biacore), ELISA, flow cytometry or Western Blot analysis.

The proliferation and/or activation of human T cells, in particular in vivo, may be assessed according to methods known in the art; in particular the methods described in the examples of the present invention like thymidine incorporation. In a particular embodiment, the use of an anti-SIRPa v1 antibody or antigen-binding fragment thereof or antigen-binding antibody mimetic thereof or antigen-binding antibody mimetic or modified antibody does not decrease or does not inhibit the proliferation of T cells over 20% as compared with a negative control. On the contrary to the use of anti-human CD47 antibodies, the use of the anti-human SIRPa v1 antibodies, or antigen-binding fragment thereof or antigen-binding antibody mimetic does not have a significant effect on the proliferation of human T cells, while anti-CD47 antibodies inhibit the proliferation of human T cells.

The activation of human macrophages may be assessed according to various methods, including the methods described in the examples of the present invention. In a particular embodiment, a macrophage is activated when its secretion of chemokine MIP-1a/CCL-3 and/or chemokine MIP-1b/CCL4 is increased as compared to a negative control, in particular the secretion of chemokine MIP-1a/CCL-3 and/or chemokine MIP-1b/CCL4 is increased by at least 20% as compared to a negative control.

The cross-presentation of at least one antigen by Antigen Presenting cells to human T cells, in particular to human CD8+ T cells, may be assessed by various methods, including the methods described in the examples of the present invention. In particular, it is considered that cross-presentation is enhanced when the secretion of IL-2 by T cells is enhanced in particular by at least 20%, more preferably by at least 50%. Alternatively, Cross-presentation is enhanced when the secretion of IFNg by T cells is enhanced in particular by at least 20%, more preferably by at least 50%.

The invention also concerns the use of a polypeptide, in particular an antigen, for the production and/or for the selection of an antibody, or antigen-binding fragment thereof or antigen-binding antibody mimetic or modified antibody for use as detailed here above. Accordingly, provided herein is a polypeptide useful in particular for the production of anti-human SIRPa v1 antibody, and/or for the selection and/or the production of such an antibody, and/or for testing the binding affinity of such an antibody. To this end, it is also provided a polypeptide, in particular an antigen, comprising or consisting of the epitope of human SIRPa v1 consisting of SEQ ID No: 1 (KGSPDDV) or SEQ ID No: 4 (KFRKGSPDDVE) or SEQ ID No: 25 (DD-VEFKSGAGTELSVR) for use in the selection of an antibody, antigen-binding fragment thereof or antigen-binding antibody mimetic, which inhibits the binding of human CD47 to human SIRPa v1, and which does not prevent or decrease the binding of human CD47 to human SIRPa v2, in particular which does not bind specifically to human SIRPa v2.

SEQ ID No: 1 corresponds to an epitope sequence recognized by anti-human SIRPa antibodies that have a significant binding capability for SIRPa v1 isoforms, which inhibit the binding of human CD47 to human SIRPa v1 and which do not inhibit the binding of human CD47 to SIRPa v2. Therefore, a polypeptide comprising the epitope sequence the amino acid of SEQ ID No: 1, SEQ ID No: 4 or SEQ ID No: 25 may be useful for the production of an antibody that could be used in the treatment and/or the prevention of a disease in a SIRPa v1-positive subject. The specific binding between the antibody or antigen-binding fragment thereof or antigen-binding antibody mimetic or modified antibody and the epitope (or the region comprising the epitope) implies that the antibody exhibits appreciable affinity for the epitope (the region comprising the epitope) on a particular protein or antigen (here: SIRPa v1). "Appreciable affinity" or "specific binding" or "specifically bind to" includes binding with an affinity of about 10E-8 M (KD) or stronger. Preferably, binding is considered specific when the binding affinity is between 10E-8 M (KD) and 10E-12 M (KD), optionally between 10-8 M (KD) and 10E-10 M (KD), in particular at least 10E-8 M (KD). Whether a binding domain specifically reacts with or binds to a target can be tested readily by, inter alia, comparing the reaction of said binding domain with a target protein or antigen with the reaction of said binding domain with proteins or antigens other than the target protein. The terms "specific binding" or "specifically bind to" do not mean that an antibody recognizes and binds to a single target molecule, but that the antibody has a binding affinity that is higher for its target molecule relative to other molecules and in particular has a binding affinity for a target molecule over a given affinity as detailed here above. Used in the negative form, the terms "specific binding" or "specifically bind to" mean that an antibody recognizes the target molecule with a low affinity, or does not recognize the target molecule, i.e. the binding between the antibody and the target molecule is not specific. Preferably, a binding is recognized not specific when the binding affinity is lower than 10-8 M (KD). Compared molecules in respect of which binding may be regarded as specific are in particular SIRPg and SIRPa isoforms.

The inventors demonstrate in the examples of the invention that two specific Single Nucleotide Polymorphisms (SNPs) (namely SNP 15 and SNP 16, their combination corresponding to SNP 17) are responsible for the non-recognition of human SIRPa v2 by the antibodies or antigen binding fragment thereof or antigen-binding antibody mimetic or modified antibody used according to the invention. Both SNPs encode amino acid residues located within the epitope of SEQ ID No: 1, SEQ ID No: 4 and SEQ ID No: 25. Due to the polymorphism of this specific region of SIRPa, antibody or antigen binding fragment thereof or antigen-binding antibody mimetic or modified antibody are able to bind to SIRPa v1 and disrupt the binding of human CD47 to human SIRPa v1, without impairing the binding of human CD47 to human SIRPa v2. Moreover, such antibody or antigen binding fragment thereof or antigen-binding antibody mimetic or modified antibody is also unable to prevent or inhibit the binding of human CD47 to human SIRPg. In particular, such antibody or antigen binding fragment thereof or antigen-binding antibody mimetic or modified antibody does not bind specifically to human SIRPg.

The polypeptide comprising the epitope of SEQ ID No: 1 may also comprise at least one other epitope, the epitope of SEQ ID No: 5 (SLIPVGP) and/or the epitope of SEQ ID No: 6 (GRELIYNQKEGH), both being linear epitopes recognized by anti-human SIRPa v1 antibody, antigen-binding fragment thereof and antigen-binding antibody mimetic or antigen-binding antibody mimetic or modified antibody. Alternatively, the polypeptide may also furthermore comprise at least one epitope selected from the group comprising SEQ ID No: 7 (ELIYNQKEGHFPR) and SEQ ID No: 8 (RNNMDFSIRIGN), both being conformational epitopes recognized by anti-human SIRPa v1 antibody, antigen-binding fragment thereof, antigen-binding antibody mimetic, and modified antibody.

The polypeptide, or the antigen, comprising the epitope of SEQ ID No: 1 or SEQ ID No: 4 or SEQ ID No: 25 may be used for the preparation (or the production) of antibodies, or antigen-binding fragment thereof or antigen-binding antibody mimetic or antigen-binding antibody mimetic or modified antibody, for example by immunizing a non-human animal, in particular a non-human mammal, and collecting the resulting serum or B cells of said immunized non-human animal to obtain antibodies directed against the antigen(s) comprised within the polypeptide. The recovered antibodies may then be humanized, or modified to obtain antigen-binding fragment thereof, or bi-functional or bi-specific antibodies. The recovered B cells may be transformed into hybridoma for the production of anti-human SIRPa v1 antibodies. The antibodies produced may be recovered and selected according to a method of selection detailed here below.

The invention also relates to the use of a polynucleotide encoding an antigen of human SIRPa v1, for the production of a polypeptide, in particular an antigen, comprising the epitope of SEQ ID No: 1 or SEQ ID No: 4 or SEQ ID No: 25. The polynucleotide may comprise at least a portion of SEQ ID No: 26, said portion comprising the nucleic acid residues encoding the epitope of SEQ ID No: 1 or SEQ ID No: 4 or SEQ ID No: 25. SEQ ID No: 26 corresponds to a cDNA encoding a SIRPa v1 protein. The polynucleotide may be used in a production system, for example when the polynucleotide is inserted within an expression vector, like a plasmid, for producing the polypeptide comprising the epitope of SIRPa v1 comprising amino acid residues of SEQ ID No: 1, SEQ ID No: 4 or SEQ ID No: 25. In a particular embodiment, the polynucleotide encodes a portion of SEQ ID No: 26 comprising at least the amino acid residues of SEQ ID No: 1 or SEQ ID No: 4 or SEQ ID No: 25, and the amino acid residues of SEQ ID No: 5 and/or SEQ ID No:6; or the amino acid residues of SEQ ID No: 7 and/or SEQ ID No: 8.

The invention also relates to a method for selecting and recovery an antibody, an antigen-binding fragment thereof, an antigen-binding antibody mimetic, or a modified antibody which binds specifically to human SIRPa v1, and which decreases or inhibits the binding of human CD47 to human SIRPa v1, and which does not prevent or inhibit the binding of human CD47 to human SIRPa v2. The method of selection and recovery comprises the following steps:
  a) Testing the capability of the compound (i.e. the antibody, the antigen-binding fragment thereof, the antigen-binding antibody mimetic, or the modified antibody) to bind specifically to human SIRPa v1, in particular the capability of the compound to bind specifically to an epitope comprising or consisting of SEQ ID No:1, SEQ ID No: 4 or SEQ ID No: 25; in particular the capability of the compound to bind specifically to amino acid residues D and V located respectively on positions 130 and 132 of SIRPa of SEQ ID No: 3; or located respectively on positions 100 and 102 of SIRPa of SEQ ID No: 24; and
  b) Testing the capability of the compound to decrease or inhibit the binding of human CD47 to human SIRPa v1; and
  c) Testing the capability of the compound not to prevent or inhibit the binding of human CD47 to human SIRPa v2; and/or
  d) In particular testing the capability of the compound not to prevent or inhibit the binding of human CD47 to human SIRPg;
and optionally:
  e) Testing the capability of the compound not to bind specifically to human SIRPa v2;
  f) Testing the capability of the compound not to bind specifically to human SIRPg; and/or The selected and recovered compound should have the following properties:
  It binds specifically to human SIRPa v1, in particular with an affinity of at least 1E-9 M, in particular 10E-9 M, more preferably with an affinity of at least 1E-10 M, in particular 10E-10 M;
  It decreases or inhibits the binding of human CD47 to human SIRPa v1;
  It does not prevent or inhibit the binding of human CD47 to human SIRPa v2;
  In particular it does not specifically bind to human SIRPg.

The selected and recovered compound may also exhibit at least one of the following properties, preferably at least two of the following properties:
  It does not prevent or inhibit the binding of human CD47 to human SIRPg; and/or
  It does not specifically bind to human SIRPa v2.

The binding specificity of the compound may be assessed according to the methods already described here above, for example by SPR (Surface Plasmon Resonance, e.g. Biacore), ELISA or Western Blot analysis. In particular, the compound binds specifically to SIRPa v1 when the binding affinity is at least 10E-8 M, more preferably at least 10E-9 M, or when the binding affinity is comprised between 10E-8 M and 10E-11 M, more preferably between 10E-9 M and 10E-10 M. the compound does not bind specifically to human SIRPa v2 or SIRPg when the binding affinity is lower than 1E-8 M. The prevention or inhibition of the binding of CD47 to human SIRPa v1, SIRPa v2 and SIRPg may be assessed by the methods already described therein, in particular by competitive assay, in particular by Blitz assay. It can be considered that a compound does not prevent or inhibit the binding of human CD47 to human SIRPa v1, SIRPa v2 or SIRPg if said compound does not induce an increase superior to 5 log, preferably not superior to 4 log, more preferably not superior to 3 log, more preferably not superior to 2 log, and most preferably not superior to 1 log, of the KD value of human CD47 in a SIRPa v1, SIRPA v2 or SIRPg binding competitive assay, in particular by Blitz assay. On the contrary, it can be considered that a compound prevents or inhibits the binding of human CD47 to human SIRPa v1, SIRPa v2 or SIRPg if said compound induces an increase superior to 1 log, preferably superior to 2 log, more preferably superior to 3 log, more preferably superior to 4 log, and most preferably superior to 5 log, of the KD value of human CD47 in a SIRPA v1, SIRPa v2 or SIRPg binding competitive assay, in particular by Blitz assay.

In a particular aspect, the method for selecting a compound may comprise at least one of the following steps, in particular at least two of the following steps, in particular at least three of the following steps, and in particular the four following steps:
  i) Testing the T cell proliferation in presence of the compound; and/or
  ii) Testing the T cell activation in presence of the compound; and/or
  iii) Testing the macrophage activation in presence of the compound; and/or
  iv) Testing the cross-presentation of an antigen, in particular a tumor antigen, in particular Melan-A melanoma tumor-associated antigen (TAA), by antigen presenting cells, in particular dendritic cells, to human T cells in presence of the compound, in particular the cross-presentation of the antigen by dendritic cells to CD8+ T cells.

According to this particular embodiment, the selected compound may exhibit at least one, preferably at least two, more preferably at least three, most preferably the four following properties:

It does not inhibit the human T cell proliferation; and/or
It does not inhibit the human T cell activation; and/or
It enhances the activation of macrophages; and/or
It enhances the cross-presentation of an antigen by antigen presenting cells to human T cells.

T cell proliferation and T cell activation may be determined by various methods. For example, the proliferation of T cells can be measured by incorporation of H3-thymidine. In particular, it is considered that a compound does not inhibit the proliferation of T-cells when the proliferation of T-cells is reduced by no more than 20% compared to a negative control. The T cell activation may be assessed by analyzing the expression of CD25 and/or CD69, for example by flow cytometry, western blot, ELISA, and the like, and/or by assessing the secretion of IFNg and/or IL2 as disclosed in the examples of the present invention. Cross-presentation may be assessed according to various methods, in particular by the method described in the examples of the present invention. In particular, it is considered that cross-presentation is enhanced when the secretion of IL-2 by T cells is enhanced by at least 20%, more preferably by at least 50% as compared to a negative control. Alternatively, Cross-presentation is enhanced when the secretion of IFNg by T cells is enhanced by at least 20%, more preferably by at least 50%, as compared to a negative control. The macrophage activation may be assessed by various methods, in particular the method described in the examples of the present invention. In particular, the macrophage activation may be assessed by dosage of chemokine(s) secretion. In particular, a macrophage is activated when the secretion of chemokine MIP-1a/CCL-3 and/or chemokine MIP-1b/CCL4 is increased as compared to a negative control, in particular when the increase of chemokine(s) secretion is over 20% as compared to a negative control.

It is also provided a method Provided herein are also in vitro or ex vivo methods for assessing the likelihood of effectiveness to a treatment wherein an anti-human SIRPa compound (i.e. an antibody, an antigen-binding fragment thereof, an antigen-binding antibody mimetic or a modified antibody), is to be administered to a human subject, in particular when the compound is an anti-human SIRPa v1 compound. The method comprises the determination of the presence of SIRPa v1 in a biological sample previously obtained from the subject, like blood, cells, biopsy or the like. The presence of SIRPa v1 may be determined by using the anti-SIRPa v1 compounds as defined herein, or produced according to the methods defined herein, or selected according to the methods described herein. The detection of SIRPa v1 within the sample is indicative that the treatment with an anti-human SIRPa v1 compound is likely to be effective. In other words, the present invention provides an in vitro or ex vivo method for the identification of a patient that is likely to be effectively treated with an anti-SIRPa compound, said method comprising the identification of the status of the patient among the group consisting of SIRPa v1/v1 patients, v1/v2 patients and v2/v2 patients, wherein a patient classified within the v1/v1 group or the v1/v2 group is likely to be treated effectively by an anti-SIRPa compound used according to the invention, and in particular wherein the therapeutic dose of anti-SIRPa compound administered to a SIRPa v1/v1 patient may be different (i.e. less important) than the therapeutic dose administered to a SIRPa v1/v2 patient. Alternatively, the method may comprise the detection of a genetic product (RNA or DNA) encoding SIRPa v1 protein. More particularly, the method comprises a step of determination of the SIRPa alleles of the subject (either v1 allele or v2 allele). A human subject is considered SIRPa v1-positive if at least one SIRPa allele comprises a nucleic acid sequence encoding the amino acid residues of SEQ ID No: 1, or SEQ ID No: 4 or SEQ ID No: 25. Alternatively, a subject is considered SIRPa v1-positive if at least one of its SIRPa allele comprises within its exon 3 the mutations consisting of the SIRPa v1 SNPs 15 (rs115287948) and 16 (rs114499682), or SIRPa v1 SNP 17, encoding the amino acid residue V on position 132 of SEQ ID No: 3, or on position 102 of SEQ ID No: 24, or encoding the amino acid residue V in SEQ ID No: 1 or 4, or the first amino acid residue V on SEQ ID No: 25; and if at least one of its SIRPa allele comprises within its exon 3 a nucleic sequence encoding the amino acid residues 5' DDV 3' within SIRPa. SNPs of SIRPa are well documented and available on online database like Genbank. Reference SNP ID numberS or "rs" are available on NCBI database. SIRPa v1 SNPs 15 and 16 correspond to a nucleic acid residues g and t respectively as detailed in the examples of the invention. Therefore, the method may comprise the determination of the SIRPa allele, for example by polymerase chain reaction, wherein the determination of a SIRPa v1-positive subject comprise the detection of a SIRPa sequence comprising the nucleic acid residues corresponding to at least a portion of human SIRPa exon 3, and wherein the SIRPa SNPs 15 and 16 are determined, as detailed here above, within at least one SIRPa alleles, in particular both SIRPa alleles.

To this end, the invention also relates to a kit of parts for determining the SIRPa status of a subject, said kit comprising pair of primers suitable for amplifying, in particular by polymerase chain reaction (PCR), or in particular by reverse transcription polymerase chain reaction (RT-PCR), at least a portion of SIRPa gene (like gDNA for example) or SIRPa transcript (like mRNA or cDNA for example), in particular said portion comprising at least a part of SIRPa exon 3, said portion comprising at least the localization of SIRPa SNP 15 and SNP 16 as defined here above, or in the examples of the invention, or the localization of SIRPa SNP 17 as defined here above, or in the examples of the invention; and the localization of the codon encoding the first amino acid residue D within the SIRPa v1 epitope of SEQ ID No: 1, or of SEQ ID No:4 or of SEQ ID No: 25. The localization of the missing codon in a nucleic acid sequence encoding SIRPa v2 may be assessed by aligning SEQ ID No: 27 (SIRPa v1 exon 3) and SEQ ID No: 31 (SIRPa v2 exon 3). Therefore, the pair of primers may comprise a first primer able to anneal with both nucleic acid sequences encoding SIRPa v1 and SIRPa v2, and a second primer able to anneal only with the nucleic acid sequence of SIRPa v1. The nucleic acid sequence of such primers may be determined by a person skilled in the art by aligning SEQ ID No: 27 (SIRPa v1 exon 3) and SEQ ID No: 31 (SIRPa v2 exon 3). In a particular embodiment, a primer able to anneal with the nucleic acid sequence encoding SIRPa v1 but not with the nucleic acid sequence encoding SIRPa v2 may be determined according to the localization of the SIRPa v1 SNPs, and may include a plurality of SIRPa v1 SNPs. In a particular embodiment, the SIRPa v1 specific primer is able to anneal, in particular in stringent conditions, within the nucleic acid sequence encoding at least the amino acid residues 5' DDV 3' within the epitope of SIRPa v1 of SEQ ID No: 1, or SEQ ID No: 4 or SEQ ID No: 25. Alternatively, the kit comprises a pair of primers both able to anneal with the nucleic acid sequences encoding either SIRPa v1 or SIRPa v2, thereby allowing amplification of a portion of the gene or transcript comprising at least a part of SIRPa exon 3, said portion comprising at least the localization of SIRPa SNP 15 and SNP 16 as defined here above, or in the examples of the invention, or the localization of SIRPa SNP 17 as defined here above, or in the examples of the invention; and the localization of the codon encoding the first amino acid residue D within the SIRPa v1 epitope of SEQ ID No: 1, or of SEQ ID No:4 or of SEQ ID No: 25, the kit further comprising a probe (i.e. a nucleic acid probe), in particular a tagged probe, able to anneal with a nucleic acid sequence encoding at least the amino acid residues 5' DDV 3' within the epitope of SIRPa v1 of SEQ ID No: 1, or SEQ ID No: 4 or SEQ ID No: 25.

It is also provided an in vitro or ex vivo method of diagnosis of the severity of a disease in particular a method of diagnosis suitable for the use in personalized medicine, wherein an anti-human SIRPa v1 compound (i.e. an antibody, an antigen-binding fragment thereof, an antigen-binding mimetic or a modified antibody), produced according to the methods described therein, or selected according to the methods described therein, is used for the detection of SIRPa v1 positive cells in a sample previously obtained from a subject, said method comprising the quantification of the expression of SIRPa v1. The quantification of the expression of SIRPa v1 may be assessed according to method known in the art, for example by quantification of antibodies bound on target proteins.

It is also provided a method of assisting a clinician in a decision to treat a patient with an anti-human SIRPa antibody, or antigen-binding fragment, or antigen-binding antibody mimetic or modified antibody, said method comprising the determination of the SIRPa alleles of the patient, in particular by using the anti-SIRPa compounds disclosed therein or by genotyping, and wherein a treatment with a first therapeutic dose of an anti SIRPa v1 compounds according to the present invention is likely to be effective in a patient that is SIRPa v1 homozygous; and wherein a treatment with an anti SIRPa v1 compound according to the present invention is unlikely to be effective for a patient that is SIRPa v2 homozygous; and wherein a treatment with a second therapeutic dose of an anti SIRPa v1 compounds according to the present invention is likely to be effective in a patient that is SIRPa v1/v2 heterozygous, in particular wherein the second therapeutic dose is higher than the first therapeutic dose.

It is also provided a method of assisting a clinician in a decision to treat a patient with an anti-human SIRPa antibody, or antigen-binding fragment, or antigen-binding antibody mimetic or modified antibody, wherein the therapeutic dose needed to treat the patient with the anti-human SIRPa compound is different if the patient is SIRPa v1/v1 homozygous or SIRPa v1/v2 heterozygous.

It is also provided a combination of compounds comprising an antibody, an antigen-binding fragment thereof, an antigen-binding antibody mimetic or a modified antibody, in particular an antibody, an antigen-binding fragment thereof, an antigen-binding antibody mimetic or a modified antibody for any use described therein, or, an antibody, an antigen-binding fragment thereof, an antigen-binding antibody mimetic or a modified antibody produced according to any method described therein, or an antibody, an antigen-binding fragment thereof, an antigen-binding antibody mimetic or a modified antibody selected according to any method described therein, with at least one second therapeutic agents. The second therapeutic agent may be selected from the group consisting of chemotherapeutic agents, radiotherapy agents, immunotherapeutic agents, cell therapy agents, antibiotics and probiotics, in particular immunotherapeutic agents selected from the group consisting of checkpoint blocker or activator of adaptive immune cells, particularly selected from the group consisting of anti-PDL1, anti-PD1, anti-CTLA4, anti-CD137, anti-CD2, anti-CD28, anti-CD40, anti-HVEM, anti-BTLA, anti-CD160, anti-TIGIT, anti-TIM-1/3, anti-LAG-3, anti-2B4, anti-VISTA, anti-OX40, anti-CD40 agonist, CD40-L, TLR agonists, anti-ICOS, ICOS-L, STING agonist, IDO inhibitor, oncolytic virus agonists, and B-cell receptor agonists. The combination of product is for use in the treatment or the prevention of a disease in a SIRPa v1 positive-subject. The composition may be in particular a pharmaceutical composition. Such a composition may comprise pharmaceutical acceptable components, like but not limited to pharmaceutically suitable excipient or carrier or vehicle, when used for systemic or local administration. A pharmaceutically suitable carrier or vehicle refers to a non-toxic solid, semi-solid or liquid filler, diluent, encapsulating material and formulation like phosphate buffered saline solutions, distilled water, emulsions such as oil/water emulsions, wetting agents and the like, dextrose, saline, ethanol and combinations thereof.

The invention is also related to a combination of compounds comprising:
(i) an antibody, an antigen-binding fragment thereof, an antigen-binding antibody mimetic or a modified antibody, which:
   binds specifically to human SIRPa v1 and/or SIRPa v2, in particular to human SIRPa v1 and human SIRPa v2, and which inhibits the binding of human CD47 to SIRPA v1 and/or SIRPA v2, in particular which inhibits the binding of human CD47 to SIRPA v1 and SIRPA v2;
   does not prevent or inhibit the binding of human CD47 to human SIRPg; and in particular does not bind specifically to human SIRPg;
   enhances the cross-presentation of an antigen, in particular a cancer antigen, by Antigen Presenting Cells, in particular by dendritic cells, to human T cells, in particular to human CD8+ T cells;
(ii) at least one second therapeutic agent selected from the group consisting of chemotherapeutic agents, radiotherapy agents, immunotherapeutic agents, cell therapy agents, antibiotics and probiotics, in particular immunotherapeutic agents selected from the group consisting of checkpoint blocker or activator of adaptive immune cells, particularly selected from the group consisting of anti-PDL1, anti-PD1, anti-CTLA4, anti-CD137, anti-CD2, anti-CD28, anti-CD40, anti-HVEM, anti-BTLA, anti-CD160, anti-TIGIT, anti-TIM-1/3, anti-LAG-3, anti-2B4, anti-VISTA, anti-OX40, anti-CD40 agonist, CD40-L, TLR agonists, anti-ICOS, ICOS-L, STING agonist, IDO inhibitor, oncolytic virus and B-cell receptor agonists;
for use in the treatment or the prevention of a disease, in particular a cancer, or for use in therapeutic vaccination against a disease, in particular against a cancer.

In a particular embodiment, the antibody, antigen-binding fragment thereof, antigen-binding antibody mimetic or modified antibody binds specifically to human SIRPa v1 and inhibits the binding of human CD47 to SIRPA v1.

The invention also relates to a combination of compounds comprising an antibody, an antigen-binding fragment thereof, an antigen-binding antibody mimetic or a modified antibody, in particular an antibody, an antigen-binding fragment thereof, an antigen-binding antibody mimetic or a modified antibody for any use described therein, or, an antibody, an antigen-binding fragment thereof, an antigen-binding antibody mimetic or a modified antibody produced according to any method described therein, or an antibody, an antigen-binding fragment thereof, an antigen-binding antibody mimetic or a modified antibody selected according to any method described therein, and at least one antigen issued or derived from the group consisting of the antigens of Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, Cytomegalovirus, or from the group of single-point mutated antigens derived from the group consisting of the antigens of CTNNB1 gene, CASP8 gene, hER2 gene, p53 gene, KRAS gene, NRAS gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA). Such a combination of compounds may be useful for use as a medicament or as a vaccine composition, or for use in the treatment or the prevention of a disease in a SIRPa v1 positive-subject.

The invention also provides a combination of compounds comprising:
(i) an antibody, an antigen-binding fragment thereof, an antigen-binding antibody mimetic or a modified antibody, which comprises:
a heavy chain variable domain comprising HCDR1, HCDR2 and HCDR3,
wherein:
HCDR1 comprises or consists of the amino acid sequence set forth in SEQ ID No: 9,
HCDR2 comprises or consists of the amino acid sequence set forth in SEQ ID No: 10 or SEQ ID No: 11, in particular HCDR2 comprises or consists of the amino acid sequence set forth in SEQ ID No: 11;
HCDR3 comprises or consists of the amino acid sequence set forth in SEQ ID No: 12, or SEQ ID No: 13, or SEQ ID No: 14 or SEQ ID No: 15; in particular HCDR3 comprises or consists of the amino acid sequence set forth in SEQ ID No: 13, or SEQ ID No: 14 or SEQ ID No: 15, in particular HCDR3 comprises or consists of the amino acid sequence set forth in SEQ ID No: 15;
and
a light chain variable domain comprising or consisting of the amino acid sequence selected from the group consisting of SEQ ID No: 16 and SEQ ID No: 17; in particular a light chain variable domain comprising or consisting of the amino acid sequence of SEQ ID No: 17;
and which enhances the cross-presentation of an antigen, in particular a cancer antigen, by Antigen Presenting Cells, in particular by dendritic cells, to human T cells, in particular to human CD8+ T cells;

(ii) at least one antigen selected from the group consisting of antigens from Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, Cytomegalovirus, or from the group of single-point mutated antigens derived from the group consisting of the antigens of ctnnb1 gene, casp8 gene, her2 gene, p53 gene, kras gene, nras gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), or any particular mutated antigen (neo-antigen or neo-epitope);
for use in the treatment or the prevention of a disease, in particular a cancer, or for use in therapeutic vaccination against a disease, in particular against a cancer, and wherein the cross-presentation of the at least one antigen by Antigen Presenting Cells, in particular by dendritic cells, to T cells, in particular CD8+ T cells, is enhanced.

The disease is in particular selected among the group consisting of an infectious disease, a chronic inflammatory disease, an auto-immune disease, a neurologic disease, a brain injury, a nerve injury, a polycythemia, a hemochromatosis, a trauma, a sceptic shock, a chronic infectious disease, in particular *Pseudomonas* and Cytomegalovirus infectious disease, fibrosis, atherosclerosis, obesity, type II diabetes, and a transplant dysfunction. The disease may also be selected from the group consisting of cancer, in particular inflammatory cancer and cancer with infiltrated myeloid cells, particularly with infiltrated MDSCs and/or TAM cells, cancer metastasis, in particular breast cancer metastasis, melanoma. In a particular embodiment, the disease is a cancer which comprises cancer cells expressing the at least one antigen.

In a particular embodiment of the invention, the combination comprises an antibody or antigen binding fragment thereof or antigen-binding antibody mimetic or modified antibody for use in the prevention and/or treatment of a disease, in particular a cancer, or for use in therapeutic vaccination against a disease, in particular against a cancer, wherein the antibody, antigen-binding fragment thereof, antigen-binding antibody mimetic or modified antibody, enhances cross-presentation of an antigen expressed in said disease, in particular a cancer, and is involved in eliciting a T cell response suitable for the treatment of said disease.

In a particular embodiment of the invention, the combination comprises a heavy chain variable domain comprising or consisting of the amino acid sequence selected from the group consisting of SEQ ID No: 18; SEQ ID No: 19; SEQ ID No: 20, SEQ ID No: 21; SEQ ID No: 22 and SEQ ID No:

23; in particular the heavy chain variable domain comprises or consists of the amino acid sequence of SEQ ID No: 20.

In a particular embodiment of the invention, the combination comprises an antibody or antigen binding fragment thereof or antigen-binding antibody mimetic or modified antibody for use in the prevention and/or treatment of a disease comprises or consists of:
  A heavy chain variable domain comprising or consisting of the amino acid sequence of SEQ ID No: 20;
  A light chain variable domain comprising or consisting of the amino acid sequence of SEQ ID No: 17.

Both DNA and RNA viruses have been shown to be capable of causing cancer in humans. Epstein-Barr virus, human papilloma virus, hepatitis B virus, and human herpes virus-8 (HHV-8 also known as Kaposi sarcoma herpes virus) are DNA viruses that are capable of causing the development of human cancers. Human T lymphotrophic virus type 1 and hepatitis C viruses are two RNA viruses that contribute to human cancers. Therefore, administration of a combination of compounds comprising an anti-human SIRPa v1 compound and an antigen issued or derived from these viruses may lead to enhance the cross-presentation of these antigens to human T cells, and therefore may enhance the response against cancer cells that exhibit such antigens.

The combination of compounds is also useful for use in the treatment of carcinoma, in particular when virus antigens are expressed, like in cervical carcinoma, nasopharyngeal carcinoma, hepatocarcinoma, Kaposi sarcoma and some leukemia (Liao, 2006). The combination of compounds is also useful for use in the treatment of glioblastomas, wherein Cytomegalovirus proteins are expressed. As an example, Merkel cell carcinoma (MCC) is an increasingly common neuroendocrine cancer of the skin and the main cause of non-melanoma skin cancer death and is described related to Merkel cell polyomavirus (MCV), the first polyomavirus directly linked to human cancer (Chang and Moore, 2012). The combination of compounds is also useful for use in the treatment of cervical cancers, wherein Hepatitis B virus proteins are expressed, and/or in neck tumors, skin cancers, in particular in immunosuppressed patient, and/or anogenital cancers. The combination of compounds is also useful for use in the treatment of malignancies associated with Epstein-Barr Virus, like B cells and T cells lymphomas like Burkitt's lymphoma, Hodgkin's disease, post-transplant lymphoproliferative disease, leiomyosarcoma, and nasopharyngeal carcinomas and some cases of stomach cancer. The combination of compounds is also useful for use in the treatment of cancer related to HIV infection, including anal cancer, Hodgkin disease, lung cancer, cancers of the mouth, cancers of the throat, some types of skin cancer, and liver cancer.

The combination of compounds is also useful for use in the treatment of cancers wherein some antigenic peptides result from oncogenic mutations. In particular antigens issued from CTNNB1, CASP8 and HER2 genes may comprise point mutations. Tumors with a high mutation rate, such as melanoma, lung carcinoma, or microsatellite instability (MSI) seen in colorectal carcinoma are expected to bear more mutated antigens. Other oncogenes are also linked with various cancers P53, KRAS, or NRAS. Peptides or tumor antigens derived from chromosomal translocations such as BCR-ABL in hematologic cancers or ETV6-AML1 are also identified. Mutations that permanently activate Ras oncogene are found in 20% to 25% of all human tumors and up to 90% in certain types of cancer, like pancreatic cancer. The combination of compounds is also useful for use in the treatment of cancers wherein the antigens are encoded by cancer-germline cells. Tumor antigens related to cancer germline cells are melanoma-antigen encoding genes (MAGE). More than 25 functional genes on X chromosome are defined as MAGE genes (MAGEA, MAGEB and MAGEC), and MAGEA1, MAGEA2 and MAGEA3 are involved in various cancers. Other genes like BAGE, GAGE, LAGE/NY-ESO1, SSX, also related to the X chromosome, are expressed in various cancers and not in normal tissues except germline cells and trophoblastic cells. NY-ESO-1 has been reported to be expressed by approximately 80% of synovial cell sarcomas as well as 10-50% of metastatic melanomas, breast, ovarian and lung cancers. MAGEA3 is one of the more frequently expressed TAA's (Tumor-Associated Antigen) in a variety of tumors, including melanoma. Peptides or tumor antigens that derive from cyclin-A1, a protein with pro-proliferative and anti-apoptotic properties, were identified. These antigens are expressed in testis and acute myeloid leukemia.

The combination of compounds is also useful for use in the treatment of cancers wherein cancer cells express antigens with low tumor specificity. Most identified differentiation antigens are present on melanoma cells but also in healthy cells. Peptides or tumor antigens derived from proteins such as tyrosinase, gp100/pmel17, Melan-A/MART-1, gp75/TRP1, or TRP2 are frequent in melanoma patients and healthy volunteers. MART-1, gp100, CEA, CD19 are tissue differentiation antigens, CD19 is a tumor antigen that is only expressed on normal and malignant B cells. Peptides or tumor antigens were also identified from the prostate specific antigen (PSA) and the prostatic acidic phosphatase (PAP), two proteins expressed in normal prostate and tumoral prostate tissues. Carcinoembryonic antigen (CEA) is often highly expressed in colorectal cancer and other epithelial tumors but is also present at lower level in a variety of normal epithelial cells of the intestinal tract but also in colorectal, gastric, pancreatic, non-small cell lung, and breast carcinomas. Alphafetoprotein (AFP) and CEA are Oncofetal antigens produced in the early stages of embryonic development and disappearing normally when the immune system is developed, but aberrantly present in some cancers as Hepatocellular Carcinoma. CA-125 (carcinoma antigen 125 or MUC16 known as mucin 16) is elevated in epithelial ovarian cancer, but can be expressed in a number of gynecologic (endometrial, fallopian tube) and non-gynecologic (pancreatic, breast, colon and lung) cancers. MUC1 (Mucin 1, cell surface associated protein) overexpression is often associated with colon, breast, ovarian, lung, gastrointestinal tract and pancreatic cancers.

The combination of compounds is also useful for use in the treatment of cancers wherein cancer cells overexpressed tumor antigens. Overexpressed antigens are shared by numerous tumors types. hTERT, EGFR, mesothelin are normal proteins overexpressed by cancer cells. hTERT (human telomerase reverse transcriptase) is a common tumor antigen expressed in about 85% of all cancers. A number of antigenic peptides or tumor antigens have been reported to be "overexpressed," an interesting example of overexpressed antigen is the peptide encoded by gene MOK—RAGE-1 on a renal cell carcinoma. RAGE-1 is also expressed in tumors of different histological types. Antigens issued from PRAME gene are also overexpressed in a number of tumor types, but expressed at low levels in various normal tissues. Other overexpressed genes include those derived from the inhibitor of apoptosis protein surviving, the wild-type p53 protein, or the oncogene and growth factor ERBB2 (HER2/NEU) which is overexpressed in many epithelial tumors such as ovarian and breast carcinoma. HER2 is expressed in many epithelial tumors and overexpressed in approximately 25% of all primary breast carcinomas where overexpression of HER2 is associated with poor prognosis. Sialyl-Tn (STn) tumor antigens (core-region carbohydrate antigen) are found in metastatic breast cancers and other cancers. Peptides or tumor antigens were also identified that derive from the protein Wilms tumor 1 (WT1 described initially in hereditary cases of Wilms' tumor). It is a transcription factor expressed at 10- to 1000-fold higher levels in leukemic versus normal cells and also overexpressed in acute leukemia, chronic myelogenous leukemia and myelodysplastic syndrome. Mesothelin is a cell-surface glycoprotein with normal expression limited to mesothelial cells lining the pleura, peritoneum, and pericardium but is also highly expressed in many cancers, including malignant mesothelioma, pancreatic cancer, ovarian cancer, lung adenocarcinoma, endometrial cancer, biliary cancer, gastric cancer, and pediatric acute myeloid leukemia (Hassan et al., 2016).

The combination of compounds is also useful for use in the treatment of cancers wherein tumor-specific mutated antigens are expressed. The mutated antigen could be described by identification approaches (based on exome sequencing or mass spectrometry) and classified as personalized tumor antigens. They are also a specific target for the combination of compounds according to the invention which increases cross-presentation of these antigens. MUM-1 described initially in melanoma, B-catenin, CDK4, ERBB2IP, are examples of tumor-specific mutated antigens. CEA, HER2, MUC-1, carbohydrate antigens (Tn, TF, STn), p53—a tumor suppressor gene mutated in cancers, hTERT, and WT1 are tumor-specific mutated antigens involved in breast cancers.

In another aspect, the invention relates to any combination of compounds defined here above for simultaneous, separate or sequential use in the prevention or the treatment or the vaccination of any condition or any disease susceptible of being improved or prevented. In particular, the condition or disease susceptible of being improved is a condition or a disease wherein CD47 is involved, in particular wherein CD47 is over-expressed, said condition or disease being in particular selected from the group consisting of cancer, in particular inflammatory cancer and cancer with infiltrated myeloid cells, particularly with infiltrated MDSCs and/or TAM cells, an infectious disease, a chronic inflammatory disease, an auto-immune disease, a neurologic disease, a brain injury, a nerve injury, a polycythemia, a hemochromatosis, a trauma, a sceptic shock, a chronic infectious disease, in particular *Pseudomonas* and CMV infectious disease, fibrosis, atherosclerosis, obesity, type II diabetes, melanoma and a transplant dysfunction, in particular melanoma. in particular in a cancer wherein cancer cells over-expressed CD47.

In an aspect, the invention relates to a combination product as defined above, for simultaneous, separate or sequential use in the treatment of any condition susceptible of being improved or prevented by differentiating monocytic myeloid-derived suppressor cells (Mo-MDSC) into non suppressive cells.

In an embodiment, the invention relates to a method of treatment of any condition susceptible of being improved or prevented by differentiating monocytic myeloid-derived suppressor cells (Mo-MDSC) into non suppressive cells in a subject in need thereof comprising administering simultaneously, separately or sequentially to said subject an effective amount of a combination product as defined above, said subject being SIRPa v1-positive.

In an embodiment, the invention relates to the use of a combination product as defined above in the manufacture of a medicament for the treatment any condition susceptible of being improved or prevented by differentiating monocytic myeloid-derived suppressor cells (Mo-MDSC) into non suppressive cells, said subject being SIRPa v1-positive.

In an aspect, the invention relates to a combination product as defined above, for simultaneous, separate or sequential use in the treatment of any condition susceptible of being improved or prevented by modifying macrophage polarization to pro-inflammatory macrophages.

In an embodiment, the invention relates to a method of treatment of any condition susceptible of being improved or prevented by modifying macrophage polarization to pro-inflammatory macrophages in a subject in need thereof comprising administering simultaneously, separately or sequentially to said subject an effective amount of a combination product as defined above, said subject being SIRPa v1-positive.

In an embodiment, the invention relates to the use of a combination product as defined above in the manufacture of a medicament for the treatment of any condition susceptible of being improved or prevented by modifying macrophage polarization to pro-inflammatory macrophages.

In an aspect, the invention relates to a combination product as defined above, for simultaneous, separate or sequential use in the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction or for use in vaccination.

In an embodiment, the invention relates to a method of treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction of a subject in need thereof comprising administering simultaneously, separately or sequentially to said subject an effective amount of a combination product as defined above.

In an embodiment, the invention relates to the use of a combination product as defined above, in the manufacture of a medicament for the treatment of a pathology selected from the group consisting of a cancer, an infectious disease, a chronic inflammatory disease, an auto-immune disease, a neurologic disease, a brain injury, a nerve injury, a polycythemia, a hemochromatosis, a trauma, a sceptic shock, a chronic infectious disease (such as with *Pseudomonas* or CMV), fibrosis, atherosclerosis, obesity, type II diabetes and a transplant dysfunction or for use in vaccination.

The invention also relates to any combination of compounds as such described herein.

The invention also relates to an in vitro or ex vivo method of assisting a clinician in a decision to treat a patient with an anti-human SIRPa antibody or antigen-binding fragment thereof or an antigen-binding antibody mimetic or a modified antibody, more particularly wherein an anti-human SIRPa v1 antibody or antigen-binding fragment thereof or antigen-binding antibody mimetic or modified antibody is to be administered to the patient, said method comprising the determination of the presence of SIRPa v1 in a biological sample previously obtained from the patient, said SIRPa v1 being in particular detected by an anti-human SIRPa v1 antibody as defined herein, or produced as defined herein, or a compound selected according to methods disclosed herein, and wherein the presence of SIRPa v1 in the biological sample is indicative that the treatment is likely to be effective.

The invention also relates to an antibody, an antigen-binding fragment thereof, an antigen-binding antibody mimetic or a modified antibody for use in in the treatment or the prevention of a condition wherein the patient receiving the treatment is SIRPa v2-positive, a method for producing and or selecting an anti-SIRPa v2 antibody, or antigen-binding fragment thereof or antigen-binding antibody mimetic or modified antibody. Such an antibody, an antigen-binding fragment thereof, an antigen-binding antibody mimetic or a modified antibody for use inhibits the binding of human CD47 to human SIRPa v2 and does not prevent or inhibit the binding of human CD47 to human SIRPa v1, and in particular does not prevent or inhibit the binding or human CD47 to human SIRPg. Such an antibody, antigen-binding fragment thereof, antigen-binding antibody mimetic or modified antibody may have the same binding capabilities as anti-human SIRPa v1 compounds described in the present invention, except these capabilities are related to its binding to human SIRPa v2. Moreover, such an anti-human SIRPa v2 compound may have at least one of the following features, in particular a plurality, in particular all the following features:

it binds with human SIRPa v2 with an affinity (KD) of at least 10E-8 M, in particular at least 10E-9 M, more preferably at least 10E-10 M; and/or
  it decreases or inhibits the binding of human CD47 to human SIRPa v2; and/or
  it does not prevent or inhibit the binding of human CD47 to human SIRPa v1; and/or
  it does not inhibit the human T cell proliferation; and/or
  it does not inhibit the human T cell activation; and/or
  it enhances the activation of macrophages; and/or
  it enhances the cross-presentation of at least one antigen by antigen-presenting cells to human T cells, in particular to human CD8+ T cells.

The invention also concerns the use of a polypeptide, in particular an antigen, for the production and/or for the selection of an anti-human SIRPa v2 antibody, or antigen-binding fragment thereof or antigen-binding antibody mimetic or modified antibody for use. Accordingly, provided herein is a polypeptide useful in particular for the production of anti-human SIRPa v2 antibody, and/or for the selection and/or the production of such an antibody, and/or for testing the binding affinity of such an antibody. To this end, it is also provided a polypeptide, in particular an antigen, comprising or consisting of the epitope of human SIRPa v1 consisting of SEQ ID No: 2 (KGSPDT) or SEQ ID No: 29 (KFRKGSPDTE) or SEQ ID No: 30 (TEFKSGAGTELSVR) for use in the selection of an antibody, antigen-binding fragment thereof or antigen-binding antibody mimetic, which inhibits the binding of human CD47 to human SIRPa v2, and which does not prevent or decrease the binding of human CD47 to human SIRPa v1, in particular which does not bind specifically to human SIRPa v1, in particular which does not bind specifically to human SIRPg.

Such a polypeptide may be used like the polypeptide comprising the epitope of human SIRPa v1, either for the production and/or for the selection of anti-human SIRPa v2 compound. The invention also related to a polynucleotide encoding such a polypeptide, as detailed for SIRPa v1. The combinations of compounds may comprise such an anti-human SIRPa v2 compound instead of the anti-human SIRPa v1 compound. The ex vivo or in vivo methods of assessing the likelihood of effectiveness of a treatment may be directed to the detection of SIRPa-v2 positive subject, or to the detection of SIRPa v2, for example by using an anti-human SIRPa v2 compound, or by detecting a SIRPa v2 allele as defined herein.

The invention also concerns a pharmaceutical composition comprising an antibody, or antigen-binding fragment thereof, or antigen-binding antibody mimetic or modified antibody for use according to the invention (also referenced as an anti-human SIRPa compound), or a combination of compounds comprising an anti-SIRPa compound as described herein; said pharmaceutical composition comprising a pharmaceutical vehicle, wherein said pharmaceutical composition optionally further comprises a different active ingredient. Hence, A pharmaceutical composition is also provided, said pharmaceutical composition comprising at least an antibody, an antigen-binding fragment thereof, an antigen-binding antibody mimetic or a modified antibody and at least one pharmaceutically acceptable or compatible ingredient. The term "pharmaceutically acceptable or compatible ingredient" refers to a pharmaceutically acceptable diluent, adjuvant, excipient, or vehicle with which an anti-human SIRPa antibody, an antigen-binding fragment thereof, an antigen-binding antibody mimetic or a modified antibody may be administered. The pharmaceutical composition may be administered by local administration, in particular subcutaneous administration, intro-tumoral administration.

An antibody, an antigen-binding fragment thereof, an antigen-binding antibody mimetic or a modified antibody for use according to the invention may be administered by injection, by means of a catheter, by means of a suppository, or by means of an implant, the implant being of a porous, non-porous, or gelatinous material, including a membrane, such as a sialastic membrane, or a fiber, in particular for long-term delivery. In other embodiments, an antibody, an antigen-binding fragment thereof, an antigen-binding antibody mimetic or a modified antibody for use according to the invention may be delivered in a controlled release system. In other embodiments, an antibody, an antigen-binding fragment thereof, an antigen-binding antibody mimetic or a modified antibody for use according to the invention can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, typically in purified form, together with a suitable amount of carrier so as to provide the form for proper administration to the patient.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-human SIRPa v1 binding compound (e.g., an antibody or derivative) in lyophilized form and (b) a second container containing a pharmaceutically acceptable diluent (e.g., sterile water) for injection. The pharmaceutically acceptable diluent can be used for reconstitution or dilution of the lyophilized anti-human SIRPa v1 compound. Optionally associated with such container(s) can be a notice in the form prescribed by a governmental agency regulating the manufacture, use or sale of pharmaceuticals or biological products, which notice reflects approval by the agency of manufacture, use or sale for human administration. Alternatively, the kit may be suitable for local administration, in particular subcutaneous administration or oral administration, and therefore comprising a pre-filled container, like a pre-filled syringe, or a needle-free device, like a vial, in particular when the composition is to be administered subcutaneously or orally respectively.

The amount of the anti-human SIRPa compound (e.g., antibody or derivative) that is effective in the treatment or prevention of a disease or for vaccination against a disease can be determined by standard clinical techniques.

The invention is also related to the anti-SIRPa compound for use according to the invention in combination with another therapeutic or prophylactic treatment, in particular in combination with radiotherapy, chemotherapy, immunotherapy, Indoleamine 2,3-dioxygenase (IDO) stimulators or inhibitors, STimulator of INterferon Genes (STING) agonists, pro-apoptotic cancer drugs, antiangiogenic cancer drugs.

In a particular embodiment of the invention, the anti-SIRPa compound for use according to the invention is provided in combination with a neo-antigen or a neo-epitope, wherein the anti-SIRPa compound enhance the cross-presentation of said neo-antigen or said neo-epitope by Antigen Presenting Cells to human T cells, in particular to human CD8+ T cells. Neo-antigens and neo-epitopes may be identified or detected within a tumor by methods know in the art.

The invention also concerns a method for assessing the likelihood of effectiveness of a treatment with an anti-human SIRPa v1 antibody or antigen-binding fragment thereof, or modified antibody thereof, within a human subject, said method comprising:
  the determination of the presence of human SIRPa v1 in a biological sample previously obtained from the human subject; and when the human subject is SIRPa v1-positive;
  the administration of a therapeutic amount of: an anti-SIRPa antibody or antigen-binding fragment thereof, or modified antibody thereof, disclosed herein; or of any combination disclosed herein; or any compound disclosed herein.

Such a method is particularly of interest when the human subject has been diagnosed with a cancer or is likely to develop a cancer. In a preferred embodiment, the treatment with an anti-SIRPa antibody or antigen-binding fragment hereof a modified antibody thereof is likely to be effective when the human subject has at least one SIRPa v1 allele, i.e. when the biological sample from the human subject is SIRPa v1-positive.

The determination of the presence of SIRPa v1 in a biological sample from a subject may be performed by any known method known in the art allowing the determination of the alleles encoding SIRPa in a human subject. Such methods are for example but not limited to cell sorting like FACS, genotyping, gene sequencing, in situ hybridization, Western blot, ELISA, and the like.

The invention also concerns the following embodiments:
1. An anti-human SIRPa antibody or antigen-binding fragment thereof or antigen-binding antibody mimetic or modified antibody, which comprises:
   a) a heavy chain variable domain comprising HCDR1, HCDR2 and HCDR3, wherein:
   HCDR1 comprises or consists of the amino acid sequence set forth in SEQ ID No: 9,
   HCDR2 comprises or consists of the amino acid sequence set forth in SEQ ID No: 10 or SEQ ID No: 11,
   HCDR3 comprises or consists of the amino acid sequence set forth in SEQ ID No: 12, or SEQ ID No: 13, or SEQ ID No: 14 or SEQ ID No: 15;
   and
   b) a light chain variable domain comprising of the amino acid sequence set forth in SEQ ID No: 16 or in SEQ ID No: 17;
   wherein the anti-human SIRPa antibody or antigen-binding fragment thereof or antigen-binding antibody mimetic inhibits the binding of human CD47 to human SIRPa v1, and which does not prevent or inhibit the binding of human CD47 to human SIRPa v2;
   for use in the prevention and/or treatment of a disease in a subject that is SIRPa v1 positive.
2. The anti-human SIRPa antibody or antigen-binding fragment thereof or antigen-binding antibody mimetic for use according to embodiment 1,
   wherein the heavy chain variable domain comprises or consists of the amino acid sequence set forth in SEQ ID No: 18, or in SEQ ID No: 19, or in SEQ ID No: 20; or in SEQ ID No: 21; or in SEQ ID No: 22; or in SEQ ID No: 23; in particular the heavy chain variable domain comprises or consists of the amino acid sequence set forth in SEQ ID No: 20;
wherein the light chain variable domain comprises or consists of the amino acid sequence set forth in SEQ ID No: 17

3. The anti-human SIRPa antibody or antigen-binding fragment thereof or antigen-binding antibody mimetic or modified antibody for use according to embodiment 1 or 2, wherein the disease is selected from the group consisting of an infectious disease, a chronic inflammatory disease, an auto-immune disease, a neurologic disease, a brain injury, a nerve injury, a polycythemia, a hemochromatosis, a trauma, a sceptic shock, a chronic infectious disease, in particular *Pseudomonas* and Cytomegalovirus infectious disease, fibrosis, atherosclerosis, obesity, type II diabetes, and a transplant dysfunction.

4. The anti-human SIRPa antibody or antigen-binding fragment thereof or antigen-binding antibody mimetic or modified antibody for use according to embodiment 1 or 2, wherein the disease is selected from the group consisting of a cancer, in particular inflammatory cancer and cancer with infiltrated myeloid cells, particularly with infiltrated MDSCs and/or TAM cells, melanoma, or wherein the use according to claim 1 or 2 is for therapeutic vaccination against one of these diseases, in particular a therapeutic vaccination against melanoma.

5. The anti-human antibody or antigen-binding fragment thereof or antigen-binding antibody mimetic or modified antibody for use according to embodiment 4, wherein the disease is a cancer, and wherein at least one antigen selected from the group consisting of antigens from Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, Cytomegalovirus, or from the group of single-point mutated antigens derived from the group consisting of the antigens of ctnnb1 gene, casp8 gene, her2 gene, p53 gene, kras gene, nras gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), is expressed or has been detected in the subject.

6. The human anti-SIRPa antibody or antigen-binding fragment thereof or antigen-binding antibody mimetic for use according to any one of embodiments 1 to 5, wherein the antibody is administered to a SIRPa v1 positive-subject presenting a disease wherein CD47 is over expressed in cells, in particular in cancer cells, in particular in a cancer wherein CD47 is over expressed by cancer cells.

7. The human anti-SIRPa antibody or antigen-binding fragment thereof or antigen-binding antibody mimetic for use according to any one of embodiments 1 to 6, which has the following properties:
it does not bind specifically to human SIRPa v2; and
it does not inhibit the binding of human CD47 to human SIRPg;
and optionally at least one of the following properties:
it binds with human SIRPa v1 with an affinity of at least 1E-9 M; and/or
it does not bind specifically to human SIRPg; and/or
it does not inhibit the activation and/or the proliferation of human T cells in vivo; and/or
it enhances the activation of macrophages; and/or
it enhances the cross-presentation of at least one antigen by Antigen Presenting cells to human T cells, in particular to human CD8+ T cells.

8. Use of a polypeptide, in particular use of an antigen comprising or consisting of the epitopes of human SIRPa v1 consisting of SEQ ID No: 1 or SEQ ID No: 4 or SEQ ID No: 25, in particular further comprising at least one of the epitopes of human SIRPa v1 consisting of SEQ ID No: 5 and/or SEQ ID No: 6 [linear epitopes]; and/or SEQ ID No: 7 and/or SEQ ID No. 8 [conformational epitopes], in the production or in the selection of an anti-human SIRPa v1 antibody or an antigen-binding fragment thereof or an antigen-binding antibody mimetic or modified antibody which binds specifically to human SIRPa v1, and which inhibits the binding of human CD47 to human SIRPa v1 and which does not prevent or inhibit the binding of human CD47 to human SIRPa v2.

9. Use of a polynucleotide encoding an antigen of human SIRPa v1, said isolated polynucleotide encoding an epitope of human SIRPa v1 comprising the amino acid residues of SEQ ID No: 1, SEQ ID No: 4 or SEQ ID No: 25, in particular further comprising at least one epitope of human SIRPa v1 comprising or consisting of the amino acid residues of SEQ ID No: 5 and/or SEQ ID No: 6 [linear epitopes], and/or SEQ ID No: 7 and/or SEQ ID No. 8 [conformational epitopes]., for the production of a polypeptide according to embodiment 8, in particular an antigen.

10. A method of preparing an anti-human SIRPa v1 antibody, said method comprising immunizing a non-human animal, in particular a non-human mammal, with at least one antigen as defined in embodiment 9 or with at least one antigen comprising or consisting of the epitope of human SIRPa v1 consisting of SEQ ID No: 1, SEQ ID No: 4 or SEQ ID No: 25; and in particular collecting the resulting serum or B cells from said immunized non-human animal to obtain antibodies directed against said antigen, in particular wherein the antigen comprises or consists of the epitopes of human SIRPa v1 consisting of SEQ ID No: 1 or SEQ ID No: 4 or SEQ ID No: 25, and at least one of the epitopes of human SIRPa v1 consisting of SEQ ID No: 5; and/or of SEQ ID No: 6; and/or of SEQ ID No: 7 and/or of SEQ ID No: 8.

11. A method of increasing the cross-presentation of an antigen by antigen presenting cells, in particular dendritic cells, to T cells, in particular to CD8+ T cells, said method comprising the administration to a subject of a compound selected from the group consisting of anti-human SIRPa antibody or antigen-binding fragment thereof or antigen-binding antibody mimetic or modified antibody, said compound having at least the following properties:
1. It does not specifically bind to human SIRPa v2; and
2. It binds to human SIRPa v1 with an affinity of at least 1E-9 M; and
3. It decreases or inhibits the binding of human CD47 to human SIRPa v1; and
4. It does not prevent of inhibit the binding of human CD47 to SIRPa v2; and optionally said compound having optionally at least one of the following properties:
i) It does not inhibit the T cell proliferation; and/or
ii) It does not inhibit the T cell activation; and/or
iii) It enhances the activation of macrophages; and/or
iv) It does not prevent or inhibit the binding of human CD47 to human SIRPg.

12. An in vitro or ex vivo method of assisting a clinician in a decision to treat a patient with an anti-human SIRPa antibody or antigen-binding fragment thereof or an antigen-binding antibody mimetic or a modified antibody, more particularly wherein an anti-human SIRPa v1 antibody or antigen-binding fragment thereof or antigen-binding antibody mimetic or modified antibody is to be administered to the patient, said method comprising the determination of the presence of SIRPa v1 in a biological sample previously obtained from the patient, said SIRPa v1 being in particular detected by an anti-human SIRPa v1 antibody as defined in the present invention, or produced as defined in the present invention, or a compound selected according to the present invention, and wherein the presence of SIRPa v1 in the biological sample is indicative that the treatment is likely to be effective.

13. The method according to embodiment 10 wherein the recovered anti-human SIRPa v1 antibody binds specifically to human SIRPa v1 with an affinity of at least 1E-9 M and which does not specifically bind to human SIRPa v2, in particular wherein the recovered anti-human SIRPa v1 antibody is an antagonist of the binding of human CD47 to human SIRPa v1 and does not prevent or inhibit the binding of human CD47 to human SIRPa v2 and human SIRPg.

14. A method of selecting and recovery a compound from the group consisting of an antibody, an antigen-binding fragment thereof or an antigen-binding antibody mimetic or modified antibody, said method comprising at least the following steps:
a) Testing the capability of the compound to bind specifically to human SIRPa v1, and
b) Testing the capability of the compound to decrease or inhibit the binding of human CD47 to human SIRPa v1; and
c) Testing the capability of the compound not to prevent or inhibit the binding of human CD47 to human SIRPa v2; and
d) Testing the capability of the compound to bind to amino acid residues D and V located respectively on positions 130 and 132 of SIRPa of SEQ ID No: 3; or located respectively on positions 100 and 102 of SIRPa of SEQ ID No: 25 and optionally:
e) Testing the capability of the compound not to bind specifically to human SIRPa v2; and/or
f) Testing the capability of the compound not to bind specifically to human SIRPg; and/or
g) Testing the capability of the compound not to prevent or inhibit the binding of human CD47 to human SIRPg, wherein the recovered compound has the following properties:
1. It binds specifically to human SIRPa v1;
2. It decreases or inhibits the binding of human CD47 to human SIRPa v1; and
3. It does not prevent or inhibit the binding of human CD47 to human SIRPa v2;

and optionally at least one of the following properties:
4. It does not prevent or inhibit the binding of human CD47 to human SIRPg; and/or
5. It binds to human SIRPa v1 with an affinity of at least 1E-9 M; and/or
6. It does not specifically bind to human SIRPg; and/or
7. It does not specifically bind to human SIRPa v2.

15. The method of selecting and recovery a compound according to embodiment 14 further comprising at least one of the following steps:
v) Testing the T cell proliferation in presence of the compound; and/or
vi) Testing the T cell activation in presence of the compound; and/or
vii) Testing the macrophage activation in presence of the compound; and/or
viii) Testing the cross-presentation of an antigen, in particular a tumor antigen, in particular Melan-A melanoma tumor-associated antigen (TAA), by antigen presenting cells, in particular dendritic cells, to human T cells in presence of the compound, in particular the cross-presentation of the antigen by dendritic cells to human CD8+ T cells, wherein the recovered compound has at least one of the following properties:
1. It does not inhibit the human T cell proliferation; and/or
2. It does not inhibit the human T cell activation; and/or
3. It enhances the activation of macrophages; and/or
4. It enhances the cross-presentation of an antigen by antigen presenting cells to human T cells.

16. An in vitro or ex vivo method of diagnosis of the severity of a disease in a human subject, in particular a method of diagnosis suitable for the use in personalized medicine, wherein an anti-human SIRPa antibody or antigen-binding fragment thereof or antigen-binding antibody mimetic as defined in any embodiment of the present invention, or produced as defined in the present invention, or a compound selected according to the present invention, is used for the detection of SIRPa positive cells in a biological sample previously obtained from a subject, and wherein the expression of SIRPa v1 is optionally quantified.

17. An in vitro or ex vivo method of diagnosis of the severity of a disease in a human subject, in particular a method of diagnosis suitable for the use in personalized medicine, wherein an anti-human SIRPa antibody or antigen-binding fragment thereof or antigen-binding antibody mimetic as defined in any embodiment of the present invention, or produced as defined in any embodiment of the present invention, or a compound selected according to any embodiment of present invention, is used for the detection of SIRPa positive cells in a biological sample previously obtained from a subject, and wherein the expression of SIRPa v1 is optionally quantified.

18. A composition comprising the antibody, antigen-binding fragment thereof, antigen-binding antibody mimetic or modified antibody for use according to any one of the embodiments 1 to 7, and at least one pharmaceutical vehicle.

19. A kit comprising the antibody, antigen-binding fragment thereof, antigen-binding antibody mimetic or modified antibody for use according to any one of the embodiments 1 to 7 and 18, and a device suitable for a local administration, in particular a subcutaneous or oral delivery device, in particular a device comprising a pre-filled syringe, or in particular a needle-free device.

20. A combination of compounds comprising an antibody according to any one of embodiments 1 to 7, or produced according any embodiment disclosed herein or a compound selected according any embodiment disclosed herein, and at least one antigen issued or derived from the group consisting of the antigens of Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, Cytomegalovirus, or from the group of single-point mutated antigens derived from the group consisting of the antigens of ctnnb1 gene, casp8 gene, her2 gene, p53 gene, kras gene, nras gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), for use as a medicament or as a vaccine composition, for use in the treatment or the prevention of a disease in a SIRPa v1 positive-subject.

21. An antigen-binding antibody mimetic which:
binds specifically to human SIRPa v1 and inhibits the binding of human CD47 to human SIRPa v1;
does not prevent or inhibit of human CD47 to human SIRP; and in particular does not bind specifically to human SIRPg;
for use in the treatment or the prevention of a disease, in particular a cancer, or for use in therapeutic vaccination against a disease, in particular against a cancer, wherein the antigen-binding antibody mimetic enhances the cross-presentation of an antigen expressed in said disease, in particular said cancer, and is involved in eliciting a T cell response suitable for the treatment of said disease.

22. The antigen-binding antibody mimetic for use according to embodiment 21 which is used in the prevention and/or the treatment of a disease in a subject who is SIRPa v1 positive.

23. The antigen-binding antibody mimetic for use according to embodiment 21 or 22, wherein the disease is a cancer, in particular an inflammatory cancer, a cancer with infiltrated myeloid cells, more particularly with infiltrated dendritic cells and/or MDSCs and/or TAM cells, cancer metastasis, in particular breast cancer metastasis, melanoma, or wherein the use according to embodiment 21 or 22 is for therapeutic vaccination against one of these diseases, in particular a therapeutic vaccination against melanoma.

24. The antigen-binding antibody mimetic for use according to any one of embodiment 21 to 23, which has the following properties:
It does not bind specifically to human SIRPa v2;
It does not inhibit the binding of human CD47 to human SIRPg; in particular it does not bind specifically to human SIRPg;
It binds with human SIRPa v1 with an affinity of at least 10E-9 M;
It enhances the cross-presentation of at least one antigen by Antigen Presenting Cells to human T cells, in particular by dendritic cells, in particular to human CD8+ T cells.

25. The antigen-binding antibody mimetic for use according to embodiment 24, which further has at least one of the following properties:
It does not inhibit the activation and/or the proliferation of human T cells in vivo, and/or
It enhances the activation of macrophages.

26. The antigen-binding antibody mimetic for use according to any one of embodiment 21 to 25, which further comprises at least one pharmaceutical vehicle.

27. The antigen-binding antibody mimetic for use according to any one of embodiment 21 to 26, wherein the disease is a cancer, and wherein at least one antigen selected from the group consisting of antigens from Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, Cytomegalovirus, or from the group of single-point mutated antigens derived from the group consisting of the antigens of ctnnb1 gene, casp8 gene, her2 gene, p53 gene, kras gene, nras gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), is expressed or has been detected in the subject.

28. The antigen-binding antibody mimetic for use according to any one of embodiment 21 to 27, further comprising at least one antigen issued or derived from the group consisting of the antigens of Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, Cytomegalovirus, or from the group of single-point mutated antigens derived from the group consisting of the antigens of ctnnb1 gene, casp8 gene, her2 gene, p53 gene, kras gene, nras gene, or tumor antigens, in particular tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen and ERBB2IP antigen, in particular Melan-A melanoma tumor-associated antigen (TAA), for use as a medicament or as a vaccine composition, for use in the treatment or the prevention of a disease in a SIRPa v1 positive-subject.

BRIEF DESCRIPTION OF THE DRAWINGS

FIG. 1. SIRP family sequences alignment. Alignment of membrane distal domain protein sequence of SIRPa variants v1 and v2, SIRPb and SIRPg and localization of SNPs into the protein sequence (numbered arrows from 1 to 16). Grey rectangle corresponds to the peptide signal sequences, bold underlines represent linear epitopes recognized by an anti-human SIRPa antibody, the grey dashed rectangles represent the conformational epitopes recognized by an anti-human SIRPa v1 antibody. SEQ ID NO. 32 to 35 correspond respectively to the sequences referenced in FIG. 1 as "P78328_SIRPA_HUMAN_Variant1"; "SIRPA_HUMAN_Variant"; "O00241_SIRPB_HUMAN"; and "Q9P1W8_SIRPG_HUMAN".

FIG. 4. SIRPa variants binding study using anti-human SIRPa v1 antibody and Kwar antibody by Elisa. Assessment of the binding by ELISA on immobilized SIRPa mutated variants (SIRPa from v1 to v8, see Table 2 in example 1) linked to the mouse Fc domain. Anti-human SIRPa v1 antibody and Kwar antibody (known to bind both SIRPa v1 and SIRPa v2) were compared for their ability to bind the different SIRPa mutated variants. Revelation was performed with a donkey anti-human antibody and revealed by colorimetry at 450 nm using TMB substrate. ED50 (ng/ml) is the concentration of the indicated antibody to reach 50% of the signal in this assay.

EXAMPLES

Figure 2:
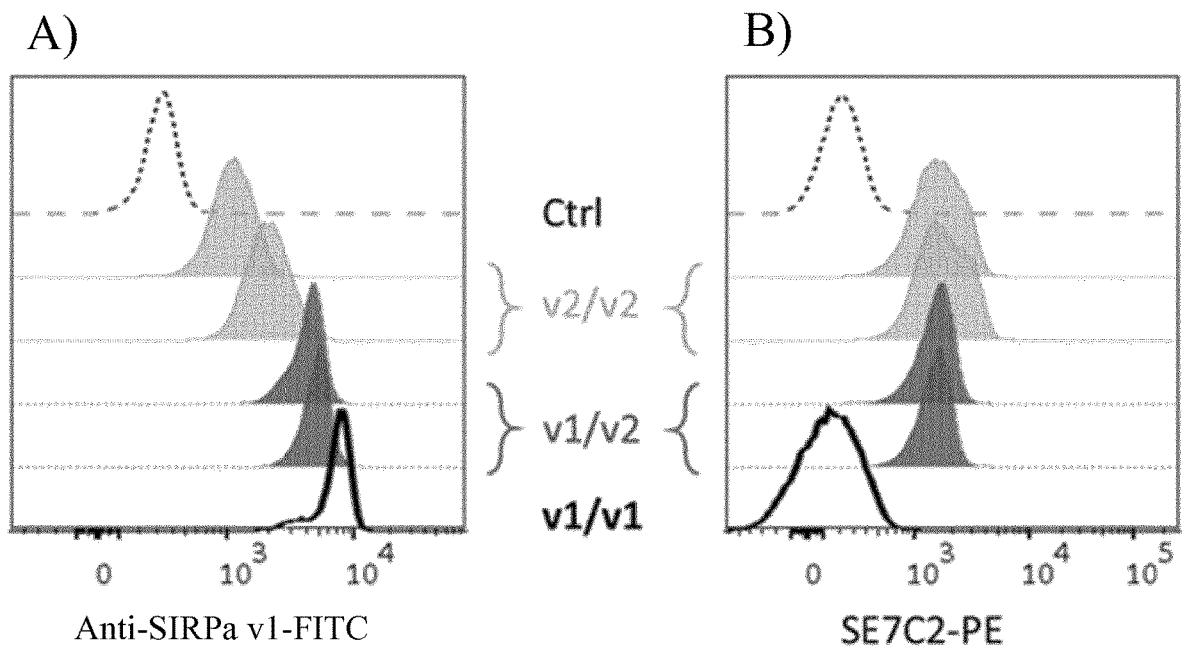
FIG. 2A B. Binding of SIRPa antibodies against human SIRPa variant V1 and V2 expressed by blood monocytes. Healthy donors already sequenced for the SIRPa exon 3 were selected. By Fluorescence-activated cell sorting (FACS), (A) the binding of in-house anti-SIRPa antibody (Anti-SIRPa vi-FITC on the left hand side of the drawing) and (B) the commercial SE7C2 (on the right hand side of the drawing), were tested on blood monocytes from donors selected from SIRPa V1/V1 and SIRPa V2/V2 homozygous as well as SIRPa V1/V2 heterozygous.

Example 1: Identification of the Epitope which Allows the Production of Anti-Human SIRPa v1 Antibodies Human SIRPa was previously described to present some level of polymorphism in IgV domain 1 which interacts with CD47. This polymorphism is mainly located in the exon 3 of SIRPa gene (SEQ ID No: 27) (Takenaka et al., 2007). On 37 different donor's genomic sequences from different origin, Takenaka et al. identified 10 different sequences/alleles, with 2 principal alleles: variant 1 (v1) and variant 2 (v2). Other alleles differ from V1 or V2 sequences by only 1 or 2 SNPs. Therefore, the SIRPa family is sub-divided into two sub-families: SIRPa v1 isoforms and SIRPa v2 isoforms. These different alleles lead to slightly different proteins, but all variants bind similarly CD47 ligand. Allelic frequency of v1 in Takenaka et al. is 78% (89% for V1 and V1-like) while genotype frequency for homozygous V1/V1-like donors is 65%. 24% of their 37 donors presented a heterozygous genotype.

Coding DNA and Protein Sequences of SIRPA V1 and V2:

V1 of human SIRPa Sequence was obtained on ncbi (gene ID: 140885).

Genomic DNA reference sequence of SIRPa v1 exon 3 (transcript SIRPA-201 ID ENST00000400068.7) (SEQ ID No: 27):

```
GAGTGGCGGGTGAGGAGGAGCTGCAGGTGATTCAGCCTGACAAGTCCGTG

TTGGTTGCAGCTGGAGAGACAGCCACTCTGCGCTGCACTGCGACCTCTCT

GATCCCTGTGGGGCCCATCCAGTGGTTCAGAGGAGCTGGACCAGGCCGGG

AATTAATCTACAATCAAAAAGAAGGCCACTTCCCCCGGGTAACAACTGTT

TCAGACCTCACAAAGAGAAACAACATGGACTTTTCCATCCGCATCGGTAA

CATCACCCCAGCAGATGCCGGCACCTACTACTGTGTGAAGTTCCGGAAAG

GGAGCCCCGATGACGTGGAGTTTAAGTCTGGAGCAGGCACTGAGCTGTCT

GTGCGCG
```

Amino acid sequence of one SIRPa v1 (Genbank reference NP_001035111.1 (UniProtKB: P78324) (SEQ ID No: 3):

```
MEPAGPAPGRLGPLLCLLLAASCAWSGVAGEEELQVIQPDKSVLVAAGET

ATLRCTATSLIPVGPIQWFRGAGPGRELIYNQKEGHFPRVTTVSDLTKRN

NMDFSIRIGNITPADAGTYYCVKFRKGSPDDVEFKSGAGTELSVRAKPSA

PVVSGPAARATPQHTVSFTCESHGFSPRDITLKWFKNGNELSDFQTNVDP

VGESVSYSIHSTAKVVLTREDVHSQVICEVAHVTLQGDPLRGTANLSETI

RVPPTLEVTQQPVRAENQVNVTCQVRKFYPQRLQLTWLENGNVSRTETAS

TVTENKDGTYNWMSWLLVNVSAHRDDVKLTCQVEHDGQPAVSKSHDLKVS

AHPKEQGSNTAAENTGSNERNIYIVVGVVCTLLVALLMAALYLVRIRQKK

AQGSTSSTRLHEPEKNAREITQDTNDITYADLNLPKGKKPAPQAAEPNNH

TEYASIQTSPQPASEDTLTYADLDMVHLNRTPKQPAPKPEPSFSEYASVQ

VPRK
```

Amino acid sequence of one SIRPa v2 (SEQ ID No: 28):

Variant 2 protein sequence was referenced in Takenaka et al., 2007. The coding DNA sequence was obtained on ncbi (GenBank: BC075849.1). No gene sequence has been found for this variant on ncbi database.

```
MEPAGPAPGRLGPLLCLLLAASCAWSGVAGEEELQVIQPDKSVSVAAGES

AILHCTVTSLIPVGPIQWFRGAGPARELIYNQKEGHFPRVTTVSESTKRE

NMDFSISISNITPADAGTYYCVKFRKGSPDTEFKSGAGTELSVRAKPSAP

VVSGPAARATPQHTVSFTCESHGFSPRDITLKWFKNGNELSDFQTNVDPV

GESVSYSIHSTAKVVLTREDVHSQVICEVAHVTLQGDPLRGTANLSETIR

VPPTLEVTQQPVRAENQVNVTCQVRKFYPQRLQLTWLENGNVSRTETAST

VTENKDGTYNWMSWLLVNVSAHRDDVKLTCQVEHDGQPAVSKSHDLKVSA

HPKEQGSNTAAENTGSNERNIYIVVGVVCTLLVALLMAALYLVRIRQKKA

QGSTSSTRLHEPEKNAREITQDTNDITYADLNLPKGKKPAPQAAEPNNHT

EYASIQTSPQPASEDTLTYADLDMVHLNRTPKQPAPKPEPSFSEYASVQV

PRK
```

Genomic DNA reference sequence of SIRPa v2 exon 3 (SEQ ID No: 31):

GAGTGGCGGGTGAGGAGGAGCTGCAGGTGATTCAGCCTGACAAGTCCGTA

TCAGTTGCAGCTGGAGAGTCGGCCATTCTGCACTGCACTGTGACCTCCCT

GATCCCTGTGGGGCCCATCCAGTGGTTCAGAGGAGCTGGACCAGCCCGGG

AATTAATCTACAATCAAAAAGAAGGCCACTTCCCCCGGGTAACAACTGTT

TCAGAGTCCACAAAGAGAGAAAACATGGACTTTTCCATCAGCATCAGTAA

CATCACCCCAGCAGATGCCGGCACCTACTACTGTGTGAAGTTCCGGAAAG

GGAGCCCTGACACGGAGTTTAAGTCTGGAGCAGGCACTGAGCTGTCTGTG

CGTGC

The amino acid sequences of the D1 domain of SIRPa v1, SIRPa v2, SIRPb and SIRPg were aligned as illustrated on FIG. 1.

Genotype Frequency Analysis by Bioinformatic

To explore more data on SIRPa polymorphism in human, Data from "1000 Genomes project" (1 KG, >2500 different human genomes) were used to identify relevant SNPs in human SIRPa exon 3. Inventors identified that SIRPa SNPs segregated in 2 haplotype blocks using Haploview (data not shown).

To explore genotype frequency and analyze the differences between homozygous and heterozygous donors, inventors first identified 18 SNPs (Table 1) within human SIRPa exon 3 (the known polymorphic exon from literature and the exon responsible of the binding with the ligand) and retained SNPs associated with a codon change (change in amino acid sequence). SNPs were numbered from 1 to 18. 1 SNP was not analyzed since not known in the literature. SNP7 and SNP18 were not analyzed either in terms of genotype frequency since both correspond to synonymous codon (no change at protein level). The inventors then identified SNPs allele and genotype frequencies with the 1000 genomes phase 3 project which includes more than 5000 donors from 5 super populations: n=1030 East Asian (EAS), n=1010 European (EUR), n=1338 African (AFR), n=704 Ad Mixed American (AMR) and n=988 South Asian (SAS). All individuals from 1000 genomes phase 3 project are being considered.

TABLE 1

SNPs identification on SIRPa variants and their amino acid positions

| | Nucleotide mutations (SIRPa v1 - SIRPA v2) | Amino acid position and mutations (SIRPa v1 - SIRPA v2) | Rs number |
|---|---|---|---|
| SNP1 | g-a | 44 L-S | rs386811660 |
| SNP2 | a-t | 50 T-S | rs17855609 |
| SNP3 | a-g | 51 A | rs17853846 |
| SNP4 | c-t | 52 T-I | rs17855610 |
| SNP5 | g-a | 54 R-H | rs17855611 |
| SNP6 | c-t | 57 A-V | rs17855612 |
| SNP7 | t-c | 60 L | rS17853847 |
| SNP8 | g-c | 75 G-A | rs1057114 (=rs72620874) |
| SNP9 | c-g | 95 D-E | rs138283486 |
| SNP10 | c-t | 96 L-S | rs149634649 |
| SNP11 | t-c | 97 T | rs146163282 |
| SNP12 | a-g | 100 N-E | rs17855613 |
| SNP13 | c-a | 101 N | rs17855614 |
| SNP14 | c-a | 107 R-S | rs17855615 |
| SNP? | g-a | 109 G-S | |
| SNP15 + SNP16 | gt - ac | 132 V - T | rs115287948 rs114499682 |
| SNP17 = (SNP15 + SNP16) | gt - ac | 132 V - T | s386811663 |
| SNP18 | c - t | 145 R | rs6136375 |

Then, inventors clustered physically neighbouring SNPs with roughly similar frequency (<1% difference) and plotted mean frequencies of these clustered SNPs on Pie Chart according to population genetics. They finally performed a correlation with in-house anti-human SIRPa v1 antibody epitope (since it displays low binding on V2/V2 donors and poorly block CD47 binding on V2/V2, data not shown) determined by two methods (linear or conformational methods). They also took into consideration SNPs associated with a mutation in SIRP gamma (since in-house antibody does not bind to SIRP gamma). Finally, inventors also reinforced this analysis by comparing sequence differences between human SIRPa V1, human SIRPa V2 and mutations found in cynomolgus (*Macaca fascicularis*) or rhesus (*Macaca mulatta*) monkeys since the in-house antibody has no cross-reactivity with monkey.

Anti-SIRPa Binding Relationship with SNPs:

Method: The binding activity of the anti-SIRPa antibodies was assessed by ELISA. For the ELISA assay, the in-house anti-human SIRPa v1 antibody and Kwar antibody were tested on 8 different mutated hSIRPa (SIRPA v1 to v8; see table 2). The different variants of mutated hSIRPa (SIRPa v1 to v8) were immobilized on plastic at 0.5 µg/ml in carbonate buffer (pH9.2) and the purified antibody was added to measure binding. After incubation and washing, peroxidase-labeled donkey anti-human IgG (Jackson Immunoresearch; USA; reference 709-035-149) was added and revealed by conventional methods.

Results: In order to evaluate the impact of human SIRPa SNPs on the in-house anti-human SIRPa v1 antibody binding capabilities, 8 different recombinant human SIRPa proteins were generated (Table 2). The extracellular domains of these SIRPa proteins were fused with mouse Fc from IgG2a, and the binding capability of the in-house anti-human SIRPA v1 antibody to those SIRPa variants was assessed (FIG. 4). The in-house antibody loses its binding property in ELISA when SNPs 15+16 are mutated in the V1 sequence (FIG. 4A). In the experiments disclosed in the present application, the anti-human SIRPa v1 antibody used corresponds to an antibody with a heavy chain variable domain comprising or consisting of the amino acid sequence of SEQ ID No: 20; and a light chain variable domain comprising or consisting of the amino acid sequence of SEQ ID No: 17. Other SNPs mutation did not alter the in-house antibody binding property. In comparison, KWAR23 (which is described to bind both V1 and V2) binding properties were not modified with any one of the SNPs mutations (FIG. 4B), confirming that SIRPa V8 (SNPs15+16) protein is functional and that an antigen comprising an epitope localized in the surrounding of SNPs 15+16 allows the production of anti-SIRPa v1 antibodies which do not recognize or bind specifically to SIRPa v2.

TABLE 2

| SIRPa recombinant proteins |
| --- |
| SIRPa V1 |
| SIRPa V2 |
| SIRPa V3 (SNP1 + 2 + 3 + 4 + 5 + 6) |
| SIRPa V4 (SNP8) |
| SIRPa V5 (SNP9 + 10 + 11) |
| SIRPa V6 (SNP12 + 13) |
| SIRPa V7 (SNP14 + ?) |
| SIRPa V8 (SNP15 + 16) |

Impact of SIRPA Polymorphism on Antibodies Properties—Antagonist Assay SIRPA-Cd47 by FACS on Monocytes METHOD: Human monocytes (purified by elutriation from human PBMC at DTC platform, Nantes, and frozen in DMSO at 10M/ml at −80° C. or liquid nitrogen) were thawed in 40 mL complete RPMI medium. Then immediately centrifuged at 1000 rpm during 10 minCells are resuspended in 10 mL of RPMI medium and counted on Malassez cell. Frozen human monocytes are thawed, diluted samples are added and biotinylated CD47Fc is added afterwards. Biotinylated CD47Fc is then revealed with a streptavidin-PE and fluorescence is measured by flow cytometry. The following protocol was applied: —Put 100,000 human monocytes per well on V-bottom P96 plate; —Centrifuge 1 min at 2500 rpm and empty wells by flicking the plate; —Wash cells 2 times with 200 μL PSE (Centrifuge 1 min at 2500 rpm and empty wells); —Prepare 8 dilutions of the sample beginning with 10 μg/mL (concentrated 2×, final concentration 5 μg/mL) and diluting by steps of 3; —Add 12.5 μL of sample/well on cells and mix; —Incubate 15 min on ice; —Prepare CD47Fc biotinylated solution concentrated 2×, determined in function of paragraph and add 12.5 μL of this solution/well on cells and mix.—Incubate 30 min on ice; —Add 175 μL PSE/w-Centrifuge 1 min at 2500 rpm and empty wells; —Wash cells 2 times with 200 μL PSE (Centrifuge 1 min at 2500 rpm and empty wells). An intermediate concentration is chosen for CD47Fc biotinylated. Here, 5 μg/mL CD47Fc biotinylated are took for the antagonist test. This step has to be made each time because percentage of CD47 positive cells depends of individual donor; —Dilute streptavidin-PE at 1/1000, Add 25 μL/w-Incubate 15 min on ice; —Add 175 μL PSE/w; —Centrifuge 1 min at 2500 rpm and empty wells; —Wash cells 2 times with 200 μL PSE (Centrifuge 1 min at 2500 rpm and empty wells); —Transfer stained cells in V-bottom P96 canto plate and read on BD canto II.

Figure 3:
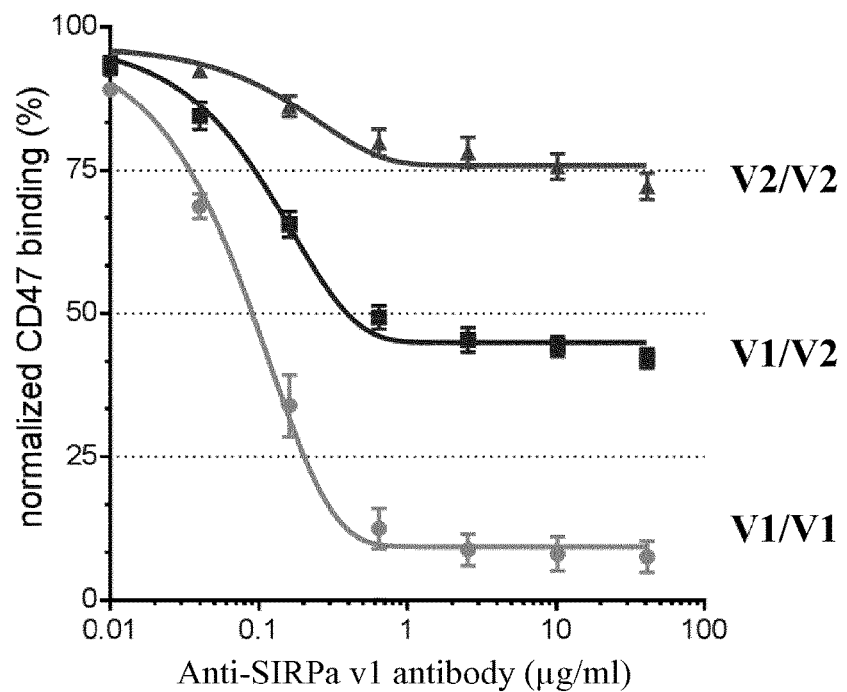
FIG. 3. Antagonist activity of an anti-human SIRPa v1 antibody on blood monocytes from donors that are SIRPa v1/v1 homozygous donors, SIRPa v1/v2 heterozygous donors or SIRPa v2/v2 homozygous donors. Competition assay by FACS of one anti-human SIRPa v1 antibody on the SIRPa-CD47 interaction using homozygote or heterozygote donor cells. A dose response of anti-human SIRPa v1 antibody was used to compete with the binding of CD47 to SIRPa variants from different donors. The percentage of the CD47 binding are normalized to the control, and results are represented for each cell donors: V2/V2 homozygote (triangle), V1/V2 heterozygote (square) and homozygote V1/V1 (circle).

RESULTS: Inventors analyzed the binding properties of the in-house anti-SIRPa v1 antibody by flow cytometry on blood monocytes from healthy donors already sequenced for the SIRPa exon 3 (FIG. 2). They selected V1/V1 homozygous donors, V2/V2 homozygous donors as well as V1/V2 heterozygous donors. FIG. 3 shows that the anti-human SIRPa v1 antibody binds significantly less on V2/V2 donors. In comparison, the inventors found that a commercial anti-SIRPa mAb (clone SE7C2) binds only the V2 protein. SE7C2 data show that V2/V2 donors express similar level of SIRPa protein at their surface as compared to V1/V2 donors, confirming that reduced binding of the anti-human SIRPa v1 antibody on V2/V2 is not due to lower expression but low binding of this antibody to this SIRPa v2 protein (FIG. 2).

Then the inventors analyzed by flow cytometry the in-house anti-human SIRPA v1 antibody antagonist property to prevent the binding of recombinant human CD47 protein binding on blood monocytes from healthy donors (FIG. 3). To study the impact of SIRPa polymorphism on the antagonistic effect on the binding of CD47-Fc, an antagonistic assay was performed on frozen human monocytes genotyped for SIRPa. The data illustrated on FIG. 3 show that the anti-human SIRPa v1 antibody greatly antagonizes CD47 binding on V1/V1 donors (n=3) while it only reduces by half CD47 binding on heterozygous V1/V2 donors (n=5). Weak (25%) antagonist action of the anti-human SIRPa v1 antibody is observed on homozygous V2/V2 donors (n=3). As shown on FIG. 3, the in-house antibody recognized SIRPa V1 and very weakly recognized SIRPa V2. It indicates that the in-house antibody has a strong antagonistic effect on binding of CD47-Fc on human monocytes which were homozygous V1/V1 for SIRPa, a very weak antagonistic effect on homozygous V2/V2 human monocytes, and an intermediary antagonistic effect on heterozygous V1/V2 human monocytes.

Conclusion

Figure 6:
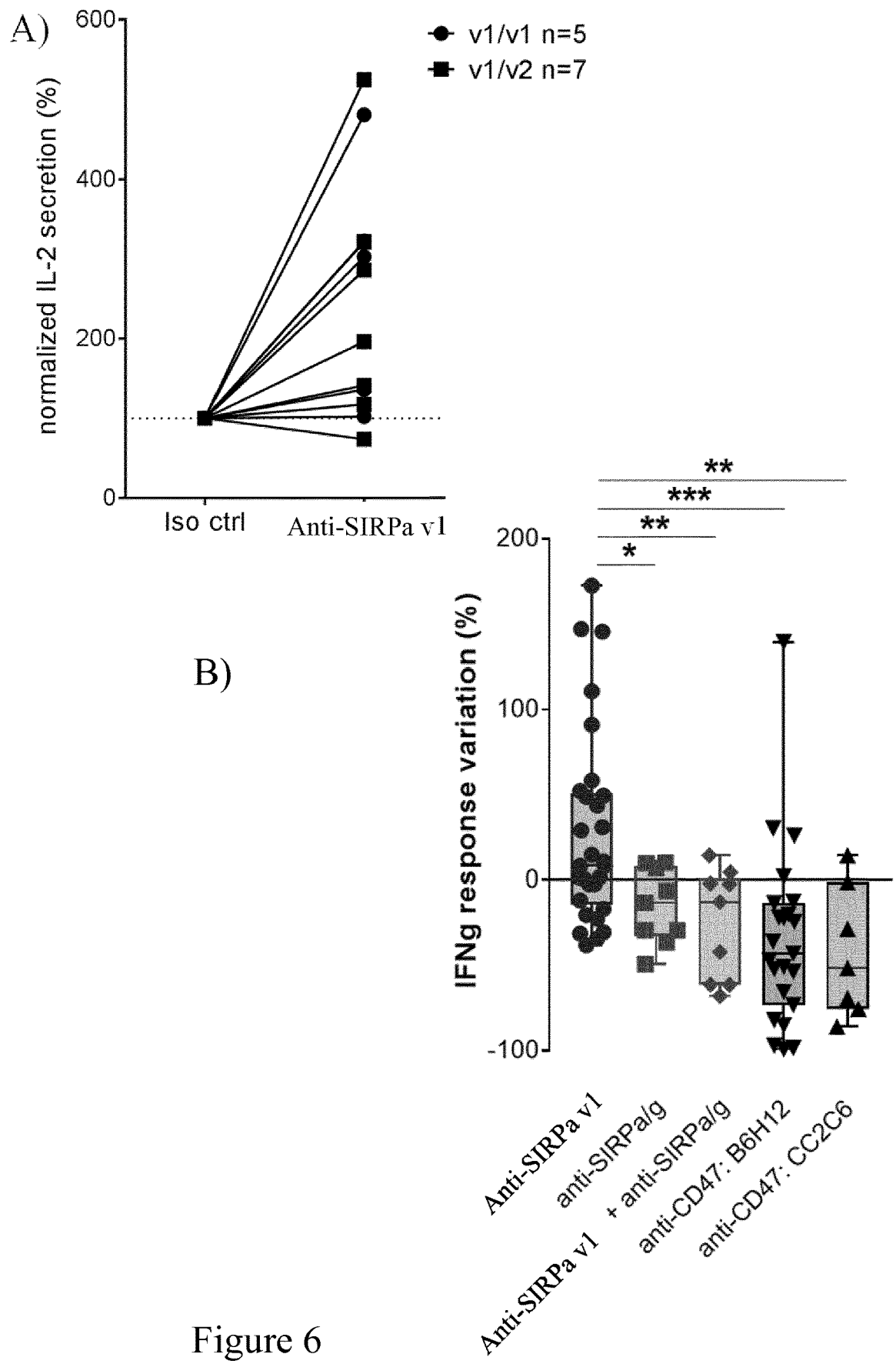
FIG. 6. Human antigen cross presentation by dendritic cells. Monocytes from HLA-A2+ HV were phenotyped for SIRPa and both homozygous (v1/v1) and heterozygous (v1/v2) monocytes were used in two type of experiments. A. IL-2 expression in CD8+ T cells. Results obtained with SIRPa v1 homozygote immature DCs are represented with a round and those obtained with SIRPa v1/v2 heterozygote immature DCs with a square. Melan-A loaded immature DCs were used to activate the Melan-A/HLA-A2+ specific thymoma clone that was measured by IL-2 secretion after 48 h of culture. B. IFNg expression in CD8+ T cells stimulated with Melan-A loaded iDC. iDCs were previously incubated during the loading phase with different antibodies: anti-SIRPa v1 (round), anti-SIRPa/g (square), anti-SIRPa v1+anti-SIRPa/g (diamond), B6H12 (inverted triangle) and CC2C6 (triangle). The expression of IFNg was evaluated by flow cytometry.

Polymorphism of SIRPa was not described to affect CD47 binding but can affect recognition by anti-human SIRPa monoclonal antibodies. Multiple variants have been determined by Takenaka et al. with a high sequence homology with V1 or V2 sequences. Other variants represent different combinations between V1 and V2 sequences and can be considered as V1-like or V2-like variants depending on their majority genotype. These results were confirmed with data from 1000 genomes which show there are two major variants for SIRPa: V1 and V2. Variant 1 is the most frequent in worldwide population except in East Asian super population. The SNPs analysis in the present invention showed that SIRPa V1 allele frequencies (V1/V1 and V1/V2) relevant for the epitope allowing the production and/or the selection of anti-human SIRPa v1 antibodies is between 76-86% in the US and EU and V1/V1 homozygous patients represent between 40 and 50% of US and EU populations (based on SNPs 15 and 16 frequencies). The inventor analysis on n=184 donors showed that the in-house anti-human SIRPa v1 antibody strongly binds 83-86% of v1 donors (V1/V1 and V1/V2). V1/V1 homozygous donors represent between 40 and 50% of analyzed cohort. While CD47 antagonist assay showed in an interestingly manner that the in-house antibody prevented only half of the binding, functional assays on macrophage polarization presented on FIG. 8 and tumor-antigen cross-presentation by human dendritic cells presented FIG. 6 showed that the in-house anti-human SIRPa v1 antibody has the same biological efficacy on both V1/V1 and V1/V2 donors.

Figure 5:
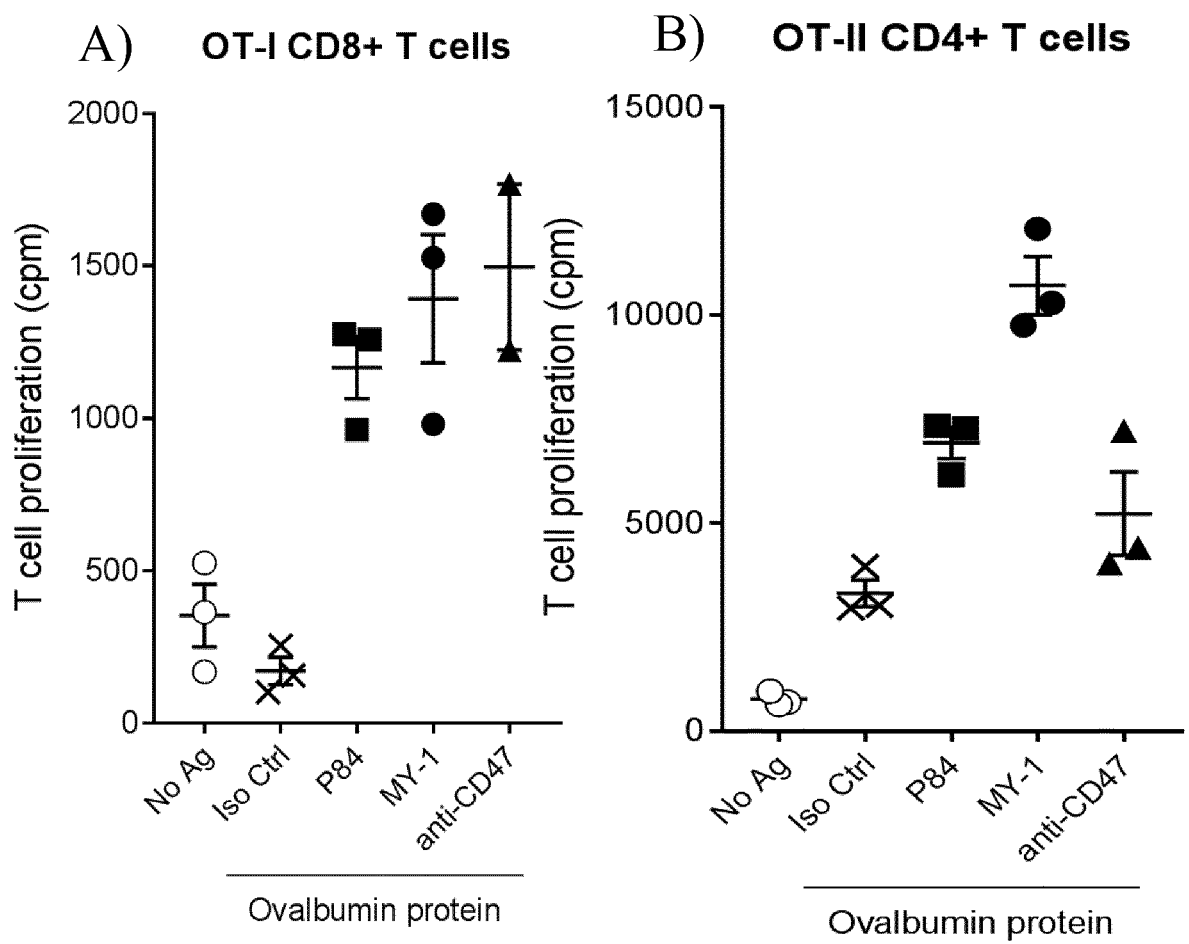
FIG. 5. Mouse antigen cross-presentation by dendritic cells (DCs). Mice DCs were preloaded with Ovalbumin antigen and then cultured with transgenic T cells from OTI or OTII mice (Transgenic for their TCR expression dedicated to OVA MHC I or II). T cell proliferation was measured by thymidine incorporation (OTI CD8+ T or OTII CD4+ T cells) in different conditions: control with no Ag (empty circle) or Isotype Antibody control (crosses), mice anti-SIRPa antibodies P84 (square) and MY1 (round) or anti-CD47 antibody (triangle). A: results obtained on OTI CD8 positive T cells. B: results obtained on OT-II CD4 positive T cells.

Example 2: Comparison of SIRPa-CD47 Interaction Blockade on Immune Cross Presentation Between Mouse and Human Mouse Cross-Presentation (FIG. 5)

DRUGS: the allosteric antagonist monoclonal antibody targeting the domain 2 of the mouse SIRPa (P84 clone—rat IgG1) was purified from hybridoma. The orthosteric antagonist monoclonal antibody targeting the domain 1 of the mouse SIRPa (MY-1 clone—mouse IgG2a) (Garcia et al., 2011) was reengineered into an IgG1 Fc domain from the parental hybridoma. Both anti-SIRPa antibodies block the signaling through SIRPa in myeloid cells. The isotype control mouse IgG1 (3G8 clone) was purified. The surrogate antagonistic anti-mouse CD47 monoclonal antibody (MIAP410 clone) was purchased from BioXCell (#BE0283).

MOUSE SIRPa EXPRESSION BY SPLENIC DCs: natural DC were isolated from the spleen of naïve mice by CD11c positive magnetic selection and separated for their CD8α expression by cell sorting with a BD FACS ARIA II. As described in the literature, CD8α+/+DC, which are the best antigen-presenting cells (APC) for cross-presentation, express low to negative levels of SIRPa while CD8α−/−DC express SIRPa (and are known to less efficiently cross-present antigens).

ANTIGEN PRESENTATION FUNCTION BY SPLENIC DCs: According to the literature, the SIRPa low/neg CD8α+/+DC are the best antigen-presenting cells (APC) for the antigen (Ag) cross-presentation compared to CD8α−/−DC (expressing high level of SIRPa) (Haan et al., 2000; Hochrein et al., 2001). However, the two subtypes of DC loaded and presented exogenous Ag on MHC class II molecules equivalently. Inventors showed that the protocol used to evaluate the role of SIRPa on Ag cross-presentation with OVA and OT-IT cells reproduces these DC's properties (data not shown). Indeed, the CD8α+/+DC induced a better proliferation of OT-I T cells (from CD8+ Ovalbumin-specific TCR-transgenic mice) than CD8α−/−DC indicating a better Ag processing, loading and presentation on MHC class I molecules whereas the exogenous antigen presentation is high for both subtypes of splenic DCs as they observed with the OT-II T cell (from CD4+ Ovalbumin-specific TCR-transgenic mice) proliferation. Thus, expression of SIRPa is inversely correlated with the capacity of dendritic cells to cross-present antigen to CD8+ T cells, suggesting that SIRPa represses cross-presentation in mice.

MOUSE ANTIGEN CROSS-PRESENTATION: CD8α+/+ and CD8α−/−DC were loaded with ovalbumin (OVA) overnight in the presence of GM-CSF. Then, CD8+ T cells isolated from the spleen of the OT-I transgenic mice and CD4+ T cells isolated from the spleen of the OT-II transgenic mice were cultured with OVA-loaded DC subtypes for 3 days. The transgenic mice express TCR specific of OVA MHC I (OT-I) and II (OT-II). Proliferation was evaluated by H3-thymidin incorporation during the last 16 hours of culture. Anti-SIRPa mAb was added at 10 μg/ml during the incubation of DC with OVA protein and during T cell proliferation with OVA-loaded DC. This protocol allows to evaluate the impact of SIRPa blockade during protein processing by DCs and then presentation of OVA peptide by the MHC class I molecules by the DC to CD8 OT-I T cells and by the MHC class II molecules to CD4 OT-II T cells highlighting the antigen cross-presentation and the exogenous antigen presentation respectively.

Inventors shows that the blockade of SIRPa or CD47 in mouse potentiated the antigen presentation by SIRPa+ splenic dendritic cells. The CD8α+/+DC (SIRPa low/neg) were not affected by the blockade of the SIRPa/CD47 pathway regarding their ability to cross-present OVA to OT-I T cells (not shown). However, the blockade of either SIRPa by P84 or MY-1 blocking antibodies or CD47 by MIAP410 enhances Ag cross-presentation by CD8α−/−SIRPa+ DC reflected by CD8+ OT-I proliferation increase (FIG. 5A).

EXOGENOUS ANTIGEN PRESENTATION: the inventors analyzed the effect of the SIRPa/CD47 blockade on exogenous Ag presentation, they found that Ag presentation by SIRPa low/neg-CD8a+/+DC was not modified by the blockade of the SIRPa/CD47 pathway (not shown). Similar to cross presentation process, SIRPa/CD47 blockade on SIRPa positive CD8a−/−DC increased exogenous antigen processing and presentation on MHC class II molecules as measured by CD4+OT-II cell proliferation (FIG. 5B).

Conclusion

Inventors demonstrated that blocking the SIRPa/CD47 pathway (with anti-SIRPa or anti-CD47 mAbs) in mouse increased both MHC-I antigen cross-presentation (T CD8 response) and MHC-II antigen presentation (T CD4 response). Those results confirmed what was suggested by others such as (Liu et al., 2016, 2015; Xu et al., 2017).

Human Cross-Presentation (FIG. 6)

DRUGS: the antagonistic monoclonal antibody targeting the human SIRPa (in-house anti-human SIRPA v1 antibody—human IgG4) was generated and purified by inventors. The isotype control human IgG4 was purchased from Biolegend (QA16A15 clone). The antagonistic monoclonal antibody targeting the human CD47 (B6H12 clone) was purchased from BioXCell (#BE0019-1) and CC2C6 clone from BioLegend (#TBD2) were used. In some experiments, the anti-SIRPa:g antibody (clone SIRP29 from WO201356352) was used alone or in combination with the in-house anti-SIRPa V1 antibody.

MELAN-A SPECIFIC RESPONSE: the cross-presentation by human cells was evaluated by the presentation of a long peptide (25-mer, which implies that the peptide cannot "dock" onto Class I MHC molecules without being processed) of the Melan-A melanoma tumor-associated antigen (TAA) by HLA-A2+ DCs to TCR-specific T cells that recognize specifically HLA-A2/Melan-A complexes. Two different TCR-specific T cells were used to evaluate the antigen cross-presentation. The first was a T lymphocyte clone from a melanoma patient which is specific for these HLA-A2/Melan-A complexes (kind gift from Dr. N. Labarrière, Univ. Nantes, France, Vignard at al., J. Immunol 2005). The second clone was a transgenic murine thymoma cell line transduced with the TCR of the same melanoma patient's T-cell clone and transfected with the human CD8 co-receptor. DCs were generated in vitro from blood monocytes of HLA-A2+ healthy volunteers (HV; volunteers from the Etablissement Français de Sang, Nantes). Meanwhile, monocytes were phenotyped for the polymorphism of SIRPa. After 7 days of culture with GM-CSF and IL-4, immature DCs (iDCs) were induced. Then iDCs were loaded overnight with the long 25-mer peptide of Melan-A in the presence of antagonistic antibodies targeting the SIRPa/CD47 pathway and finally cultured independently with the two different Melan-A/HLA-A2 specific T cell clones. The human T cell clone from the melanoma patient was cultured with Melan-A-loaded iDC for 5 hours and T cell activation evaluated by flow cytometry by intracellular staining of IFNg.

The TCR transgenic thymoma clone was cultured with Melan-A-loaded iDC for 48 hours and T cell activation was evaluated by ELISA for IL-2 secretion.

To validate the protocol, Melan-A loaded iDCs from HLA-A2 negative donors were used as a negative control, as well as unloaded-iDCs from HLA-A2+HV. Results (not shown) showed that only HLA-A2+ Melan-A loaded-iDC were able to induce IFNg secretion by the human T cell clones. The secretion of IL-2 by murine thymoma cells was only measured in HLA-A2 positive donors and compared to HLA-A2-Melan-A loaded DCs (data not shown) demonstrating the specificity of the two different HLA-A2/Melan-A specific T cell clones.

Monocytes from HLA-A2+HV were phenotyped for SIRPa and both V1 homozygous and V1/V2 heterozygous monocytes were included in 2 different experiments.

THYMOMA CELL CLONE ENGINEERED IN VITRO: after 48 hours of stimulation of the TCR-transgenic thymoma cell clone with the Melan-A loaded human iDCs, IL-2 secretion was measured. In this first read-out of the antigen cross-presentation, inventors observed an increase of IL-2 secretion by the thymoma clone in most of donors when SIRPa was blocked by a specific anti-SIRPa antibody (in-house anti-human SIRPa v1 antibody) during the loading of Melan-A and the stimulation assay (FIG. 6A). No difference was observed between V1 homozygous and V1/V2 heterozygous donors of DCs.

HUMAN T CELL CLONE FROM MELANOMA PATIENT: after 5 hours of stimulation of the CD8 human T cell clones with Melan-A loaded human iDC, the expression of IFNg was evaluated by flow cytometry. FIG. 6B represents the IFNg expression in CD8+ T cells. SIRPa or CD47 were blocked during the loading of Melan-A and during T cell stimulation. Various antibodies were tested: an anti-human SIRPa v1; an anti-SIRPa/g (SIRP29), anti-CD47 (B6H16 and CC2C6). FIG. 6B shows that SIRPa blockade by in-house anti-human SIRPa v1 antibody led to an increase of IFNg expression by tumor-antigen-specific human T-cells induced by iDC from homozygote or heterozygote donors. Interestingly, inventors showed that positive effect of SIRPa blockade on Ag presentation was not restricted to SIRPa v1 homozygous iDCs since similar increase was observed in most V1/V2 heterozygous donors. Unexpectedly, in contrast to mouse cross-presentation, inventors found in human that the two anti-CD47 mAbs had no positive impact on most donors IFNg secretion and worst strongly suppress basal level of T-cell activation in the majority of the donors. More surprisingly, an anti-SIRPa which is not SIRPa-specific but binds as well SIRPg and inhibits the binding of CD47 to SIRPg, does not induce the IFNg expression by T cells indicating that the cross presentation by iDC to T cells is specific of the in-house anti-human SIRPa v1 antibody. Unusually, the addition of the non-selective SIRPa/g antibody to the selective in-house SIRPa v1 antibody prevents increased IFNg secretion by selective blockade of SIRP alpha and not gamma. These results obtained in human with different anti-CD47 antibodies and anti-SIRPa/g antibody were not predictable regarding results in mice models and could explain some interesting results from inventors showing that polyclonal human T-cell proliferation and human mixed lymphocyte reaction were strongly inhibited in human by different anti-CD47 mAbs and anti-SIRPg (Piccio et al., 2005) but not by the specific anti-SIRPa v1 antibody of the invention.

Conclusion

The two different clones used to evaluate antigen cross-presentation showed similar results with SIRPa blockade on iDCs during Ag loading and Ag presentation to T cells. Inventors showed for the first time that the human SIRPa has an inhibitory role on antigen cross-presentation, measured by IFNg or IL2 secretion, which can be alleviated by selective anti-SIRPa mAbs. This was not predictable because the blockade of CD47 with different anti-CD47 antibodies or non-selective anti-SIRPa/g antibody did not present this effect on human T cells which find explanation by considering previous observations on the immunosuppressive properties of anti-CD47 mAbs in human but not in mouse. Previous art shows that SIRPa inhibits mouse DC maturation. For the first time, inventors disclosed that a specific anti-SIRPa antibody could be a therapeutic compound to potentiate Ag cross-presentation in human. While anti-CD47 mAbs in mouse have similar potentiating effect than mice anti-SIRPa, the effect of human anti-SIRPa on human DCs cross-presentation was not predictable. Our understanding of the immune mechanism mediated by SIRPa-CD47 interaction led us to presume that the immunosuppressive properties of anti-CD47 in human is due to its interaction with SIRPg which is not express in mice. Surprisingly, the genetic statute of DCs donors on SIRPa V1 homozygote or heterozygote did not show any differences on human T cell activation.

Example 3: Impact of SIRP/CD47 Blockade on Polyclonal Stimulation

METHOD: hPBMC were isolated from buffy coat of healthy volunteers. CD4 or CD8 T cells were selected by positive selection using an AutoMACS (Miltenyi) and plated in 96-round well plate (50 000 cells/well). The proliferative signals were provided by either anti-CD3/anti-CD28 coated microbeads (Life Technologies) at a 1 bead for 1 T cell ratio during three days, or allogeneic mature dendritic cells generated in vitro at a 5 T cell for 1 mDC during 5 days. Antibodies targeting the SIRPa/CD47 and/or the SIRPg/CD47 pathways were added from the beginning of the proliferation test at a saturating concentration (10 µg/mL). Proliferation was measured by incorporation of $H^3$-thymidine during the last 12 h of culture. Anti-CD47 antibody (commercial references: B6H12), anti-SIRPa antibodies (HEFLB as referred in the patent (WO2017178653)).

Figure 7:
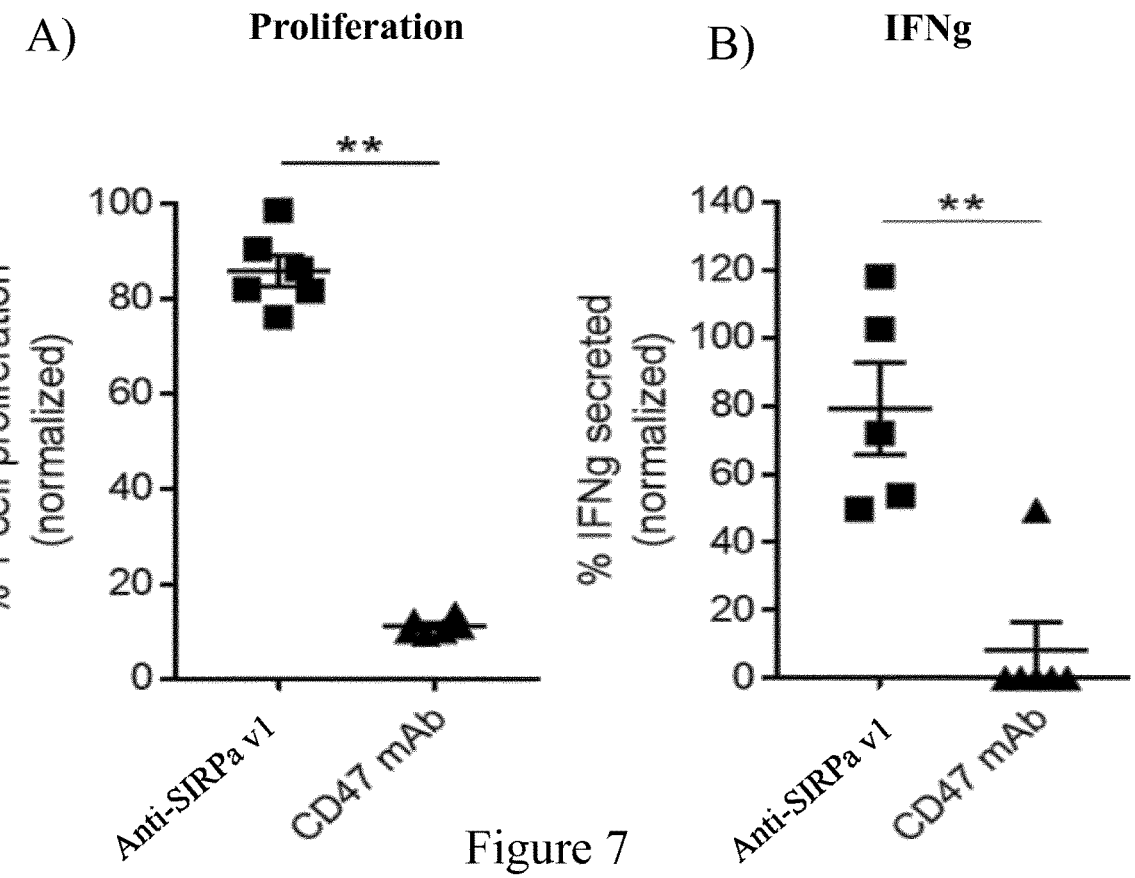
FIG. 7. Allogenic response of T cells (CD4 and CD8 positive cells) to anti-human SIRPa v1 and anti-human CD47 antibodies in presence of dendritic cells. Human T cells isolated from peripheral blood mononuclear cells from healthy volunteers were stimulated with allogeneic dendritic cells (DC) at a 5 T cell: 1 DC ratio for 5 days. Antibodies were added at day 0 of the culture. A: Proliferation measured by incorporation of $H^3$-thymidine during the last 12 h of culture. B: Percentage of IFNg secretion measured by ELISA. Results were normalized to the control conditions. Anti-SIRPa v1 (square) corresponds to cells treated with an in-house antibody specific to SIRPa v1, which does not bind SIRPa v2 and SIRPg. CD47 mAb (triangle) corresponds to cells treated with an antibody that binds to CD47.

RESULTS: to investigate the immunosuppressive effect of the blockade of CD47 on human T lymphocytes, PBMC were isolated from 3 different healthy volunteers and a part of the cells was irradiated (35 Gy). Each donor (responder) has been included in Mixte Lymphocyte Reaction with each of the two remaining donors (irradiated stimulators). Blocking antibodies were added at the beginning of the MLR and T cell proliferation was measured by thymidine incorporation in the last 16 h of a five-days-culture. Inventors found a strong inhibition of human T cell proliferation with anti-CD47 mAb whereas anti-SIRPa (in-house anti-human SIRPa v1 antibody) did not significantly differ from control conditions (FIG. 7). IFNg secretion which also reflects T cell activation was dosed in the supernatant of the 4-days culture. Inventors observed also a dramatic inhibition of the secretion of the cytokine with anti-CD47mAb (B6H12) indicating and confirming previous results from the inventors and other groups that CD47 is important for T cell activation in human.

Example 4: Effect of Anti-SIRPa Antibody on Macrophage Polarization Bioassay Using Monocytes from Healthy Donors: Bioassay Measuring Chemokine Production: MIP-1a/CCL-3 and MIP-1b/CCL-4

Figure 8:
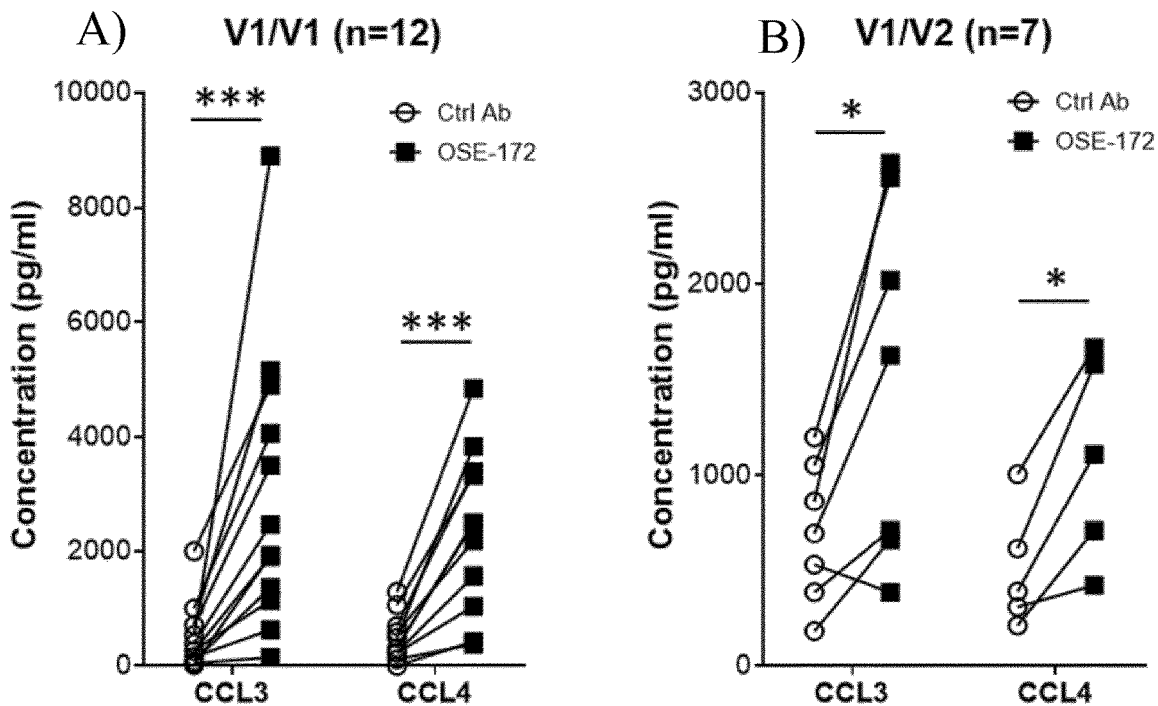
FIG. 8. Macrophage polarization bioassay comparing V1/V1 and V1/V2 donor monocytes treated with anti-SIRPa v1 antibody. MIP-1a/CCL-3 and MIP-1b/CCL-4 secretion were measured by ELISA in supernatant of cells not treated (cercle) or treated with an anti-human SIRPa v1 antibody (square). A: results obtained with cells from homozygote donors V1/V1. B: results obtained with cells from heterozygote donors V1/V2.

To investigate the impact of in-house anti-human SIRPa v1 antibody on macrophage polarization and activation, the secretion of some chemokines, more specifically MIP-1a/CCL-3 and MIP-1b/CCL-4, were measured in the supernatant of fresh or frozen human monocytes genotyped homozygous V1 for SIRPa or heterozygous V1/V2 cultured with GM-CSF to induce non-polarized immature macrophages (FIG. 8). Two sources of recombinant CD47-Fc were tested at 10 µg/ml: SinoBiological #12283-H02H and R&D systems #4670-CD-050. Quantification of MIP-1a/CCL-3 and MIP-1b/CCL4 was realized by ELISA in culture supernatants (R&D systems: Human CCL3/MIP-1 alpha DuoSet ELISA #DY270 and Human CCL4/MIP-1 betaDuoSet ELISA #DY271). Altogether, results showed that in the presence of coated CD47-Fc, in-house anti-human SIRPa v1 antibody, significantly increased the secretion of MIP-1a and MIP-1b, both on homozygous for V1 SIRPa (FIG. 8A) or heterozygous (V1/V2 genotype) donors (FIG. 8B).

Conclusion

Inventors identified that M1-associated chemokines MIP-1a/CCL-3 and MIP-1b/CCL-4 secretion is significantly increased with in-house anti-human SIRPa v1 antibody in the presence of coated recombinant CD47-Fc. CD47-Fc induces functional suppression of human myeloid cells, in particular by decreasing MIP-1a/CCL-3 and MIP-1b/CCL-4 basal secretion. Blocking SIRPa-CD47 interaction by an anti-SIRPa antibody restores myeloid function as shown by secretion of MIP-1a and MIP-1b in the supernatant. The genotype of the donors regarding of the SIRPa V1 allele expression has no impact on the induction of those chemokines, suggesting a threshold effect on the SIRPa blockade to observe a functional effect.

Example 5: SIRPa Binding Assay on Human Monocytes v2/v2 by Cytofluorometry

METHOD: To measure the binding of the anti-SIRPa antibodies on human monocytes, human Fc Receptor Binding Inhibitor (BD pharmingen; USA; reference 564220) was first added for 30 min at room-temperature to block human Fc receptors on human monocytes to reduce background. Then, an antibody was incubated for 30 mm at 4° C., and washed before stained 30 min at 4° C. with PE-labelled anti-human IgG Fc (Biolegend; USA; reference 409303). For the mouse antibodies, a PE-labelled anti-mouse igG (Jackson immunoresearch; reference 715-116-151) was used. Samples were analyzed on BD LSRII or Canto II cytofluorometer.

Figure 9:
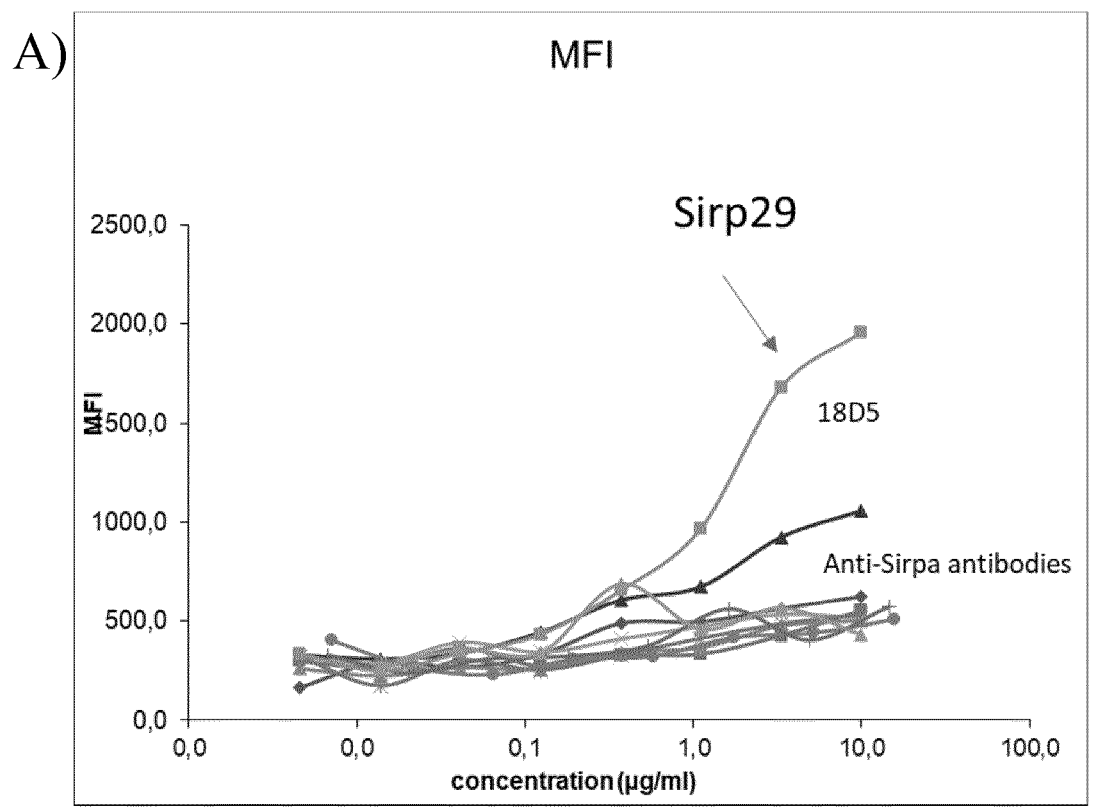
FIG. 9. Binding analysis of anti-SIRPa antibodies on human monocytes homozygote for SIRPa v2 by FACS and determination of the ED50 of the antibody against SIRPa v2 by ELISA. Assessment by cytofluorometry on human monocytes v2/v2 (previously stained with human Fc Receptor binding inhibitor) of chimeric 18D5 antibody or SIRP29 antibody or different humanized anti-SIRPa antibodies. Revelation was performed with a PE labeled mouse anti-human Fc mAb on Cantoll cytometer. ED50 is the concentration of the indicated antibody to reach 50% of the signal. A: Mean of Fluorescence Intensity of positive cells v2/v2 stained. B: determination of the ED50 by ELISA for each antibody. The ED50 was not detectable for most of the humanized 18D5 antibodies FIG. 10. Competition analysis by Blitz of CD47 on human SIRPg recombinant protein pre-incubated with anti-SIRP antibodies. SIRPg-His recombinant protein was immobilized onto a NINTA biosensor at 10 µg/ml and the indicated antibodies were added at 20 µg/ml (saturating concentration). Then CD47Fc was added at 100 µg/ml and affinity values were deduced after an association period (ka) of 120 s followed by a dissociation period of 120 s (kd) to determine affinity constant (KD). KD affinity of CD47 to SIRPg was determined in different conditions: in presence of the LSB2.20 antibody (an antibody that binds specifically to SIRPg); the kwar antibody, and the SIRP29 antibodies.

RESULTS: As shown in FIG. 9, the results indicate a binding of the SIRP29 antibody and the chimeric 18D5 antibody parent antibody of the invention on human monocytes SIRPa v2/v2 and no binding for all the humanized anti-SIRPa antibody (as measured with the MFI (Median Fluorescent Intensity) indicating that the humanization of the antibodies induces the loss of the SIRPa v2 specificity.

Example 6: Competition Analysis of the Anti-SIRPa Antibodies on the CD47-SIRPg Interaction by Blitz METHOD: This assay was performed with a Blitz (Forte Bio; USA; reference C22-2 No 61010-1). In a first step, hSIRPg-His (Sino Biologicals, Beijing, China; reference 11828-H08H) was immobilized at 10 μg/ml by histidine tail into a Ni-NTA biosensor (Forté Bio; USA; reference 18-0029) for 30 seconds. In a second step, an antibody was added at 20 μg/mL (saturating concentration) for 120 seconds. Then, human CD47Fc ((Sino Biologicals, Beijing, China; reference 12283-H02H) was associated at 100 μg/mL, in competition with different antibodies, for 120 seconds (LSB2.20, Kwar or SIRP29 antibodies). The dissociation of CD47Fc was made in kinetics buffer for 120 seconds. Analysis data was made with the Blitz pro 1.2 software, which calculated association constant (ka) and dissociation constant (kd) and determined the affinity constant KD (ka/kd).

RESULTS: As shown in FIG. 10, in normal condition the affinity of the CD47 to SIRPg is around $6.10^{-8}$ M, Kwar23 and SIRP29 significantly reduces the binding of CD47 to SIRPg, while the LSB2.20 a commercial anti-SIRPg antibody, does not disrupt the interaction CD47-SIRPg. These results underline the specificity of the in-house anti-SIRPa v1 antibody of the invention against the SIRPa compare to the antibodies of the prior art.

Example 7: Mammary 4T1 Preclinical Model: A Metastasis Model

This orthotopic and syngeneic 4T1 preclinical model was used to evaluate the effect of two different specific anti-mice SIRPa monotherapies in a model where myeloid cell infiltration is important and well described. Indeed, it was previously reported that 4T1 model is predominantly infiltrated by CD11 b+ myeloid cells (DuPré et al., 2007), in particular MDSC (Markowitz et al., 2013).

Figure 11:
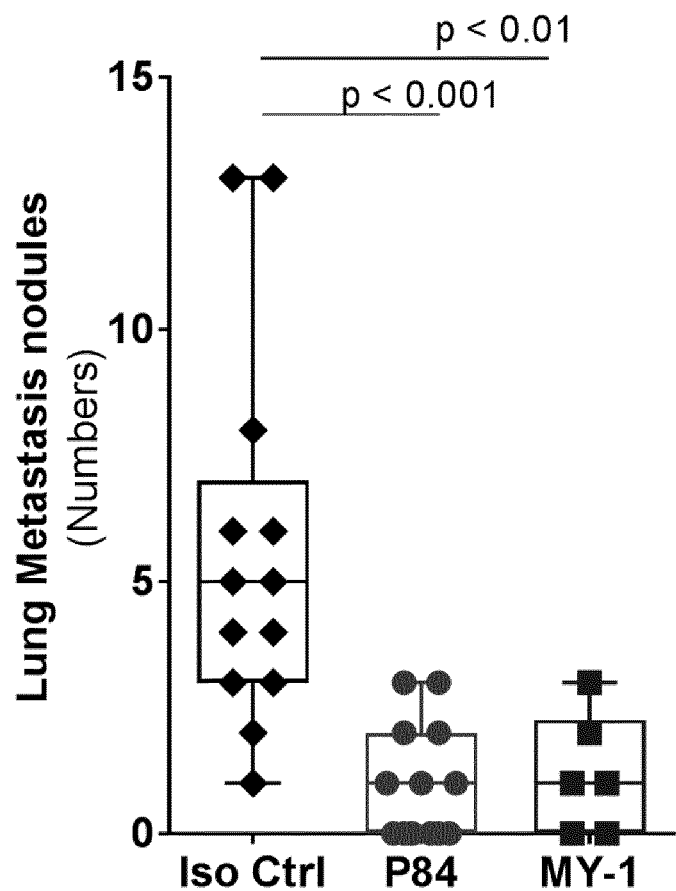
FIG. 11. Effect of anti-SIRPa antibodies on mice metastasis model of Mammary cancer. The 4T1 mammary cancer model was used to study the efficiency of mice anti-SIRPa (p84 antibody and MY-1 antibody) on lung metastasis. The figure represents the numbers of lung metastasis nodules in mice treated or not with anti-SIRPa antibodies. Mice treated with the isotopic control are represented with a diamond, mice treated with the p84 antibody are represented with a circle and those treated with the MY-1 antibody are represented with a square. Results are significant between control and each anti-SIRPa antibody.

This model is known to induce metastasis. The inventors have therefore collected the liver and the lung and numbered the metastases of mice treated or not with mouse anti-SIRPa antibodies. The isotype control and anti-SIRPa antibodies were used at 8 mg/kg from D4 to D28 (3 times/week). The blockade of SIRPa by two different antibodies targeting specifically SIRPa (and disrupting the binding of CD47 to SIRPa) demonstrated a potent clinical effect in monotherapy on the tumor development of an aggressive model of TNBC. Inventors also analyzed lung and liver metastasis after sacrifice by comparing P84 (Ref: MABS164 an Anti-SHPS-1 Antibody, clone P84 from Merck Millipore) and MY1-mG1 (described in Yanagita et al.) surrogates. Control mice developed lung metastases while no mice treated with MY1-mG1 or P84 did so. The FIG. 11 shows results on lung metastasis for P84 and MY-1 anti-SIRPa mAbs, both showing the same efficacy on lung metastasis.

These results in a mice model that does not express SIRPg on their cells underline the importance to target specifically SIRPa for cancer applications and more particularly for metastasis treatment or prevention. In human where cells express SIRPg, it will be useful to target specifically SIRPa without disrupting the CD47-SIRPg interaction such as the antibodies of the invention.

BIBLIOGRAPHY

Chang, Y., and Moore, P. S. (2012). Merkel Cell Carcinoma: A Virus-Induced Human Cancer. Annu. Rev. Pathol. Mech. Dis. 7, 123-144.

DuPré, S. A., Redelman, D., and Hunter, K. W. (2007). The mouse mammary carcinoma 4T1: characterization of the cellular landscape of primary tumours and metastatic tumour foci. Int. J. Exp. Pathol. 88, 351-360.

Haan, J. M. M. den, Lehar, S. M., and Bevan, M. J. (2000). Cd8+ but Not Cd8− Dendritic Cells Cross-Prime Cytotoxic T Cells in Vivo. J. Exp. Med. 192, 1685-1696.

Hassan, R., Thomas, A., Alewine, C., Le, D. T., Jaffee, E. M., and Pastan, I. (2016). Mesothelin Immunotherapy for Cancer: Ready for Prime Time? J. Clin. Oncol. 34, 4171-4179.

Hochrein, H., Shortman, K., Vremec, D., Scott, B., Hertzog, P., and O'Keeffe, M. (2001). Differential production of IL-12, IFN-alpha, and IFN-gamma by mouse dendritic cell subsets. J. Immunol. Baltim. Md. 1950 166, 5448-5455.

Liao, J. B. (2006). Viruses and Human Cancer. Yale J. Biol. Med. 79, 115-122.

Liu, Q., Wen, W., Tang, L., Qin, C.-J., Lin, Y., Zhang, H.-L., Wu, H., Ashton, C., Wu, H.-P., Ding, J., et al. (2016). Inhibition of SIRPα in dendritic cells potentiates potent antitumor immunity. Oncolmmunology 5, e1183850.

Liu, X., Pu, Y., Cron, K., Deng, L., Kline, J., Frazier, W. A., Xu, H., Peng, H., Fu, Y.-X., and Xu, M. M. (2015). CD47 blockade triggers T cell-mediated destruction of immunogenic tumors. Nat. Med. *advance online publication.*

Markowitz, J., Wesolowski, R., Papenfuss, T., Brooks, T. R., and Carson, W. E. (2013). Myeloid Derived Suppressor Cells in Breast Cancer. Breast Cancer Res. Treat. 140, 13-21.

Piccio, L., Vermi, W., Boles, K. S., Fuchs, A., Strader, C. A., Facchetti, F., Cella, M., and Colonna, M. (2005). Adhesion of human T cells to antigen-presenting cells through SIRPβ2-CD47 interaction costimulates T-cell proliferation. Blood 105, 2421-2427.

Takenaka, K., Prasolava, T. K., Wang, J. C. Y., Mortin-Toth, S. M., Khalouei, S., Gan, O. I., Dick, J. E., and Danska, J. S. (2007). Polymorphism in Sirpa modulates engraftment of human hematopoietic stem cells. Nat. Immunol. 8, 1313-1323.

Xu, M. M., Pu, Y., Han, D., Shi, Y., Cao, X., Liang, H., Chen, X., Li, X.-D., Deng, L., Chen, Z. J., et al. (2017). Dendritic Cells but Not Macrophages Sense Tumor Mitochondrial DNA for Cross-priming through Signal Regulatory Protein α Signaling. Immunity 47, 363-373.e5.

Yanagita, T., Murata, Y., Tanaka, D., Motegi, S., Arai, E., Daniwijaya, E. W., Hazama, D., Washio, K., Saito, Y., Kotani, T., et al. Anti-SIRPα antibodies as a potential new tool for cancer immunotherapy. JCI Insight 2.

Zong, J., Keskinov, A. A., Shurin, G. V., and Shurin, M. R. (2016). Tumor-derived factors modulating dendritic cell function. Cancer Immunol. Immunother. CII 65, 821-833.

The invention claimed is:

1. A method of treating a cancer in a subject that expresses SIRPa v1, the method comprising administering to a subject a therapeutic amount of an anti-human SIRPa antibody, antigen-binding fragment thereof, or modified antibody thereof, which comprises:
   a) a heavy chain variable domain comprising HCDR1, HCDR2 and HCDR3, wherein: HCDR1 comprises the amino acid sequence set forth in SEQ ID NO: 9, HCDR2 comprises the amino acid sequence set forth in SEQ ID NO: 10 or SEQ ID NO: 11, HCDR3 comprises the amino acid sequence set forth in SEQ ID NO: 12, SEQ ID NO: 13, SEQ ID NO: 14, or SEQ ID NO: 15; and
   b) a light chain variable domain comprising the amino acid sequence set forth in SEQ ID NO: 16 or SEQ ID NO: 17, wherein the antibody, antigen-binding fragment thereof, or modified antibody thereof, enhances cross presentation of an antigen expressed in said disease and is involved in eliciting a T cell response suitable for the treatment of said disease.

2. The method of claim 1, wherein the antibody, antigen-binding fragment thereof, or modified antibody thereof,
   binds specifically to human SIRPa v1 and inhibits the binding of human CD47 to human SIRPa v1,
   does not prevent or inhibit the binding of human CD47 to human SIRPg, and
   does not bind specifically to human SIRPg.

3. A method of treating a cancer in a subject that expresses SIRPa v1, the method comprising administering to a SIRPa v1 positive subject a therapeutic amount of an anti-human SIRPa antibody, antigen-binding fragment thereof, or modified antibody thereof, which comprises:
   (a) a heavy chain variable domain comprising HCDR1, HCDR2 and HCDR3, wherein:
   HCDR1 comprises the amino acid sequence set forth in SEQ ID NO: 9
   HCDR2 comprises the amino acid sequence set forth in SEQ ID NO: 10 or SEQ ID NO: 11,
   HCDR3 comprises the amino acid sequence set forth in SEQ ID NO: 12, SEQ ID NO: 13, SEQ ID NO: 14, or SEQ ID NO: 15; and
   (b) a light chain variable domain comprising of the amino acid sequence set forth in SEQ ID NO: 16 or SEQ ID NO: 17;
   wherein the anti-human SIRPa antibody, antigen-binding fragment thereof, or modified antibody thereof inhibits the binding of human CD47 to human SIRPa v1 and does not prevent or inhibit the binding of human CD47 to human SIRPa v2.

4. The method of claim 1,
   wherein the heavy chain variable domain comprises the amino acid sequence set forth in SEQ ID NO: 18, SEQ ID NO: 19, SEQ ID NO: 20; SEQ ID NO: 21; SEQ ID NO: 22; or SEQ ID NO: 23; and
   wherein the light chain variable domain comprises the amino acid sequence set forth in SEQ ID NO: 17.

5. The method of claim 1 wherein the cancer is selected from the group consisting of inflammatory cancer, cancer with infiltrated myeloid cells, metastatic cancer, and melanoma.

6. The method of claim 1, wherein the anti-human SIRPa antibody, antigen-binding fragment thereof, or modified antibody thereof comprises the following properties:
   it does not bind specifically to human SIRPa v2;
   it does not inhibit the binding of human CD47 to human SIRPg;
   it does not bind specifically to human SIRPg;
   it binds with human SIRPa v1 with an affinity of at least $10E^{-9}$ M; and
   it enhances the cross-presentation of at least one antigen by Antigen Presenting Cells to human T cells.

7. The method of claim 1, wherein at least one antigen:
   (i) selected from the group consisting of antigens from Human Papilloma Virus, Epstein-Barr Virus, Merkel cell polyomavirus, Human Immunodeficiency Virus, Human T-cell Leukemia Virus, Human Herpes Virus 8, Hepatitis B virus, Hepatitis C virus, HCV, HBC, and Cytomegalovirus, or
   (ii) selected from the group of single-point mutated antigens derived from the group consisting of the antigens of ctnnb1 gene, casp8 gene, her2 gene, p53 gene, kras gene, and nras gene, or
   (iii) selected from the group of tumor antigens issued or derived from the group consisting of ras oncogene, BCR-ABL tumor antigens, ETV6-AML1 tumor antigens, melanoma-antigen encoding genes (MAGE), BAGE antigens, GAGE antigens, ssx antigens, ny-eso-1 antigens, cyclin-A1 tumor antigens, MART-1 antigen, gp100 antigen, CD19 antigen, prostate specific antigen, prostatic acidic phosphatase antigen, carcinoembryonic antigen, alphafetoprotein antigen, carcinoma antigen 125, mucin 16 antigen, mucin 1 antigen, human telomerase reverse transcriptase antigen, EGFR antigen, MOK antigen, RAGE-1 antigen, PRAME antigen, wild-type p53 antigen, oncogene ERBB2 antigen, sialyl-Tn tumor antigen, Wilms tumor 1 antigen, mesothelin antigen, carbohydrate antigens, B-catenin antigen, MUM-1 antigen, CDK4 antigen, ERBB2IP antigen, and Melan-A melanoma tumor-associated antigen (TAA),
   is expressed or has been detected in the subject.

8. A method of treating a cancer in a subject that expresses SIRPa v1, the method comprising administering to a subject a pharmaceutical composition comprising a therapeutic amount of the anti-human SIRPa antibody, antigen-binding fragment thereof, or modified antibody thereof according to claim 1 and at least one pharmaceutical vehicle.

9. A method of treating a cancer in a subject that expresses SIRPa v1, the method comprising administering to a subject a combination of compounds comprising:
  (i) an anti-human SIRPa antibody, antigen-binding fragment thereof, or modified antibody thereof, according to claim 1; and
  (ii) at least one second therapeutic agent selected from the group consisting of chemotherapeutic agents, radiotherapy agents, immunotherapeutic agents, cell therapy agents, antibiotics and probiotics.

10. The method of claim 9, wherein the combination is suitable to elicit an immune response within a subject that elicits a T cell response suitable to treat the disease, said activation comprising (i) activating T cells; and/or (ii) enhancing the cross-presentation of at least one antigen by dendritic cells to CD8+T cells; and/or (iii) enhancing macrophages polarization; or (i), (ii) and (iii).

11. A method of increasing the cross-presentation of an antigen by antigen presenting cells to T cells, said method comprising the administration to a SIRPa v1 positive subject a compound selected from the group consisting of an anti-human SIRPa antibody, an antigen-binding fragment thereof, and a modified antibody thereof, according to claim 1, said compound having at least the following properties:
  i) it does not specifically bind to human SIRPa v2;
  ii) it binds to human SIRPa v1 with an affinity of at least $1E^{-9}$ M;
  iii) it decreases or inhibits the binding of human CD47 to human SIRPa v1; and
  iv) it does not prevent or inhibit the binding of human CD47 to human SIRPg.

12. A method for assessing the likelihood of effectiveness of a treatment with an anti-human SIRPa v1 antibody, antigen-binding fragment thereof, or modified antibody thereof, within a human subject, said method comprising:
  determining the presence of human SIRPa v1 in a biological sample previously obtained from the human subject; wherein the human subject is SIRPa v1-positive; and
  administering a therapeutic amount of an anti-SIRPa antibody, antigen-binding fragment thereof, or modified antibody thereof, according to claim 1.

13. The method according to claim 12, wherein the human subject to be treated has a cancer or is likely to develop a cancer.

14. The method of claim 4, wherein the heavy chain variable domain comprises the amino acid sequence set forth in SEQ ID NO: 20.

15. The method of claim 1, wherein the method is a method of therapeutic vaccination.

16. The method of claim 3,
  wherein the heavy chain variable domain comprises the amino acid sequence set forth in SEQ ID NO: 18, or in SEQ ID NO: 19, or in SEQ ID NO: 20;
  or in SEQ ID NO: 21; or in SEQ ID NO: 22; or in SEQ ID NO: 23; and
  wherein the light chain variable domain comprises the amino acid sequence set forth in SEQ ID NO: 17.

17. The method of claim 16, wherein the heavy chain variable domain comprises the amino acid sequence set forth in SEQ ID NO: 20.

18. The method of claim 3, wherein the cancer is selected from the group consisting of inflammatory cancer, cancer with infiltrated myeloid cells, metastatic cancer, and melanoma.

19. The method of claim 1, wherein the cancer is selected from the group consisting of breast, ovarian, and lung cancer.

20. The method of claim 9, wherein the cancer is selected from the group consisting of breast, ovarian, and lung cancer.

* * * * *